US 11,845,802 B2

(12) United States Patent
Liu

(10) Patent No.: US 11,845,802 B2
(45) Date of Patent: *Dec. 19, 2023

(54) COMBINATION THERAPY WITH A GLUCAGON RECEPTOR (GCGR) ANTIBODY AND AN ANTI-CD3 ANTIBODY

(71) Applicant: NGM Biopharmaceuticals, Inc., South San Francisco, CA (US)

(72) Inventor: Zhonghao Liu, Redwood City, CA (US)

(73) Assignee: NGM Biopharmaceuticals, Inc., South San Francisco, CA (US)

(*) Notice: Subject to any disclaimer, the term of this patent is extended or adjusted under 35 U.S.C. 154(b) by 241 days.

This patent is subject to a terminal disclaimer.

(21) Appl. No.: 17/177,762

(22) Filed: Feb. 17, 2021

(65) Prior Publication Data

US 2021/0284746 A1 Sep. 16, 2021

Related U.S. Application Data

(63) Continuation of application No. 16/522,778, filed on Jul. 26, 2019, now Pat. No. 10,961,315.

(60) Provisional application No. 62/711,368, filed on Jul. 27, 2018.

(51) Int. Cl.
| | | |
|---|---|---|
| *C07K 16/28* | (2006.01) | |
| *A61P 3/10* | (2006.01) | |
| *A61K 39/395* | (2006.01) | |
| *A61K 39/00* | (2006.01) | |
| *A61K 45/06* | (2006.01) | |

(52) U.S. Cl.
CPC ...... *C07K 16/2869* (2013.01); *A61K 39/3955* (2013.01); *A61K 45/06* (2013.01); *A61P 3/10* (2018.01); *C07K 16/2809* (2013.01); *A61K 2039/507* (2013.01); *C07K 2317/21* (2013.01); *C07K 2317/24* (2013.01); *C07K 2317/31* (2013.01); *C07K 2317/565* (2013.01); *C07K 2317/76* (2013.01); *C07K 2317/92* (2013.01)

(58) Field of Classification Search
CPC ............ C07K 16/2869; C07K 2317/21; C07K 2317/24; C07K 2317/565; C07K 2317/76; A61K 39/3955; A61K 2039/507; A61P 3/10

See application file for complete search history.

(56) References Cited

U.S. PATENT DOCUMENTS

| | | | |
|---|---|---|---|
| 5,317,092 A | 5/1994 | Markussen | |
| 5,770,445 A | 6/1998 | Kindsvogel et al. | |
| 5,776,725 A | 7/1998 | Kindsvogel et al. | |
| 5,919,635 A | 7/1999 | Kindsvogel et al. | |
| 7,947,809 B2 | 5/2011 | Yan et al. | |
| 7,968,686 B2 | 6/2011 | Korytko et al. | |
| 8,158,759 B2 | 4/2012 | Yan et al. | |
| 8,545,847 B2 | 10/2013 | Okamoto et al. | |
| 8,771,696 B2 | 7/2014 | Harp et al. | |
| 9,102,732 B2 | 8/2015 | Lee et al. | |
| 9,127,068 B2 | 9/2015 | Okamoto et al. | |
| 9,248,189 B2 | 2/2016 | Forgie et al. | |
| 9,358,287 B2 | 6/2016 | Harp et al. | |
| 9,587,029 B2 | 3/2017 | Okamoto et al. | |
| 10,961,315 B2 | 3/2021 | Liu | |
| 10,995,145 B2 | 5/2021 | Shen et al. | |
| 2008/0213288 A1 | 9/2008 | Michelsen et al. | |
| 2009/0041784 A1 | 2/2009 | Yan et al. | |
| 2009/0252727 A1 | 10/2009 | Korytko et al. | |
| 2011/0212092 A1 | 9/2011 | Korytko et al. | |
| 2012/0128679 A1 | 5/2012 | Okamoto et al. | |
| 2013/0149315 A1 | 6/2013 | Lee et al. | |
| 2013/0251728 A1 | 9/2013 | Harp et al. | |
| 2013/0344538 A1 | 12/2013 | Okamoto et al. | |
| 2014/0255419 A1 | 9/2014 | Harp et al. | |
| 2014/0335091 A1 | 11/2014 | Forgie et al. | |
| 2015/0337045 A1 | 11/2015 | Okamoto et al. | |
| 2016/0257757 A1 | 9/2016 | Harp et al. | |
| 2016/0311912 A1 | 10/2016 | Forgie et al. | |
| 2017/0129960 A1 | 5/2017 | Okamoto et al. | |
| 2018/0273629 A1 | 9/2018 | Shen et al. | |
| 2020/0048356 A1 | 2/2020 | Liu | |
| 2021/0332144 A1 | 10/2021 | Shen et al. | |

FOREIGN PATENT DOCUMENTS

| | | |
|---|---|---|
| CN | 101589062 | 11/2009 |
| CN | 101983208 | 3/2011 |
| CN | 102482350 | 5/2012 |
| CN | 103314011 | 9/2013 |
| CN | 104231083 | 12/2014 |
| CN | 105189650 | 12/2015 |
| JP | 2016-520058 | 7/2016 |
| RU | 2505603 | 1/2014 |
| RU | 2521669 | 7/2014 |
| RU | 2526517 | 8/2014 |
| WO | WO 1994/005789 | 3/1994 |
| WO | WO 2006/005469 | 7/2005 |

(Continued)

OTHER PUBLICATIONS

Bostrom et al., "Improving antibody binding affinity and specificity for therapeutic development," In Therapeutic Antibodies, Humana Press, 2009, pp. 353-376.

Chen et al., "Enhancement and destruction of antibody function by somatic mutation: unequal occurrence is controlled by V gene combinatorial associations," The EMBO journal, Jun. 1995, 14(12):2784-94.

Comoglio et al., "Drug development of MET inhibitors: targeting oncogene addiction and expedience," Nature reviews Drug discovery, Jun. 2008, 7(6):504-16.

(Continued)

*Primary Examiner* — Robert S Landsman
(74) *Attorney, Agent, or Firm* — Fish & Richardson P.C.

(57) ABSTRACT

The present disclosure provides methods comprising a glucagon receptor antagonist in combination with an immunotherapeutic agent for treatment of disease.

23 Claims, 4 Drawing Sheets

Specification includes a Sequence Listing.

(56) References Cited

FOREIGN PATENT DOCUMENTS

| WO | WO 2008/036341 | 3/2008 |
|----|----------------|--------|
| WO | WO 2009/120530 | 10/2009 |
| WO | WO 2011/030935 | 3/2011 |
| WO | WO 2012/071372 | 5/2012 |
| WO | WO 2013/059531 | 4/2013 |
| WO | WO 2014/181229 | 11/2014 |
| WO | WO 2015/154795 | 10/2015 |
| WO | WO 2015/189698 | 12/2015 |
| WO | WO 2016/044337 | 3/2016 |
| WO | WO 2016/161154 | 6/2016 |
| WO | WO 2017/040986 | 3/2017 |
| WO | WO 2017/062693 | 4/2017 |
| WO | WO 2017/120261 | 7/2017 |
| WO | WO 2018/075792 | 4/2018 |
| WO | WO 2018/140729 | 8/2018 |

OTHER PUBLICATIONS

Di Zenzo et al., "The intracellular and extracellular domains of BP180 antigen comprise novel epitopes targeted by pemphigoid gestationis autoantibodies," Journal of investigative dermatology, Apr. 2007, 127(4):864-73.

Lu et al., "Acquired antagonistic activity of a bispecific diabody directed against two different epitopes on vascular endothelial growth factor receptor 2," Journal of immunological methods, Nov. 19, 1999, 230(1-2):159-71.

Pakula et al., "Genetic analysis of protein stability and function," Annual review of genetics, Dec. 1989, 23(1):289-310.

Palmer et al., "C-peptide is the appropriate outcome measure for type 1 diabetes clinical trials to preserve β-cell function: report of an ADA workshop, Oct. 21-22, 2001," Diabetes, Jan. 2004, 53(1):250-64.

Rudikoff et al., "Single amino acid substitution altering antigen-binding specificity," Proceedings of the National Academy of Sciences, Mar. 1982, 79(6):1979-83.

Sela-Culang et al., "The structural basis of antibody-antigen recognition," Frontiers in immunology, Oct. 8, 2013, 4:302, 14 pages.

Wark et al., "Latest technologies for the enhancement of antibody affinity," Advanced drug delivery reviews, Aug. 7, 2006, 58(5-6):657-70.

Gonzales et al., "Minimizing the immunogenicity of antibodies for clinical application," Tumour Biol, Jan.-Feb. 2005, 26(1):31-43.

Krieg et al., "Functional analysis of B and T lymphocyte attenuator engagement on CD4+ and CD8+ T cells," J Immunol, Nov. 2005, 175(10):6420-7.

Morris et al., "Epitope Mapping of Protein Antigens by Competition ELISA," The Protein Protocols Handbook, 1996, pp. 595-600.

Wu et al., "Humanization of a murine monoclonal antibody by simultaneous optimization of framework and CDR residues," J Mol Biol., Nov. 1999, 294(1):151-62.

Arellano et al., "Regulatory T Cell-based Therapies for Autoimmunity," Discov Med., 2016, 22(119):73-80.

Buggy et al., "Glucagon glucagon-like peptide I receptor chimeras reveal domains that determine specificity of glucagon binding," J. Biol. Chem, 1995, 270(13):7474-7478.

Cerf, "Beta cell dysfunction and insulin resistance," Front. Endocrinol, 2013, 4(37): 13 pages.

Daifotis et al., "Anti-CD3 clinical trials in type 1 diabetes mellitus," Clinical Immunology, 2013, 149:268-278.

Damond et al., "Blockade of glucagon signaling prevents or reverses diabetes onset only if residual β-cells persist," eLife, 2016, 5:e13828, 18 pages.

Deweerdt, "Cell Savers," Nature, May 2012, 485:54-55.

Dimeglio et al., "Type 1 Diabetes," The Lancet, 2018, 391(10138):2449-2462.

Edwards et al., "The remarkable flexibility of the human antibody repertoire; isolation of over one thousand different antibodies to a single protein," J. Mol. Biol., 2003, 334:103-118.

Fine et al., "Glucocorticoids Reprogram β-Cell Signaling to Preserve Insulin Secretion," Diabetes, Feb. 2018, 67(2):278-290.

Gelling et al., "Pancreatic Beta-Cell Overexpression of the Glucagon Receptor Gene Results in Enhanced Beta-Cell Function and Mass," Am J Physiol Endocrinol Metab., Sep. 2009, 297(3):E695-707.

Gelling et al., "Lower blood glucose, hyperglucagonemia, and pancreatic alpha cell hyperplasia in glucagon receptor knockout mice," Proc. Natl. Acad. Sci. USA, 2003,100(3):1438-1443.

GenBank Accession No. 005585314.1, "Predicted: glucagon receptor isoform X3 [Macaca fascicularis]" Jan. 25, 2016, 2 pages.

Gu et al., "Long-term inhibition of the glucagon receptor with a monoclonal antibody in mice causes sustained improvement in glycemic control, with reversible alpha-cell hyperplasia and hyperglucagonemia," J. Pharmacol. Exp. Ther, 2009, 331(3):871-881.

Kazda et al., "Evaluation of Efficacy and Safety of the Glucagon Receptor Antagonist LY2409021 in Patients With Type 2 Diabetes: 12- and 24-Week Phase 2 Studies," Diabetes Care, Jul. 2016, 39:1241-1249.

Koizumi et al., "Sub-chronic Stimulation of Glucocorticoid Receptor Impairs and Mineralocorticoid Receptor Protects Cytosolic Ca2+ Responses to Glucose in Pancreatic Beta-Cells," J Endocrino, May 2008, 197(2):221-9.

Kopan et al., "Approaches in Immunotherapy, Regenerative Medicine, and Bioengineering for Type 1 Diabetes," Frontiers in Immunology, Jun. 2018, 9(1354): 18 pages.

Kostic et al., "A first-in-human pharmacodynamic and pharmacokinetic study of a fully human anti-glucagon receptor monoclonal antibody in normal healthy volunteers," Diabetes Obes. Metabl., 2017, 20(2):283-291.

Koth et al., "Molecular basis for negative regulation of the glucagon receptor," Proc. Natl. Acad. Sci. USA, 2012, 109(36):14393-14398.

Kuhn et al., "Therapeutic anti-CD3 monoclonal antibodies: from bench to bedside," Immunotherapy, 2016, 8(8), 889-906.

Leighton et al, "A Practical Review of C-Peptide Testing in Diabetes," Diabetes Therapy, Jun. 2017, 8:475-487.

Lloyd et al., "Modelling the human immune response: performance of a 1011 human antibody repertoire against a broad panel of therapeutically relevant antigens," Protein Engineering, Design, & Selection, 2009, 22(3):159-168.

Longuet et al., "Liver-specific disruption of the murine glucagon receptor produces α-cell hyperplasia: evidence for a circulating α-cell growth factor," Diabetes, 2013, 62(4):1196-1205.

Malin et al, "β-Cell Dysfunction Is Associated with Metabolic Syndrome Severity in Adults," Mar. 2014, Metabolic Syndrome and Related Disorders, 12:79-85.

Mukund et al., "Inhibitory mechanism of an allosteric antibody targeting the glucagon receptor," J. Biol. Chem, 2013, 288(50):36168-36178.

Okamoto et al., "Glucagon Receptor Blockade With a Human Antibody Normalizes Blood Glucose in Diabetic Mice and Monkeys," Endocrinology, 2015, 156(8):2781-2794.

PCT International Preliminary Report on Patentability in International Appln. No. PCT/US2018/015452, dated Jul. 30, 2019, 6 pages.

PCT International Preliminary Report on Patentability in International Appln. No. PCT/US2019/043609, dated Feb. 2, 2021, 8 pages.

PCT International Search Report and Written Opinion in International Appln. No. PCT/US2018/015452, dated Apr. 15, 2018, 8 pages.

PCT International Search Report and Written Opinion in International Appln. No. PCTUS2019/043609, dated Oct. 8, 2019, 16 pages.

Pearson et al., "Clinical Trials, Triumphs, and Tribulations of Glucagon Receptor Antagonists," Diabetes Care, 2016, 39:1075-1077.

Penaranda et al., "Anti-CD3 Therapy Promotes Tolerance by Selectively Depleting Pathogenic Cells while Preserving Regulatory T Cells," J Immunol, 2011, 187:2015-2022.

Pettus et al., "Effect of a glucagon receptor antibody (REMD-477) in type 1 diabetes: A randomized controlled trial," Diabetes, Obesity and Metabolism, 2018, 20(5):1302-1305.

(56) References Cited

OTHER PUBLICATIONS

Scheen et al., "Investigational glucagon receptor antagonists in Phase I and II clinical trials for diabetes," Expert. Opin. Investig. Drugs, 2017, 26(12):1373-1389.
Sloop et al., "Hepatic and glucagon-like peptide-1-mediated reversal of diabetes by glucagon receptor antisense oligonucleotide inhibitors," J. Clin. Invest, 2004, 113(11):1571-1581.
Tooley et al., "New and future immunomodulatory therapy in type 1 diabetes," Trends Mol Med., Mar. 2012, 18(3):173-181.
Waldron-Lynch et al., "Immunomodulatory therapy to preserve pancreatic β-cell function in type 1 diabetes," Nature Reviews Drug Discovery, Jun. 2011, 10(6):439-452.
Wang et al., "Glucagon receptor antibody completely suppresses type 1 diabetes phenotype without insulin by disrupting a novel diabetogenic pathway," Proceedings of National Academy of Sciences PNAS, 2015, 112(8):2503-2508.
Yan et al., "Fully Human Monoclonal Antibodies Antagonizing the Glucagon Receptor Improve Glucose Homeostasis in Mice and Monkeys," J. Pharmacol. Exp. Ther, 2009, 329(1):102-111.
Yang et al., "Conformational states of the full-length glucagon receptor," Nat. Commun, 2015, 6:7859, 13 pages.

COMBINATION THERAPY WITH A GLUCAGON RECEPTOR (GCGR) ANTIBODY AND AN ANTI-CD3 ANTIBODY

CROSS-REFERENCE TO RELATED APPLICATIONS

This application is a continuation of U.S. patent application Ser. No. 16/522,778, filed Jul. 26, 2019, now issued as U.S. Pat. No. 10,961,315, which claims the priority benefit of U.S. Provisional Application No. 62/711,368, filed Jul. 27, 2018, each of which is hereby incorporated by reference herein in its entirety.

SEQUENCE LISTING

The instant application contains a Sequence Listing which has been submitted electronically in ASCII format and is hereby incorporated by reference in its entirety. Said ASCII copy, created on Feb. 11, 2021, is named 47702-0012002SEQ.txt and is 67.5 kb in size.

FIELD

The present disclosure generally relates to methods of treating and/or preventing diseases, disorders, and conditions using glucagon receptor antagonists, such as an anti-GCGR antibody, in combination with immunotherapeutic agents.

BACKGROUND

Glucagon is a 29-amino acid peptide hormone secreted by pancreatic alpha cells. Glucagon secretion generally increases in response to falling blood glucose levels, for example, during fasting. Glucagon can raise the concentration of blood glucose by stimulating hepatic glycogenolysis and gluconeogenesis. In contrast, insulin is produced by pancreatic beta cells. The stimulus for insulin secretion is high blood glucose. Although there is always a low level of insulin secreted by the pancreas, the amount secreted into the blood increases as blood glucose rises. Similarly, as blood glucose falls, the amount of insulin secreted by the pancreatic beta cells goes down. Acting together, glucagon and insulin help maintain normal blood glucose levels.

Glucagon binds to and activates the glucagon receptor (GCGR). GCGR is a member of the class B type of G-protein coupled receptors (GPCRs). GPCRs are characterized by a N-terminal extracellular domain, a core seven alpha-helix transmembrane region, and a cytoplasmic C-terminal region. Typically, GPCRs are associated with one or more intracellular signaling pathways via effector proteins. The effector proteins are heterotrimeric guanine-nucleotide binding proteins (G proteins), such as Ga (Gαs, Gαi, and Gαo), Gβ, and Gγ.

Through G protein coupling, GCGR stimulation can result in activation of adenylyl cyclase and cAMP-dependent intracellular signaling pathways as well as phosphoinositol-mediated signaling. Subsequent increases in the expression of gluconeogenic enzymes, including phosphoenolpyruvate carboxykinase, fructose-1,6-bisphosphatase, and glucose-6-phosphatase, promote gluconeogenesis. In addition, GCGR signaling can result in activation of glycogen phosphorylase and inhibition of glycogen synthase, and thereby promote glycogenolysis.

In a healthy subject pancreatic beta cells function to store and release insulin. Typically, beta cells respond quickly to spikes in blood glucose concentrations by secreting some of their stored insulin while simultaneously producing more. Problems arise when blood glucose levels are not regulated efficiently.

Diseases, disorders, or conditions associated with unregulated blood glucose levels include, hyperglycemia and the health issues resulting from hyperglycemia, including Type 1 and Type 2 diabetes. Diseases, disorders, or conditions associated with beta cell dysfunction include hyperglycemia and metabolic diseases, such as Type 1 and Type 2 diabetes. A subject's ability to produce and secrete insulin into the blood and to regulate blood glucose can be severely impaired when the subject has a disease associated with beta cell dysfunction. New methods and therapeutic agents for treating diseases, disorders, or conditions associated with unregulated blood glucose levels, hyperglycemia, and/or beta cell dysfunction are needed.

SUMMARY

The present disclosure provides methods of treating or preventing diseases such as diabetes, wherein the methods comprise administering to a subject in need thereof a glucagon receptor (GCGR) antagonist in combination with an immunotherapeutic agent. Combination therapy with at least two therapeutic agents often uses agents that work by different mechanisms of action, and/or target different pathways and may result in additive or synergetic effects. Combination therapy may allow for a lower dose of each agent than used in monotherapy, thereby reducing toxic side effects and/or increasing the therapeutic index of the agent (s). Combination therapy may decrease the likelihood that resistance to an agent will develop. Combination therapy comprising an immunotherapeutic agent may allow one agent to modulate an immune response to a cell or cells while the second agent may be effective at modulating a specific biological pathway. In addition, the order and/or timing of the administration of each therapeutic agent may affect the overall efficacy of a drug combination.

In one aspect, the disclosure provides methods of treating diabetes. In some embodiments, a method of treating diabetes in a subject (e.g., a human) comprises administering to the subject a therapeutically effective amount of a GCGR antagonist and a therapeutically effective amount of an immunotherapeutic agent. In some embodiments, the diabetes is newly diagnosed. In some embodiments, the diabetes is autoimmune diabetes. In some embodiments, the diabetes is Type 1 diabetes. In some embodiments, the Type 1 diabetes is latent autoimmune diabetes of adults (LADA). In some embodiments, the Type 1 diabetes is new onset Type 1 diabetes. In some embodiments, the diabetes is Type 2 diabetes.

In another aspect, the disclosure provides methods of reducing or lowering blood glucose levels, increasing C-peptide levels, and/or increasing insulin levels. In some embodiments, a method of reducing or lowering blood glucose levels in a subject (e.g., a human) comprises administering to the subject a therapeutically effective amount of a GCGR antagonist and a therapeutically effective amount of an immunotherapeutic agent. In some embodiments, a method of increasing C-peptide levels in the blood of a subject comprises administering to the subject a therapeutically effective amount of a GCGR antagonist and a therapeutically effective amount of an immunotherapeutic agent. In some embodiments, a method of increasing insulin levels in the blood of a subject comprises administering to the subject a therapeutically effective amount of a GCGR antagonist and a therapeutically effective amount of an immunotherapeutic agent.

In another aspect, the disclosure provide methods of treating hyperglycemia. In some embodiments, a method of treating hyperglycemia in a subject (e.g., a human) comprises administering to the subject a therapeutically effective amount of a GCGR antagonist and a therapeutically effective amount of an immunotherapeutic agent.

In another aspect, the disclosure provide methods of treating metabolic syndrome. In some embodiments, a method of treating metabolic syndrome in a subject (e.g., a human) comprises administering to the subject a therapeutically effective amount of a GCGR antagonist and a therapeutically effective amount of an immunotherapeutic agent.

In another aspect, the disclosure provide methods of treating a disease, disorder, or condition associated with beta cell dysfunction. In some embodiments, a method of treating a disease, disorder, or condition associated with beta cell dysfunction in a subject (e.g., a human) comprises administering to the subject a therapeutically effective amount of a GCGR antagonist and a therapeutically effective amount of an immunotherapeutic agent. In some embodiments, the disease, disorder, or condition is diabetes. In some embodiments, the disease, disorder, or condition is autoimmune diabetes. In some embodiments, the disease, disorder, or condition is Type 1 diabetes. In some embodiments, the disease, disorder, or condition is Type 2 diabetes. In some embodiments, the disease, disorder, or condition is metabolic syndrome.

In some embodiments of each of the aforementioned aspects, as well as other aspects and embodiments described elsewhere herein, the treatment method (i) reduces blood glucose levels in the subject; (ii) increases C-peptide levels in the blood of the subject; (iii) increases C-peptide levels in the pancreas of the subject; (iv) reduces HbA1c in the blood of the subject; and/or (v) reduces supplemental insulin use by the subject. In some embodiments, the treatment method reduces blood glucose levels in the subject. In some embodiments, the treatment method increases C-peptide levels in the blood of the subject. In some embodiments, the treatment method increases C-peptide levels in the pancreas of the subject. In some embodiments, the treatment method reduces HbA1c in the blood of the subject. In some embodiments, the treatment method reduces supplemental insulin use by the subject. In some embodiments, C-peptide is measured in a blood sample, a serum sample, a plasma sample, or a pancreatic sample. In some embodiments, the subject is a human.

In another aspect, the disclosure provides methods of improving beta cell function. In some embodiments, a method of improving beta cell function in a subject (e.g., a human) comprises administering to the subject a therapeutically effective amount of a GCGR antagonist and a therapeutically effective amount of an immunotherapeutic agent. In some embodiments, an improvement in beta cell function is indicated by (i) a reduction in blood glucose levels in the subject; (ii) an increase in C-peptide levels in the blood of the subject; (iii) an increase in C-peptide levels in the pancreas of the subject; (iv) a reduction of HbA1c in the blood of the subject; and/or (v) a reduction in supplemental insulin usage by the subject. In some embodiments, an improvement in beta cell function is indicated by a reduction in blood glucose levels in the subject. In some embodiments, an improvement in beta cell function is indicated by an increase in C-peptide levels in the blood of the subject. In some embodiments, an improvement in beta cell function is indicated by an increase in C-peptide levels in the pancreas of the subject. In some embodiments, an improvement in beta cell function is indicated by a reduction of HbA1c in the blood of the subject. In some embodiments, an improvement in beta cell function is indicated by a reduction in supplemental insulin usage by the subject. In some embodiments, C-peptide is measured in a blood sample, a serum sample, a plasma sample, or a pancreatic sample.

In another aspect, the disclosure provides methods of preventing or slowing down progression of diabetes. In some embodiments, a method of preventing or slowing down progression of diabetes in a subject (e.g., a human) comprises administering to the subject a therapeutically effective amount of a GCGR antagonist and a therapeutically effective amount of an immunotherapeutic agent.

In another aspect, the disclosure provides methods of preserving beta cell function, methods of preventing or slowing down progression beta cell dysfunction, and methods of preventing or slowing down destruction of beta cells. In some embodiments, a method of preserving beta cell function in a subject (e.g., a human) comprises administering to a subject a therapeutically effective amount of a GCGR antagonist and a therapeutically effective amount of an immunotherapeutic agent. In some embodiments, a method of preventing or slowing down progression of beta cell dysfunction in a subject comprises administering to the subject a therapeutically effective amount of a GCGR antagonist and a therapeutically effective amount of an immunotherapeutic agent. In some embodiments, a method of preventing or slowing down destruction of beta cells in a subject (e.g., a human) comprises administering to the subject a therapeutically effective amount of a GCGR antagonist and a therapeutically effective amount of an immunotherapeutic agent. In some embodiments, beta cell dysfunction is evaluated by measuring (i) C-peptide levels in the blood of a subject; (ii) HbA1c levels in the blood of a subject; and/or (iii) supplemental insulin use by the subject. In some embodiments, beta cell dysfunction is evaluated by measuring C-peptide levels in the blood of the subject. In some embodiments, beta cell dysfunction is evaluated by measuring HbA1c levels in the blood of the subject. In some embodiments, beta cell dysfunction is evaluated by measuring supplemental insulin use by the subject.

In some embodiments of each of the aforementioned aspects, as well as other aspects and embodiments described elsewhere herein, the subject has newly diagnosed diabetes. In some embodiments of each of the aforementioned aspects, as well as other aspects and embodiments described elsewhere herein, the subject has newly diagnosed Type 1 diabetes. In some embodiments of each of the aforementioned aspects, as well as other aspects and embodiments described elsewhere herein, the subject has newly diagnosed Type 2 diabetes. In some embodiments of each of the aforementioned aspects, as well as other aspects and embodiments described elsewhere herein, the subject has newly diagnosed metabolic syndrome.

In some embodiments of each of the aforementioned aspects, as well as other aspects and embodiments described elsewhere herein, the GCGR antagonist is an antibody or a small molecule. In some embodiments, the GCGR antagonist is an antibody that specifically binds human GCGR. In some embodiments, the GCGR antagonist is an antibody that specifically binds the extracellular domain of human GCGR. In some embodiments, the GCGR antagonist is an antibody that comprises: (a) a heavy chain variable region CDR1 comprising GFTFTNHWLG (SEQ ID NO:6), a heavy chain variable region CDR2 comprising DIYPG- GYYINYNEKFKG (SEQ ID NO:7), and a heavy chain variable region CDR3 comprising HTNYGSDY (SEQ ID NO:8); and/or (b) a light chain variable region CDR1 comprising RSSQSIVDSYGNTFLE (SEQ ID NO:9), a light chain variable region CDR2 comprising KVSNRLS (SEQ ID NO:10), and a light chain variable region CDR3 comprising FQGSHVPWT (SEQ ID NO:11). In some embodiments, the GCGR antagonist is an antibody that comprises: (a) a heavy chain variable region CDR1 comprising GFTFTNHWLG (SEQ ID NO:6), a heavy chain variable region CDR2 comprising DIYPGGYYINYNEKFKG (SEQ ID NO:7), and a heavy chain variable region CDR3 comprising HTNYGSDY (SEQ ID NO:8); and (b) a light chain variable region CDR1 comprising RSSQSIVDSYGNTFLE (SEQ ID NO:9), a light chain variable region CDR2 comprising KVSNRLS (SEQ ID NO:10), and a light chain variable region CDR3 comprising FQGSHVPWT (SEQ ID NO:11). In some embodiments of the methods described herein, an anti-GCGR antibody comprises a heavy chain variable region comprising an amino acid sequence that has the three VH CDRs of antibody 6B5 and which has at least 75%, 80%, 85%, 90%, 95%, 96%, 97%, 98%, 99%, or 100% identity to the sequence set forth in SEQ ID NO:14 and a light chain variable region comprising an amino acid sequence that has the three VL CDRs of antibody 6B5 and which has at least 75%, 80%, 85%, 90%, 95%, 96%, 97%, 98%, 99%, or 100% identity to the sequence set forth in SEQ ID NO:15. In some embodiments, the GCGR antagonist is an antibody that comprises a heavy chain variable region having at least 90% sequence identity to SEQ ID NO:14. In some embodiments, the GCGR antagonist is an antibody that comprises a light chain variable region having at least 90% sequence identity to SEQ ID NO:15. In some embodiments, the GCGR antagonist is an antibody that comprises: (a) a heavy chain variable region having at least 90% sequence identity to SEQ ID NO:14; and/or (b) a light chain variable region having at least 90% sequence identity to SEQ ID NO:15. In some embodiments, the GCGR antagonist is an antibody that comprises a heavy chain variable region having at least 95% sequence identity to SEQ ID NO:14. In some embodiments, the GCGR antagonist is an antibody that comprises a light chain variable region having at least 95% sequence identity to SEQ ID NO:15. In some embodiments, the GCGR antagonist is an antibody that comprises: (a) a heavy chain variable region having at least 95% sequence identity to SEQ ID NO:14; and/or (b) a light chain variable region having at least 95% sequence identity to SEQ ID NO:15. In some embodiments, the GCGR antagonist is an antibody that comprises a heavy chain variable region comprising SEQ ID NO:14. In some embodiments, the GCGR antagonist is an antibody that comprises a light chain variable region comprising SEQ ID NO:15. In some embodiments, the GCGR antagonist is an antibody that comprises: (a) a heavy chain variable region comprising SEQ ID NO:14; and/or (b) a light chain variable region comprising SEQ ID NO:15. In some embodiments, the GCGR antagonist is an antibody that comprises a heavy chain variable region comprising SEQ ID NO:14 and a light chain variable region comprising SEQ ID NO:15. In some embodiments of the methods described herein, an anti-GCGR antibody comprises a heavy chain comprising an amino acid sequence that has the three VH CDRs of antibody 6B5 and which has at least 75%, 80%, 85%, 90%, 95%, 96%, 97%, 98%, 99%, or 100% identity to the sequence set forth in SEQ ID NO:79 and a light chain comprising an amino acid sequence that has the three VL CDRs of antibody 6B5 and which has at least 75%, 80%, 85%, 90%, 95%, 96%, 97%, 98%, 99%, or 100% identity to the sequence set forth in SEQ ID NO:81. In some embodiments, the GCGR antagonist is an antibody that comprises a heavy chain comprising SEQ ID NO:79. In some embodiments, the GCGR antagonist is an antibody that comprises a light chain comprising SEQ ID NO:81. In some embodiments, the GCGR antagonist is an antibody that comprises a heavy chain comprising SEQ ID NO:79 and a light chain comprising SEQ ID NO:81. In some embodiments, the GCGR antagonist is a humanized version of antibody 6B5. In some embodiments, the GCGR antagonist is antibody Hz6B5.

In certain embodiments of the methods described herein, the immunotherapeutic agent is an anti-CD3 antibody. In some instances, the anti-CD3 antibody has the six CDRs of any one of the following CD3 antibodies: Muromab, otelixizumab, teplizumab, visilizumab, foralumab, humanized M291, ELV-001, ES-301, and TRX-318. In some instances, the anti-CD3 antibody has the VH and VL of any one of the following CD3 antibodies: Muromab, otelixizumab, teplizumab, visilizumab, foralumab, humanized M291, ELV-001, ES-301, and TRX-318. In other instances, the anti-CD3 antibody has the heavy and light chain of any one of the following CD3 antibodies: Muromab, otelixizumab, teplizumab, visilizumab, foralumab, humanized M291, ELV-001, ES-301, and TRX-318. In some instances, the Fc region of the anti-CD3 antibody is from IgG1, IgG2, IgG2a, or IgG2b. In some cases, the Fc region comprises one or more of the following substitutions: N297A, N297Q, L234A, L235A, V234A, V237A, or V235E.

In some embodiments, the GCGR antagonist is a monoclonal antibody, a humanized antibody, a human antibody, a chimeric antibody, a bispecific antibody, a multispecific antibody, or an antibody fragment comprising at least one antigen-binding site. In some embodiments, the GCGR antagonist is an IgG antibody. In some embodiments, the GCGR antagonist is an IgG1 antibody, an IgG2 antibody, or an IgG4 antibody.

In some embodiments of each of the aforementioned aspects, as well as other aspects and embodiments described elsewhere herein, the GCGR antagonist enhances the activity of the immunotherapeutic agent. In some embodiments of each of the aforementioned aspects, as well as other aspects and embodiments described elsewhere herein, the immunotherapeutic agent enhances the activity of the GCGR antagonist. In some embodiments of each of the aforementioned aspects, as well as other aspects and embodiments described elsewhere herein, the GCGR antagonist and the immunotherapeutic agent act synergistically.

In some embodiments of each of the aforementioned aspects, as well as other aspects and embodiments described elsewhere herein, the immunotherapeutic agent is an immunomodulator. In some embodiments, the immunotherapeutic agent is an immunomodulator that inhibits, suppresses, or reduces an immune response. In some embodiments, the immunotherapeutic agent is an immunosuppressive agent. In some embodiments, the immunotherapeutic agent is selected from the group consisting of: an anti-CD3 antibody, an anti-CD20 antibody, an anti-CD28 antibody, a CTLA4-Ig fusion protein, an IL-1β inhibitor (e.g., an anti-IL-1β antibody), an IL-1R inhibitor (e.g., an anti-IL-1R antibody), an IL-2R inhibitor (e.g., an anti-IL-2R antibody), an IL-2 derivative or mutein, an IL-6 inhibitor (e.g., an anti-IL-6 antibody), an IL-6R inhibitor (e.g., an anti-IL-6R antibody), an IL-17 inhibitor (e.g., an anti-IL-17 antibody or anti-IL-17R antibody), an IL-21 inhibitor (e.g., an anti-IL-21 antibody), and a TNFα inhibitor (e.g., an anti-TNF antibody). In some embodiments, the immunotherapeutic agent is an anti-CD3 antibody (e.g., Muromab, otelixizumab, teplizumab, visilizumab, foralumab, humanized M291, ELV-001, ES-301, TRX-318).

In some embodiments of each of the aforementioned aspects, as well as other aspects and embodiments described elsewhere herein, the GCGR antagonist is an anti-GCGR antibody described herein and the immunotherapeutic agent is an anti-CD3 antibody. In some embodiments of the methods, the GCGR antagonist is a humanized version of antibody 6B5 and the immunotherapeutic agent is an anti-CD3 antibody. In some embodiments of the methods, the GCGR antagonist is antibody Hz6B5 and the immunotherapeutic agent is an anti-CD3 antibody (e.g., Muromab, otelixizumab, teplizumab, visilizumab, foralumab, humanized M291, ELV-001, ES-301, TRX-318).

In some embodiments of each of the aforementioned aspects, as well as other aspects and embodiments described elsewhere herein, a method comprises administering at least one additional therapeutic agent to the subject (e.g., human). In some embodiments, the at least one additional therapeutic agent is a diabetes or hyperglycemia drug. In some embodiments, the diabetes or hyperglycemia drug is a biguanide, a sulfonylurea, a meglitinide derivative, an alpha-glucosidase inhibitor, a thiazolidinedione (TZDs), a glucagon-like peptide-1 (GLP-1) agonist, a dipeptidyl peptidase 4 (DPP-4) inhibitor, a selective sodium-glucose transporter-2 (SGLT-2) inhibitor, an insulin or insulin mimetic, an amylinomimetic, a bile acid sequestrant, and/or a dopamine agonist. In some embodiments, the at least one additional therapeutic agent is an obesity drug, an appetite suppressant, or a weight loss drug.

In some embodiments of each of the aforementioned aspects, as well as other aspects and embodiments described elsewhere herein, the subject (e.g., human) receives at least one daily dosage of supplemental insulin. In some embodiments, a method of treatment reduces supplemental insulin use by the subject.

When aspects or embodiments of the disclosure are described in terms of a Markush group or other grouping of alternatives, the present disclosure encompasses not only the entire group listed as a whole, but also each member of the group individually and all possible subgroups of the main group, and also the main group absent one or more of the group members. The present disclosure also envisages the explicit exclusion of one or more of any of the group members in the claimed invention.

DETAILED DESCRIPTION

Figure 1:
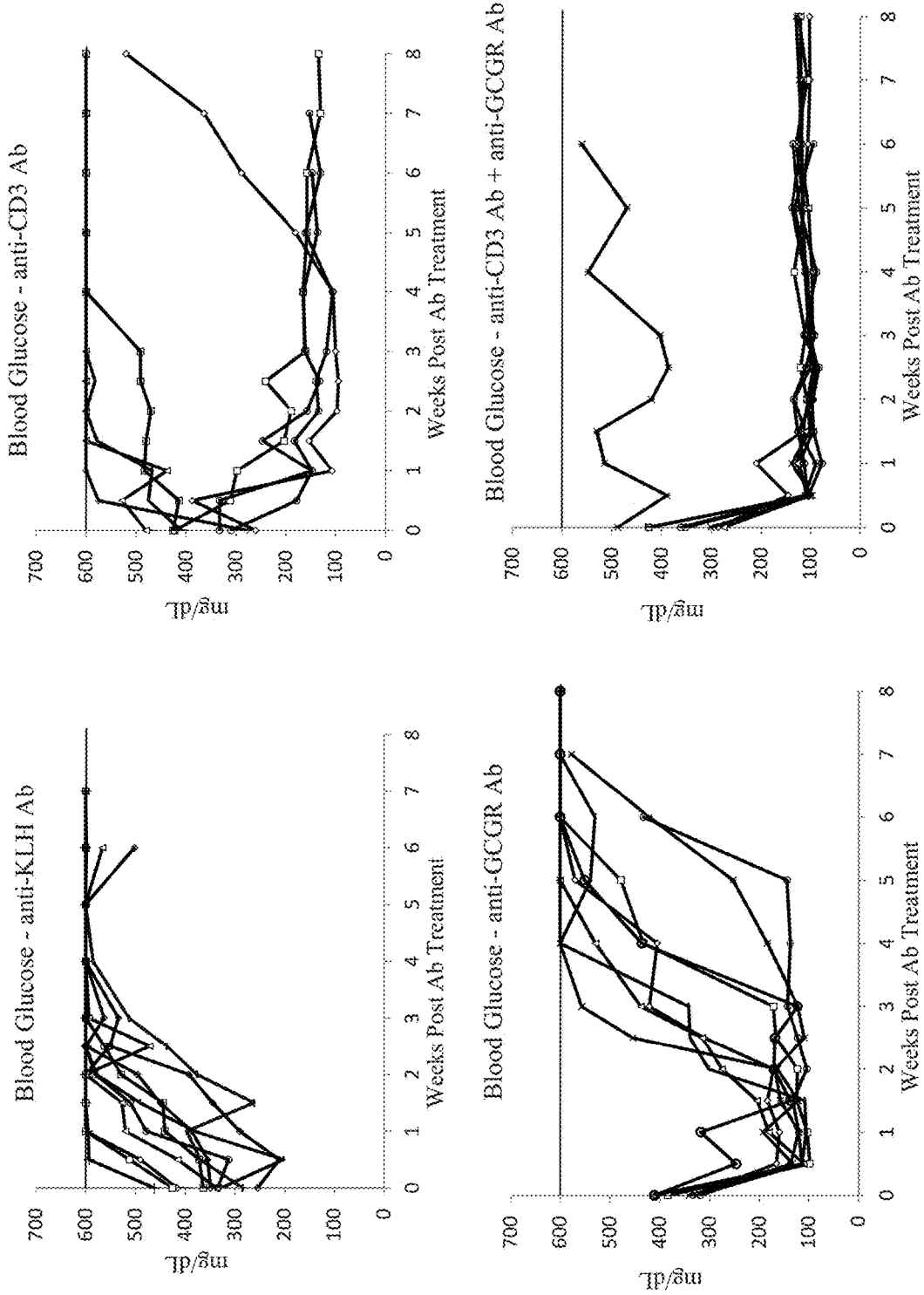
FIG. 1. Blood glucose levels in mice after treatment with an anti-GCGR antibody, an anti-CD3 antibody, a combination of an anti-GCGR antibody and an anti-CD3 antibody, and a control antibody.

The present disclosure provides methods of treating diseases, disorders, and/or conditions associated with beta cell dysfunction, for example, diabetes and/or metabolic syndrome. The methods provided herein comprise administering to a subject (e.g., a human) a therapeutically effective amount of a glucagon receptor (GCGR) antagonist in combination with a therapeutically effective amount of an immunotherapeutic agent.

I. Definitions

Unless otherwise defined herein, technical and scientific terms used in the present disclosure have the meanings that are commonly understood by those of ordinary skill in the art. For purposes of interpreting this specification, the following description of terms will apply and whenever appropriate, terms used in the singular will also include the plural and vice versa.

The terms "antagonist" and antagonistic" as used herein refer to any molecule that partially or fully blocks, inhibits, reduces, or neutralizes a biological activity of a target and/or signaling pathway. The term "antagonist" as used herein includes any molecule that partially or fully blocks, inhibits, reduces, or neutralizes the activity of a protein. Suitable antagonist molecules include, but are not limited to, antagonist antibodies, soluble receptors, and small molecules.

The term "binding agent" as used herein refers to a molecule that binds a specific antigen or target (e.g., GCGR). A binding agent may comprise a protein, peptide, nucleic acid, carbohydrate, lipid, or small molecular weight compound. In some embodiments, a binding agent comprises a binding protein. In some embodiments, a binding agent is a binding protein. In some embodiments, a binding agent comprises an antibody. In some embodiments, a binding agent is an antibody. In some embodiments, a binding agent comprises an alternative protein scaffold or artificial scaffold and an antigen-binding site. In some embodiments, a binding agent is a fusion protein comprising an antigen-binding site. In some embodiments, a binding agent is a bispecific or multispecific molecule comprising at least one antigen-binding site.

The term "antibody" as used herein refers to an immunoglobulin molecule that recognizes and binds a target through at least one antigen-binding site. "Antibody" is used herein in the broadest sense and encompasses various antibody structures and formats, including but not limited to, polyclonal antibodies, recombinant antibodies, monoclonal antibodies, chimeric antibodies, humanized antibodies, human antibodies, bispecific antibodies, multispecific antibodies, diabodies, tribodies, tetrabodies, single chain Fv (scFv) antibodies, single domain antibodies (e.g., camelid/llama antibodies), and antibody fragments.

The term "intact antibody" or "full-length antibody" refers to an antibody having a structure substantially similar to a native antibody structure. This includes an antibody comprising two light chains each comprising a variable region (VL) and a light chain constant region (CL) and two heavy chains each comprising a variable region (VH) and at least heavy chain constant regions CH1, CH2, and CH3, and a hinge region between CH1 and CH2 regions.

The term "antibody fragment" as used herein refers to a molecule other than an intact antibody that comprises a portion of an antibody and generally at least one antigen-binding site. Examples of antibody fragments include, but are not limited to, Fab, Fab', F(ab')2, Fv, disulfide-linked Fv (sdFv), Fd, linear antibodies, single chain antibody molecules (e.g., scFv, sc(Fv)$_2$), diabodies, tribodies, tetrabodies, minibodies, dual variable domain antibodies (DVD), single variable domain antibodies, and multispecific molecules formed from antibody fragments.

The term "variable region" as used herein refers to the region of an antibody light chain or the region of an antibody heavy chain that is involved in binding the antibody to antigen. The variable regions of an antibody heavy chain and an antibody light chain have similar structures, and generally comprise four framework regions and three complementarity determining regions (CDRs) (also known as hypervariable regions).

The term "framework regions" refers to amino acid residues other than the CDR residues within a variable region. The variable region generally comprises four framework regions, FR1, FR2, FR3, and FR4.

The term "monoclonal antibody" as used herein refers to a substantially homogenous antibody population involved in the highly specific recognition and binding of a single antigenic determinant or epitope. The term "monoclonal antibody" encompasses intact and full-length monoclonal antibodies as well as antibody fragments (e.g., Fab, Fab', F(ab')2, Fv), single chain (scFv) antibodies, fusion proteins comprising an antibody fragment, and any other modified immunoglobulin molecule comprising an antigen-binding site. Furthermore, the term "monoclonal antibody" refers to such antibodies made by any number of techniques, including but not limited to, hybridoma production, phage library display, recombinant expression, and transgenic animals.

The term "chimeric antibody" as used herein refers to an antibody in which a portion of the heavy and/or light chain is derived from a particular source or species, while the remainder of the heavy and/or light chain is derived from a different source or species.

The term "humanized antibody" as used herein refers to an antibody that generally comprises human immunoglobulins (e.g., heavy chains and light chains) in which the native CDR residues are replaced by residues of corresponding CDRs from a nonhuman species such as mouse, rat, rabbit, or nonhuman primate, wherein the nonhuman antibody has the desired specificity, affinity, and/or activity. In some instances, one or more residues within one or more framework regions of the human immunoglobulin are replaced by corresponding residues from the nonhuman antibody. Furthermore, humanized antibodies can comprise residues that are not found in the nonhuman antibody or in the human antibody backbone. These modifications may be made to further refine and/or optimize antibody characteristics. A humanized antibody may comprise variable regions containing all or substantially all of the CDRs that correspond to those of a nonhuman immunoglobulin and all or substantially all of the framework regions that correspond to those of a human immunoglobulin. In some embodiments, the humanized antibody will comprise at least a portion of an immunoglobulin Fc region (e.g., hinge region, CH1, CH2, and/or CH3), typically that of a human immunoglobulin.

The term "human antibody" as used herein refers to an antibody that possesses an amino acid sequence that corresponds to an antibody produced by a human and/or an antibody that has been made using any of the techniques that are known to those of skill in the art for making human antibodies. These techniques include, but not limited to, phage display libraries, yeast display libraries, transgenic animals, and B-cell hybridoma technology. A human antibody as defined herein excludes a humanized antibody comprising residues from a nonhuman source.

The terms "epitope" and "antigenic determinant" are used interchangeably herein and refer to the portion of an antigen or target capable of being recognized and bound by a particular binding agent or binding protein (e.g., an antibody). When the antigen or target is a polypeptide, epitopes can be formed both from contiguous amino acids and noncontiguous amino acids juxtaposed by tertiary folding of the protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5, 6, 7, or 8-10 amino acids in a unique spatial conformation. Epitopes can be predicted using any one of a large number of software bioinformatic tools that are publicly available to those of skill in the art. An epitope on a target protein can be characterized using X-ray crystallography to analyze the amino acid residue interactions of an antigen/antibody complex.

The term "specifically binds" as used herein refers to a binding agent (e.g., an antibody) that interacts more frequently, more rapidly, with greater duration, with greater affinity, or with some combination of the above to a particular antigen, epitope, protein, or target molecule than with alternative substances. In some embodiments, a protein (e.g., an antibody) that specifically binds an antigen (e.g., human GCGR) may bind related antigens (e.g., cyno GCGR). An antibody that specifically binds an antigen can be identified, for example, by immunoassays, ELISAs, surface plasmon resonance (SPR; e.g., Biacore), FACS, or other techniques known to those of ordinary skill in the art.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification. Also included within the definition are, for example, polypeptides containing one or more analogs of an amino acid, including but not limited to, unnatural amino acids, as well as other modifications known in the art. It is understood that, because the polypeptides of this disclosure may be based upon antibodies, the term "polypeptide" encompasses polypeptides as a single chain and polypeptides of two or more associated chains.

The terms "polynucleotide" and "nucleic acid" and "nucleic acid molecule" are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art and many are publicly available. These include, but are not limited to, BLAST, ALIGN, Megalign, BestFit, GCG Wisconsin Package, and variants thereof. In some embodiments, two polynucleotides or polypeptides of the disclosure are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 40-60 nucleotides or amino acid residues, at least about 60-80 nucleotides or amino acid residues in length, or any integral value there between. In some embodiments, identity exists over a longer region than 60-80 nucleotides or amino acid residues, such as at least about 80-100 nucleotides or amino acid residues, and in some embodiments the sequences are substantially identical over the full length of the sequences being compared, for example, (i) the coding region of a nucleotide sequence or (ii) an amino acid sequence.

The phrase "conservative amino acid substitution" as used herein refers to a substitution in which one amino acid residue is replaced with another amino acid residue having a similar side chain. Families of amino acid residues having similar side chains have been generally defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is considered to be a conservative substitution. Generally, conservative substitutions in the sequences of polypeptides and/or antibodies do not abrogate the binding of the polypeptide or antibody to the target binding site. Methods of identifying nucleotide and amino acid conservative substitutions that do not eliminate binding are well-known in the art.

The term "vector" as used herein means a construct that is capable of delivering, and usually expressing, one or more gene(s) or sequence(s) of interest in a host cell. Examples of vectors include, but are not limited to, viral vectors, naked DNA or RNA expression vectors, plasmid, cosmid, or phage vectors, DNA or RNA expression vectors associated with cationic condensing agents, and DNA or RNA expression vectors encapsulated in liposomes.

The term "isolated" as used herein refers to a polypeptide, soluble protein, antibody, polynucleotide, vector, cell, or composition that is in a form not found in nature. An "isolated" antibody is substantially free of material from the cellular source from which it is derived. In some embodiments, isolated polypeptides, soluble proteins, antibodies, polynucleotides, vectors, cells, or compositions are those which have been purified to a degree that they are no longer in a form in which they are found in nature. In some embodiments, a polypeptide, soluble protein, antibody, polynucleotide, vector, cell, or composition that is isolated is substantially pure. A polypeptide, soluble protein, antibody, polynucleotide, vector, cell, or composition may be isolated from a natural source or from a source such as an engineered cell line.

The term "substantially pure" as used herein refers to material that is at least 50% pure (i.e., free from contaminants), at least 90% pure, at least 95% pure, at least 98% pure, or at least 99% pure.

The term "subject" refers to any animal (e.g., a mammal), including, but not limited to, humans, non-human primates, canines, felines, rabbits, rodents, and the like, which is to be the recipient of a treatment or therapy.

The term "pharmaceutically acceptable" as used herein refers to a substance approved or approvable by a regulatory agency or listed in the U.S. Pharmacopeia, European Pharmacopeia, or other generally recognized pharmacopeia for use in animals, including humans.

The terms "pharmaceutically acceptable excipient, carrier, or adjuvant" or "acceptable pharmaceutical carrier" as used herein refer to an excipient, carrier, or adjuvant that can be administered to a subject, together with at least one therapeutic agent (e.g., an antibody), and which does not have an effect on the pharmacological activity of the therapeutic agent. In general, those of skill in the art and the U.S. FDA consider a pharmaceutically acceptable excipient, carrier, or adjuvant to be an inactive ingredient of any formulation.

The term "pharmaceutical formulation" or "pharmaceutical composition" as used herein refers to a preparation that is in such form as to permit the biological activity of the agent (e.g., an antibody) to be effective. A pharmaceutical formulation or composition generally comprises additional components, such as a pharmaceutically acceptable excipient, carrier, adjuvant, buffer, etc.

The term "effective amount" or "therapeutically effective amount" as used herein refers to the amount of a therapeutic agent (e.g., an antibody) which is sufficient to reduce and/or ameliorate the severity and/or duration of a disease, disorder, or condition and/or a symptom in a subject. The term also encompasses an amount of a therapeutic agent necessary for the (i) reduction or amelioration of the advancement or progression of a given disease, disorder, or condition, (ii) reduction or amelioration of the recurrence, development, or onset of a given disease, disorder, or condition, and/or (iii) the improvement or enhancement of the prophylactic or therapeutic effect(s) of another agent or therapy (e.g., an agent other than the therapeutic agents provided herein).

The term "therapeutic effect" as used herein refers to the effect and/or ability of a therapeutic agent (e.g., an antibody) to reduce and/or ameliorate the severity and/or duration of a disease, disorder, or condition and/or a symptom in a subject. The term also encompasses the ability of a therapeutic agent to (i) reduce or ameliorate the advancement or progression of a given disease, disorder, or condition, (ii) reduce or ameliorate the recurrence, development, or onset of a given disease, disorder, or condition, and/or (iii) to improve or enhance the prophylactic or therapeutic effect(s) of another agent or therapy (e.g., an agent other than the therapeutic agents provided herein).

The term "treat" or "treatment" or "treating" or "to treat" or "alleviate" or "alleviation" or "alleviating" or "to alleviate" as used herein refers to both (1) therapeutic measures that aim to cure, slow down, lessen symptoms of, and/or halt progression of a pathologic condition or disorder and (2) prophylactic or preventative measures that aim to prevent or slow down the development of a targeted pathologic condition or disorder. Thus, those in need of treatment include those already with the disorder, those at risk of having/developing the disorder, and those in whom the disorder is to be prevented.

The term "prevent" or "prevention" or "preventing" as used herein refers to the partial or total inhibition of the development, recurrence, onset, or spread of a disease, disorder, or condition, or a symptom thereof in a subject.

As used herein, reference to "about" or "approximately" a value or parameter includes (and describes) embodiments that are directed to that value or parameter. For example, a description referring to "about X" includes description of "X". About X" means+/−10% of X. So, "about 10" means a value from 9 to 11.

As used in the present disclosure and claims, the singular forms "a", "an" and "the" include plural forms unless the context clearly dictates otherwise.

It is understood that wherever embodiments are described herein with the term "comprising" otherwise analogous embodiments described in terms of "consisting of" and/or "consisting essentially of" are also provided. It is also understood that wherever embodiments are described herein with the phrase "consisting essentially of" otherwise analogous embodiments described in terms of "consisting of" are also provided.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Methods of Use and Pharmaceutical Compositions

A GCGR antagonist (e.g., an anti-GCGR antibody) in combination with an immunotherapeutic agent is useful in a variety of applications including, but not limited to, therapeutic treatment methods, such as the treatment of diabetes. The combination can be used to lower blood glucose levels in a subject (e.g., human) in need thereof. In certain embodiments, the combination of a GCGR antagonist (e.g., an anti-GCGR antibody) with an immunotherapeutic agent is useful for reducing, inhibiting, suppressing, and/or preventing an immune response, (e.g., an immune response targeting the beta cells of the pancreas). The methods of use may be in vitro, ex vivo, or in vivo methods.

In some embodiments, a GCGR antagonist (e.g., an anti-GCGR antibody) in combination with an immunotherapeutic agent is administered to a human. In some embodiments, a GCGR antagonist (e.g., an anti-GCGR antibody) in combination with an immunotherapeutic agent is administered to a non-human mammal (e.g., a primate, dog, cat, pig, rat, or mouse). In some embodiments, a GCGR antagonist (e.g., an anti-GCGR antibody) in combination with an immunotherapeutic agent is administered to a non-human mammal for veterinary purposes or for testing in an animal model of human disease. In some embodiments, animal models are useful for evaluating the therapeutic efficacy of a GCGR antagonist (e.g., an anti-GCGR antibody) in combination with an immunotherapeutic agent (e.g., testing of dosages and/or time courses of administration).

In some embodiments, a GCGR antagonist (e.g., an anti-GCGR antibody) in combination with an immunotherapeutic agent is useful in methods for inhibiting GCGR activity. In some embodiments, a GCGR antagonist (e.g., an anti-GCGR antibody) in combination with an immunotherapeutic agent is useful in methods for inhibiting glucagon activity. In some embodiments, a GCGR antagonist (e.g., an anti-GCGR antibody) in combination with an immunotherapeutic agent is useful in methods for reducing or lowering blood glucose levels. In some embodiments, a GCGR antagonist (e.g., an anti-GCGR antibody) in combination with an immunotherapeutic agent is useful in methods for increasing blood C-peptide levels. In some embodiments, a GCGR antagonist (e.g., an anti-GCGR antibody) in combination with an immunotherapeutic agent is useful in methods for increasing blood insulin levels (e.g., endogenous insulin). In some embodiments, a GCGR antagonist (e.g., an anti-GCGR antibody) in combination with an immunotherapeutic agent is useful in methods for increasing pancreatic levels of insulin. In some embodiments, a GCGR antagonist (e.g., an anti-GCGR antibody) in combination with an immunotherapeutic agent is useful in methods of reducing beta cell dysfunction. In some embodiments, a GCGR antagonist (e.g., an anti-GCGR antibody) in combination with an immunotherapeutic agent is useful in methods of reducing destruction of beta cells. In some embodiments, a GCGR antagonist (e.g., an anti-GCGR antibody) in combination with an immunotherapeutic agent is useful in methods of enhancing or increasing the activity of regulatory T-cells (Tregs). In some embodiments, a GCGR antagonist (e.g., an anti-GCGR antibody) in combination with an immunotherapeutic agent is useful in methods of enhancing or increasing the activity of macrophage-derived suppressor cells (MDSCs). In some instances, the terms "inhibiting", "reducing", "increasing", "enhancing" are relative to levels/activity in the absence of treatment with the combination. In some instances, the terms "inhibiting", "reducing", "increasing", "enhancing" are relative to levels/activity prior to treatment with the combination. In some instances, the terms "inhibiting", "reducing", "increasing", "enhancing" are relative to a "control level/activity" for subjects who do not have diabetes.

In some embodiments, a GCGR antagonist enhances the activity of an immunotherapeutic agent. In some embodiments, a GCGR antagonist enhances the activity of an immunotherapeutic agent as compared to the activity of the immunotherapeutic agent when administered as a single agent. In some embodiments, an immunotherapeutic agent enhances the activity of a GCGR antagonist as compared to the activity of the GCGR antagonist when administered as a single agent. In some embodiments, a GCGR antagonist and an immunotherapeutic agent act synergistically.

There are several different types of diabetes that are referred to in a number of ways, including but not limited to, autoimmune diabetes, Type 1 diabetes, juvenile diabetes, latent autoimmune diabetes of adults, insulin-dependent diabetes, Type 2 diabetes, insulin-independent diabetes, and gestational diabetes. Type 1 diabetes an autoimmune disease condition characterized by high blood glucose levels resulting from a loss of pancreatic beta cell mass and/or function and a loss of insulin production. Type 1 diabetes symptoms are generally the result of hyperglycemia and a breakdown of body fat. Symptoms include, but are not limited to, excessive thirst (polydipsia), frequent urination (polyuria), extreme hunger (polyphagia), extreme fatigue, weight loss, and ketones present in their urine. Type 1 diabetes develops in children (e.g., juvenile diabetes; early onset diabetes) and adults (e.g., latent autoimmune diabetes of adults (LADA)), thus people can be diagnosed at any age. With a typically quick onset, Type 1 diabetes must be managed with the use of supplemental insulin—either via injection or use of an insulin pump. In contrast, generally, Type 2 diabetes results from insulin resistance and/or reduced insulin secretion. However, many subjects with Type 2 diabetes also have significantly reduced pancreatic beta cell mass and/or function that ultimately results in an insulin deficiency. Symptoms of Type 2 diabetes include, but are not limited to, hyperglycemia, fatigue, dry or itchy skin, blurred vision, increased thirst, frequent urination, slow healing cuts or sores, high rate of infections, and numbness or tingling in the feet. If a diabetic condition is left untreated more serious symptoms can result, including severe hyperglycemia (e.g., glucose levels over 600 mg/dL), lethargy, confusion, shock, and/or a hyperosmolar hyperglycemic non-ketotic coma.

In some embodiments, a method of treating diabetes in a subject (e.g., a human) comprises administering to the subject a therapeutically effective amount of a GCGR antagonist and a therapeutically effective amount of an immunotherapeutic agent. In some embodiments, a method of treating diabetes comprises administering to the subject a therapeutically effective amount of a GCGR antagonist and a therapeutically effective amount of an immunotherapeutic agent, wherein the GCGR antagonist is an antibody that specifically binds GCGR (e.g., an anti-GCGR antibody described herein). In some embodiments, a method of treating diabetes comprises administering to the subject a therapeutically effective amount of a GCGR antagonist and a therapeutically effective amount of an immunotherapeutic agent, wherein the GCGR antagonist is an antibody that specifically binds GCGR (e.g., an anti-GCGR antibody described herein) and wherein the immunotherapeutic agent is an immunosuppressive agent. In some embodiments, the GCGR antagonist is a humanized version of antibody 6B5 and the immunotherapeutic agent is an immunosuppressive agent (e.g., azathioprine, mycophenolate mofetil, or cyclosporine). In some embodiments, the GCGR antagonist is a humanized version of antibody 6B5 and the immunotherapeutic agent is an anti-CD3 antibody (e.g., Muromab, otelixizumab, teplizumab, visilizumab, foralumab, humanized M291). In some embodiments, the GCGR antagonist is a humanized version of antibody 6B5 and the immunotherapeutic agent is an IL-1 inhibitor (e.g., an anti-IL-1β antibody, an anti-IL-1α antibody, or an anti-IL-1R antibody). In some embodiments, the GCGR antagonist is a humanized version of antibody 6B5 and the immunotherapeutic agent is an anti-CD20 antibody (e.g., rituximab (RITUXAN)). In some embodiments, the GCGR antagonist is a humanized version of antibody 6B5 and the immunotherapeutic agent is an IL-6 inhibitor (e.g., an anti-IL-6 antibody or an anti-IL-6R antibody). In some embodiments, the GCGR antagonist is a humanized version of antibody 6B5 and the immunotherapeutic agent is an IL-17 inhibitor (e.g., an anti-IL17 antibody or an anti-IL-17 antibody). In some embodiments, the subject is human. In some embodiments, the diabetes is prediabetes. In some embodiments, the diabetes is autoimmune diabetes. In some embodiments, the diabetes is Type 1 diabetes. In some embodiments, the Type 1 diabetes is latent autoimmune diabetes of adults (LADA). In some embodiments, the Type 1 diabetes is juvenile diabetes. In some embodiments, the diabetes is Type 2 diabetes. In some embodiments, the diabetes is insulin-dependent diabetes. In some embodiments, the diabetes is non-insulin-dependent diabetes or insulin-independent diabetes.

In some embodiments, a method of reducing or lowering blood glucose levels in a subject (e.g., a human) comprises administering to the subject a therapeutically effective amount of a GCGR antagonist and a therapeutically effective amount of an immunotherapeutic agent. In some instances, the method reduces or lowers blood glucose levels relative to levels prior to treatment with the combination. Reduction of blood glucose levels in a subject may be needed when the blood glucose levels are higher than a glucose level that is considered normal by those of skill in the art. Fasting blood glucose levels are considered to be in a "normal" range at less than about 100 mg/dL, blood glucose levels between about 100 and 126 mg/dL are considered to signal impaired glucose metabolism, and blood glucose levels greater than about 126 mg/dL are considered to be dangerous and a sign of glucose metabolism dysfunction. In some embodiments, the blood glucose level in a subject is reduced to a normal range. In some embodiments, the blood glucose level in a subject is reduced as compared to the blood glucose level in the subject prior to administration of the GCGR antagonist and immunotherapeutic agent. In some embodiments, a method of reducing or lowering blood glucose levels in a subject comprises administering to the subject a therapeutically effective amount of a GCGR antagonist and a therapeutically effective amount of an immunotherapeutic agent, wherein the GCGR antagonist is an antibody that specifically binds GCGR (e.g., an anti-GCGR antibody described herein). In some embodiments, a method of reducing or lowering blood glucose levels in a subject comprises administering to the subject a therapeutically effective amount of a GCGR antagonist and a therapeutically effective amount of an immunotherapeutic agent, wherein the GCGR antagonist is an antibody that specifically binds GCGR (e.g., an anti-GCGR antibody described herein) and wherein the immunotherapeutic agent is an immunosuppressive agent. In some embodiments, the GCGR antagonist is a humanized version of antibody 6B5 and the immunotherapeutic agent is an immunosuppressive agent (e.g., azathioprine, mycophenolate mofetil, or cyclosporine). In some embodiments, the GCGR antagonist is a humanized version of antibody 6B5 and the immunotherapeutic agent is an anti-CD3 antibody (e.g., Muromab, otelixizumab, teplizumab, visilizumab, foralumab, humanized M291). In some embodiments, the GCGR antagonist is a humanized version of antibody 6B5 and the immunotherapeutic agent is an IL-1 inhibitor (e.g., an anti-IL-1β antibody, an anti-IL-1α antibody, or an anti-IL-1R antibody). In some embodiments, the GCGR antagonist is a humanized version of antibody 6B5 and the immunotherapeutic agent is an anti-CD20 antibody (e.g., rituximab (RITUXAN)). In some embodiments, the GCGR antagonist is a humanized version of antibody 6B5 and the immunotherapeutic agent is an IL-6 inhibitor (e.g., an anti-IL-6 antibody or an anti-IL-6R antibody). In some embodiments, the GCGR antagonist is a humanized version of antibody 6B5 and the immunotherapeutic agent is an IL-17 inhibitor (e.g., an anti-IL17 antibody or an anti-IL-17 antibody). In some embodiments, the subject is human.

C-peptide is a widely used measure of pancreatic beta cell function (see, e.g., Leighton et al., 2017, Diabetes Therapy, 8:475-487). After cleavage of proinsulin, insulin and the 31-amino acid carboxyl peptide, "C-peptide" are produced in equal amounts. Measuring C-peptide is more reliable than measuring insulin, and in insulin-treated patient with diabetes, the measurement of C-peptide avoids the cross-reaction of exogenous and endogenous insulin in the assay. Furthermore, a C-peptide test can be done to help distinguish between Type 1 diabetes and Type 2 diabetes. A person whose pancreas does not make any insulin (Type 1 diabetes) has a low level of insulin and C-peptide. A person with Type 2 diabetes can have a normal or high level of C-peptide. The C-peptide level in plasma from fasting individuals is considered to be in a "normal" reference range of 0.5-2.7 ng/mL or 0.17-0.9 nmol/L.

In some embodiments, a method of increasing C-peptide levels in the blood of a subject (e.g., a human) comprises administering to the subject a therapeutically effective amount of a GCGR antagonist and a therapeutically effective amount of an immunotherapeutic agent. In some instances, the method increases C-peptide levels relative to levels prior to treatment with the combination. In some embodiments, a method of increasing C-peptide levels in a subject comprises administering to the subject a therapeutically effective amount of a GCGR antagonist and a therapeutically effective amount of an immunotherapeutic agent, wherein the GCGR antagonist is an antibody that specifically binds GCGR (e.g., an anti-GCGR antibody described herein). In some embodiments, a method of increasing C-peptide levels in a subject comprises administering to the subject a therapeutically effective amount of a GCGR antagonist and a therapeutically effective amount of an immunotherapeutic agent, wherein the GCGR antagonist is an antibody that specifically binds GCGR (e.g., an anti-GCGR antibody described herein) and wherein the immunotherapeutic agent is an immunosuppressive agent. In some embodiments, the GCGR antagonist is a humanized version of antibody 6B5 and the immunotherapeutic agent is an immunosuppressive agent (e.g., azathioprine, mycophenolate mofetil, or cyclosporine). In some embodiments, the GCGR antagonist is a humanized version of antibody 6B5 and the immunotherapeutic agent is an anti-CD3 antibody (e.g., Muromab, otelixizumab, teplizumab, visilizumab, foralumab, humanized M291). In some embodiments, the GCGR antagonist is a humanized version of antibody 6B5 and the immunotherapeutic agent is an IL-1 inhibitor (e.g., an anti-IL-1β antibody, an anti-IL-1α antibody, or an anti-IL-1R antibody). In some embodiments, the GCGR antagonist is a humanized version of antibody 6B5 and the immunotherapeutic agent is an anti-CD20 antibody (e.g., rituximab (RITUXAN)). In some embodiments, the GCGR antagonist is a humanized version of antibody 6B5 and the immunotherapeutic agent is an IL-6 inhibitor (e.g., an anti-IL-6 antibody or an anti-IL-6R antibody). In some embodiments, the GCGR antagonist is a humanized version of antibody 6B5 and the immunotherapeutic agent is an IL-17 inhibitor (e.g., an anti-IL17 antibody or an anti-IL-17 antibody). In some embodiments, the subject is human.

In some embodiments, a method of increasing insulin (e.g., endogenous insulin) levels in the blood of a subject (e.g., a human) comprises administering to the subject a therapeutically effective amount of a GCGR antagonist and a therapeutically effective amount of an immunotherapeutic agent. In some instances, the method increases insulin levels in the blood relative to levels prior to treatment with the combination. In some embodiments, a method of increasing insulin (e.g., endogenous insulin) levels in a subject comprises administering to the subject a therapeutically effective amount of a GCGR antagonist and a therapeutically effective amount of an immunotherapeutic agent, wherein the GCGR antagonist is an antibody that specifically binds GCGR (e.g., an anti-GCGR antibody described herein). In some embodiments, a method of increasing insulin (e.g., endogenous insulin) levels in a subject comprises administering to the subject a therapeutically effective amount of a GCGR antagonist and a therapeutically effective amount of an immunotherapeutic agent, wherein the GCGR antagonist is an antibody that specifically binds GCGR (e.g., an anti-GCGR antibody described herein) and wherein the immunotherapeutic agent is an immunosuppressive agent. In some embodiments, the GCGR antagonist is a humanized version of antibody 6B5 and the immunotherapeutic agent is an immunosuppressive agent (e.g., azathioprine, mycophenolate mofetil, or cyclosporine). In some embodiments, the GCGR antagonist is a humanized version of antibody 6B5 and the immunotherapeutic agent is an anti-CD3 antibody (e.g., Muromab, otelixizumab, teplizumab, visilizumab, foralumab, humanized M291). In some embodiments, the GCGR antagonist is a humanized version of antibody 6B5 and the immunotherapeutic agent is an IL-1 inhibitor (e.g., an anti-IL-1β antibody, an anti-IL-1α antibody, or an anti-IL-1R antibody). In some embodiments, the GCGR antagonist is a humanized version of antibody 6B5 and the immunotherapeutic agent is an anti-CD20 antibody (e.g., rituximab (RITUXAN)). In some embodiments, the GCGR antagonist is a humanized version of antibody 6B5 and the immunotherapeutic agent is an IL-6 inhibitor (e.g., an anti-IL-6 antibody or an anti-IL-6R antibody). In some embodiments, the GCGR antagonist is a humanized version of antibody 6B5 and the immunotherapeutic agent is an IL-17 inhibitor (e.g., an anti-IL17 antibody or an anti-IL-17 antibody). In some embodiments, the subject is human.

As used herein, the term "hyperglycemia" refers to a transient or chronic abnormally high level of glucose in the blood of a subject. Hyperglycemia may be caused by a delay in glucose metabolism or absorption such that the subject exhibits glucose intolerance or a state of elevated glucose not typically found in normal subjects. Fasting blood glucose levels are considered to be in a "normal" range at less than about 100 mg/dL, for impaired glucose metabolism (e.g., pre-diabetes), between about 100 and 126 mg/dL, and for diabetics greater than about 126 mg/dL.

In some embodiments, a method of treating hyperglycemia in a subject (e.g., a human) comprises administering to the subject a therapeutically effective amount of a GCGR antagonist and a therapeutically effective amount of an immunotherapeutic agent. In some embodiments, a method of treating hyperglycemia in a subject comprises administering to the subject a therapeutically effective amount of a GCGR antagonist and a therapeutically effective amount of an immunotherapeutic agent, wherein the GCGR antagonist is an antibody that specifically binds GCGR (e.g., an anti-GCGR antibody described herein). In some embodiments, a method of treating hyperglycemia in a subject comprises administering to the subject a therapeutically effective amount of a GCGR antagonist and a therapeutically effective amount of an immunotherapeutic agent, wherein the GCGR antagonist is an antibody that specifically binds GCGR (e.g., an anti-GCGR antibody described herein) and wherein the immunotherapeutic agent is an immunosuppressive agent. In some embodiments, the GCGR antagonist is a humanized version of antibody 6B5 and the immunotherapeutic agent is an immunosuppressive agent. In some embodiments, the GCGR antagonist is a humanized version of antibody 6B5 and the immunotherapeutic agent is an immunosuppressive agent (e.g., azathioprine, mycophenolate mofetil, or cyclosporine). In some embodiments, the GCGR antagonist is a humanized version of antibody 6B5 and the immunotherapeutic agent is an anti-CD3 antibody (e.g., Muromab, otelixizumab, teplizumab, visilizumab, foralumab, humanized M291). In some embodiments, the GCGR antagonist is a humanized version of antibody 6B5 and the immunotherapeutic agent is an IL-1 inhibitor (e.g., an anti-IL-1β antibody, an anti-IL-1α antibody, or an anti-IL-1R antibody). In some embodiments, the GCGR antagonist is a humanized version of antibody 6B5 and the immunotherapeutic agent is an anti-CD20 antibody (e.g., rituximab (RITUXAN)). In some embodiments, the GCGR antagonist is a humanized version of antibody 6B5 and the immunotherapeutic agent is an IL-6 inhibitor (e.g., an anti-IL-6 antibody or an anti-IL-6R antibody). In some embodiments, the GCGR antagonist is a humanized version of antibody 6B5 and the immunotherapeutic agent is an IL-17 inhibitor (e.g., an anti-IL17 antibody or an anti-IL-17 antibody). In some embodiments, the subject is human.

As used herein, the term "metabolic syndrome" refers to a cluster of conditions including increased blood pressure (e.g., hypertension), high blood glucose (and/or insulin resistance), excess body fat around the waist, obesity, and abnormal cholesterol or triglyceride levels (e.g., dyslipidemia) that occur together, increasing an individual's risk of cardiovascular disease, stroke, and diabetes. Metabolic syndrome may be defined by a number of parameters, including but not limited to, (i) abdominal obesity (waist circumference of greater than 40 inches in men and greater than 35 inches in women), (ii) triglyceride level of 150 mg/dL or greater, (iii) HDL cholesterol of less than 40 mg/dL in men or less than 50 mg/dL in women; (iv) systolic blood pressure of 130 mm Hg or greater or diastolic blood pressure of 85 Hg or greater; and (v) fasting glucose of 100 mg/dL or greater. There is evidence that beta cell dysfunction is associated with the severity of metabolic syndrome in some adults (Malin et al., 2014, *Metabolic Syndrome and Related Disorders*, 12:79-85).

In some embodiments, a method of treating metabolic syndrome in a subject (e.g., a human) comprises administering to the subject a therapeutically effective amount of a GCGR antagonist and a therapeutically effective amount of an immunotherapeutic agent. In some embodiments, a method of treating metabolic syndrome in a subject comprises administering to the subject a therapeutically effective amount of a GCGR antagonist and a therapeutically effective amount of an immunotherapeutic agent, wherein the GCGR antagonist is an antibody that specifically binds GCGR (e.g., an anti-GCGR antibody described herein). In some embodiments, a method of treating metabolic syndrome in a subject comprises administering to the subject a therapeutically effective amount of a GCGR antagonist and a therapeutically effective amount of an immunotherapeutic agent, wherein the GCGR antagonist is an antibody that specifically binds GCGR (e.g., an anti-GCGR antibody described herein) and wherein the immunotherapeutic agent is an immunosuppressive agent. In some embodiments, the GCGR antagonist is a humanized version of antibody 6B5 and the immunotherapeutic agent is an immunosuppressive agent. In some embodiments, the GCGR antagonist is a humanized version of antibody 6B5 and the immunotherapeutic agent is an immunosuppressive agent (e.g., azathioprine, mycophenolate mofetil, or cyclosporine). In some embodiments, the GCGR antagonist is a humanized version of antibody 6B5 and the immunotherapeutic agent is an anti-CD3 antibody (e.g., Muromab, otelixizumab, teplizumab, visilizumab, foralumab, humanized M291). In some embodiments, the GCGR antagonist is a humanized version of antibody 6B5 and the immunotherapeutic agent is an IL-1 inhibitor (e.g., an anti-IL-1β antibody, an anti-IL-1α antibody, or an anti-IL-1R antibody). In some embodiments, the GCGR antagonist is a humanized version of antibody 6B5 and the immunotherapeutic agent is an anti-CD20 antibody (e.g., rituximab (RITUXAN)). In some embodiments, the GCGR antagonist is a humanized version of antibody 6B5 and the immunotherapeutic agent is an IL-6 inhibitor (e.g., an anti-IL-6 antibody or an anti-IL-6R antibody). In some embodiments, the GCGR antagonist is a humanized version of antibody 6B5 and the immunotherapeutic agent is an IL-17 inhibitor (e.g., an anti-IL17 antibody or an anti-IL-17 antibody). In some embodiments, the subject is human.

As discussed herein, beta cells are a unique type of cell found pancreatic islets that synthesize, store, and release insulin. Beta cells make up 50-70% of the cells in human islets. Adequate and proper beta cell function requires normal beta cell integrity and beta cell mass. Damage to beta cells develops due to a variety of reasons, including but not limited to, cytokine-induced inflammation, obesity, insulin resistance, overconsumption of saturated fat and free fatty acids, autoimmunity, and chronic hyperglycemia. A progressive decline of beta cell function (i.e., beta cell dysfunction) leading to beta cell exhaustion generally precedes beta cell demise. Loss of beta cell mass and function are central to the development of both Type 1 and Type 2 diabetes (see, e.g., Cerf, 2013, Frontiers in Endocrinology, 4:1-12) as well as metabolic syndrome.

In some embodiments, a method of treating a disease, disorder, or condition in a subject (e.g., a human), wherein the disease, disorder, or condition is associated with beta cell dysfunction comprises administering to the subject a therapeutically effective amount of a GCGR antagonist and a therapeutically effective amount of an immunotherapeutic agent. In some embodiments, a method of treating a disease, disorder, or condition in a subject, wherein the disease, disorder, or condition is associated with beta cell dysfunction comprises administering to the subject a therapeutically effective amount of a GCGR antagonist and a therapeutically effective amount of an immunotherapeutic agent, wherein the GCGR antagonist is an antibody that specifically binds GCGR (e.g., an anti-GCGR antibody described herein). In some embodiments, a method of treating a disease, disorder, or condition in a subject, wherein the disease, disorder, or condition is associated with beta cell dysfunction comprises administering to the subject a therapeutically effective amount of a GCGR antagonist and a therapeutically effective amount of an immunotherapeutic agent, wherein the GCGR antagonist is an antibody that specifically binds GCGR (e.g., an anti-GCGR antibody described herein) and wherein the immunotherapeutic agent is an immunosuppressive agent. In some embodiments, the GCGR antagonist is a humanized version of antibody 6B5 and the immunotherapeutic agent is an immunosuppressive agent (e.g., azathioprine, mycophenolate mofetil, or cyclosporine). In some embodiments, the GCGR antagonist is a humanized version of antibody 6B5 and the immunotherapeutic agent is an anti-CD3 antibody (e.g., Muromab, otelixizumab, teplizumab, visilizumab, foralumab, humanized M291). In some embodiments, the GCGR antagonist is a humanized version of antibody 6B5 and the immunotherapeutic agent is an IL-1 inhibitor (e.g., an anti-IL-1β antibody, an anti-IL-1α antibody, or an anti-IL-1R antibody). In some embodiments, the GCGR antagonist is a humanized version of antibody 6B5 and the immunotherapeutic agent is an anti-CD20 antibody (e.g., rituximab (RITUXAN)). In some embodiments, the GCGR antagonist is a humanized version of antibody 6B5 and the immunotherapeutic agent is an IL-6 inhibitor (e.g., an anti-IL-6 antibody or an anti-IL-6R antibody). In some embodiments, the GCGR antagonist is a humanized version of antibody 6B5 and the immunotherapeutic agent is an IL-17 inhibitor (e.g., an anti-IL17 antibody or an anti-IL-17 antibody). In some embodiments, the subject is human. In some embodiments, the disease, disorder, or condition associated with beta cell dysfunction is diabetes (diabetes mellitus). In some instances, the disease, disorder, or condition associated with beta cell dysfunction is pre diabetes. In some embodiments, the disease, disorder, or condition associated with beta cell dysfunction is autoimmune diabetes. In some embodiments, the disease, disorder, or condition associated with beta cell dysfunction is Type 1 diabetes (e.g., juvenile diabetes, brittle diabetes, insulin-dependent diabetes). In some embodiments, the disease, disorder, or condition associated with beta cell dysfunction is latent autoimmune diabetes of adults (LADA). In some embodiments, the disease, disorder, or condition associated with beta cell dysfunction is Type 2 diabetes (e.g., non-insulin-dependent diabetes). In some embodiments, the disease, disorder, or condition associated with beta cell dysfunction is metabolic syndrome.

In some embodiments of the methods described herein, a treatment method reduces blood glucose levels in the subject. In some embodiments of the methods described herein, a treatment method increases C-peptide levels in the blood of the subject. In some embodiments of the methods described herein, a treatment method increases C-peptide levels in the pancreas of the subject. In some embodiments of the methods described herein, a treatment method decreases HbA1c in the blood of the subject. In some embodiments of the methods described herein, a treatment method reduces supplemental insulin use by the subject. Supplemental insulin is administered to maintain glucose levels as close to "normal" or healthy levels as possible. The amount of supplemental insulin needed by any individual depends upon a multitude of factors including food intake, physical activity, weight, etc. Reducing the amount of supplemental insulin needed on a daily basis is considered a positive benefit.

Measurement of the glycated hemoglobin A1c (HbA1c) is used in the management of subjects with diabetes. HbA1c is used to monitor long-term glycemic control, adjust therapy, assess the quality of diabetes care and predict the risk of the development of complications. HbAc1 is also used to identify subjects that may developed diabetes, i.e., the subjects are "pre-diabetic". An HbA1c test measures the amount of blood glucose attached to hemoglobin. Generally, an HbA1c test shows what the average amount of glucose attached to hemoglobin has been over the past three months. It's a three-month average because that's typically how long a red blood cell lives. HbA1c results are usually presented as a percentage, (i) "normal" considered to be below 5.7%, (ii) "prediabetes" considered to be between 5.7 and 6.4%, and (iii) "diabetes" considered to be above 6.5%.

In some embodiments, a method of preventing or slowing down progression of diabetes in a subject (e.g., a human) comprises administering to the subject a therapeutically effective amount of a GCGR antagonist and a therapeutically effective amount of an immunotherapeutic agent. In some embodiments, a method of preventing or slowing down progression of diabetes in a subject comprises administering to the subject a therapeutically effective amount of a GCGR antagonist and a therapeutically effective amount of an immunotherapeutic agent, wherein the GCGR antagonist is an antibody that specifically binds GCGR (e.g., an anti-GCGR antibody described herein). In some embodiments, a method of preventing or slowing down progression of diabetes in a subject comprises administering to the subject a therapeutically effective amount of a GCGR antagonist and a therapeutically effective amount of an immunotherapeutic agent, wherein the GCGR antagonist is an antibody that specifically binds GCGR (e.g., an anti-GCGR antibody described herein) and wherein the immunotherapeutic agent is an immunosuppressive agent. In some embodiments, the GCGR antagonist is a humanized version of antibody 6B5 and the immunotherapeutic agent is an immunosuppressive agent (e.g., azathioprine, mycophenolate mofetil, or cyclosporine). In some embodiments, the GCGR antagonist is a humanized version of antibody 6B5 and the immunotherapeutic agent is an anti-CD3 antibody (e.g., Muromab, otelixizumab, teplizumab, visilizumab, foralumab, humanized M291). In some embodiments, the GCGR antagonist is a humanized version of antibody 6B5 and the immunotherapeutic agent is an IL-1 inhibitor (e.g., an anti-IL-1β antibody, an anti-IL-1α antibody, or an anti-IL-1R antibody). In some embodiments, the GCGR antagonist is a humanized version of antibody 6B5 and the immunotherapeutic agent is an anti-CD20 antibody (e.g., rituximab (RITUXAN)). In some embodiments, the GCGR antagonist is a humanized version of antibody 6B5 and the immunotherapeutic agent is an IL-6 inhibitor (e.g., an anti-IL-6 antibody or an anti-IL-6R antibody). In some embodiments, the GCGR antagonist is a humanized version of antibody 6B5 and the immunotherapeutic agent is an IL-17 inhibitor (e.g., an anti-IL17 antibody or an anti-IL-17 antibody). In some embodiments, the subject is human.

In some embodiments, the disclosure features a method of reducing the risk of developing diabetes in a subject (e.g., a human), the method comprising administering to the subject a therapeutically effective amount of a GCGR antagonist and a therapeutically effective amount of an immunotherapeutic agent. In some embodiments, a method of reducing the risk of developing diabetes in a subject comprises administering to the subject a therapeutically effective amount of a GCGR antagonist and a therapeutically effective amount of an immunotherapeutic agent, wherein the GCGR antagonist is an antibody that specifically binds GCGR (e.g., an anti-GCGR antibody described herein). In some embodiments, a method of reducing the risk of developing diabetes in a subject comprises administering to the subject a therapeutically effective amount of a GCGR antagonist and a therapeutically effective amount of an immunotherapeutic agent, wherein the GCGR antagonist is an antibody that specifically binds GCGR (e.g., an anti-GCGR antibody described herein) and wherein the immunotherapeutic agent is an immunosuppressive agent. In some embodiments, the GCGR antagonist is a humanized version of antibody 6B5 and the immunotherapeutic agent is an immunosuppressive agent (e.g., azathioprine, mycophenolate mofetil, or cyclosporine). In some embodiments, the GCGR antagonist is a humanized version of antibody 6B5 and the immunotherapeutic agent is an anti-CD3 antibody (e.g., Muromab, otelixizumab, teplizumab, visilizumab, foralumab, humanized M291). In some embodiments, the GCGR antagonist is a humanized version of antibody 6B5 and the immunotherapeutic agent is an IL-1 inhibitor (e.g., an anti-IL-1β antibody, an anti-IL-1α antibody, or an anti-IL-1R antibody). In some embodiments, the GCGR antagonist is a humanized version of antibody 6B5 and the immunotherapeutic agent is an anti-CD20 antibody (e.g., rituximab (RITUXAN)). In some embodiments, the GCGR antagonist is a humanized version of antibody 6B5 and the immunotherapeutic agent is an IL-6 inhibitor (e.g., an anti-IL-6 antibody or an anti-IL-6R antibody). In some embodiments, the GCGR antagonist is a humanized version of antibody 6B5 and the immunotherapeutic agent is an IL-17 inhibitor (e.g., an anti-IL17 antibody or an anti-IL-17 antibody). In some embodiments, the subject is human.

In some embodiments, a method of improving beta cell function in a subject (e.g., a human) comprises administering to the subject a therapeutically effective amount of a GCGR antagonist and a therapeutically effective amount of an immunotherapeutic agent. In some embodiments, a method of improving beta cell function in a subject comprises administering to the subject a therapeutically effective amount of a GCGR antagonist and a therapeutically effective amount of an immunotherapeutic agent, wherein the GCGR antagonist is an antibody that specifically binds GCGR (e.g., an anti-GCGR antibody described herein). In some embodiments, a method of improving beta cell function in a subject comprises administering to the subject a therapeutically effective amount of a GCGR antagonist and a therapeutically effective amount of an immunotherapeutic agent, wherein the GCGR antagonist is an antibody that specifically binds GCGR (e.g., an anti-GCGR antibody described herein) and wherein the immunotherapeutic agent is an immunosuppressive agent. In some embodiments, the GCGR antagonist is a humanized version of antibody 6B5 and the immunotherapeutic agent is an immunosuppressive agent (e.g., azathioprine, mycophenolate mofetil, or cyclosporine). In some embodiments, the GCGR antagonist is a humanized version of antibody 6B5 and the immunotherapeutic agent is an anti-CD3 antibody (e.g., Muromab, otelixizumab, teplizumab, visilizumab, foralumab, humanized M291). In some embodiments, the GCGR antagonist is a humanized version of antibody 6B5 and the immunotherapeutic agent is an IL-1 inhibitor (e.g., an anti-IL-1β antibody, an anti-IL-1α antibody, or an anti-IL-1R antibody). In some embodiments, the GCGR antagonist is a humanized version of antibody 6B5 and the immunotherapeutic agent is an anti-CD20 antibody (e.g., rituximab (RITUXAN)). In some embodiments, the GCGR antagonist is a humanized version of antibody 6B5 and the immunotherapeutic agent is an IL-6 inhibitor (e.g., an anti-IL-6 antibody or an anti-IL-6R antibody). In some embodiments, the GCGR antagonist is a humanized version of antibody 6B5 and the immunotherapeutic agent is an IL-17 inhibitor (e.g., an anti-IL17 antibody or an anti-IL-17 antibody). In some embodiments, the subject is human.

In some embodiments, the improvement in beta cell function is indicated by a reduction in blood glucose levels. In some embodiments, the improvement in beta cell function is indicated by an increase in C-peptide levels in the blood. In some embodiments, the improvement in beta cell function is indicated by an increase in C-peptide levels in the pancreas. In some embodiments, the improvement in beta cell function is indicated by a reduction of HbA1c in the blood. In some embodiments, the improvement in beta cell function is indicated by a reduction in supplemental insulin use by the subject.

In some embodiments, a method of preserving beta cell function in a subject (e.g., a human) comprises administering to the subject a therapeutically effective amount of a GCGR antagonist and a therapeutically effective amount of an immunotherapeutic agent. In some embodiments, a method of preserving beta cell function in a subject comprises administering to the subject a therapeutically effective amount of a GCGR antagonist and a therapeutically effective amount of an immunotherapeutic agent, wherein the GCGR antagonist is an antibody that specifically binds GCGR (e.g., an anti-GCGR antibody described herein). In some embodiments, a method of preserving beta cell function in a subject comprises administering to the subject a therapeutically effective amount of a GCGR antagonist and a therapeutically effective amount of an immunotherapeutic agent, wherein the GCGR antagonist is an antibody that specifically binds GCGR (e.g., an anti-GCGR antibody described herein) and wherein the immunotherapeutic agent is an immunosuppressive agent. In some embodiments, the GCGR antagonist is a humanized version of antibody 6B5 and the immunotherapeutic agent is an immunosuppressive agent (e.g., azathioprine, mycophenolate mofetil, or cyclosporine). In some embodiments, the GCGR antagonist is a humanized version of antibody 6B5 and the immunotherapeutic agent is an anti-CD3 antibody (e.g., Muromab, otelixizumab, teplizumab, visilizumab, foralumab, humanized M291). In some embodiments, the GCGR antagonist is a humanized version of antibody 6B5 and the immunotherapeutic agent is an IL-1 inhibitor (e.g., an anti-IL-1β antibody, an anti-IL-1α antibody, or an anti-IL-1R antibody). In some embodiments, the GCGR antagonist is a humanized version of antibody 6B5 and the immunotherapeutic agent is an anti-CD20 antibody (e.g., rituximab (RITUXAN)). In some embodiments, the GCGR antagonist is a humanized version of antibody 6B5 and the immunotherapeutic agent is an IL-6 inhibitor (e.g., an anti-IL-6 antibody or an anti-IL-6R antibody). In some embodiments, the GCGR antagonist is a humanized version of antibody 6B5 and the immunotherapeutic agent is an IL-17 inhibitor (e.g., an anti-IL17 antibody or an anti-IL-17 antibody). In some embodiments, the subject is human.

In some embodiments, a method of preventing or slowing down progression of beta cell dysfunction in a subject (e.g., a human) comprises administering to the subject a therapeutically effective amount of a GCGR antagonist and a therapeutically effective amount of an immunotherapeutic agent. In some embodiments, a method of preventing or slowing down progression of beta cell dysfunction in a subject comprises administering to the subject a therapeutically effective amount of a GCGR antagonist and a therapeutically effective amount of an immunotherapeutic agent, wherein the GCGR antagonist is an antibody that specifically binds GCGR (e.g., an anti-GCGR antibody described herein). In some embodiments, a method of preventing or slowing down progression of beta cell dysfunction in a subject comprises administering to the subject a therapeutically effective amount of a GCGR antagonist and a therapeutically effective amount of an immunotherapeutic agent, wherein the GCGR antagonist is an antibody that specifically binds GCGR (e.g., an anti-GCGR antibody described herein) and wherein the immunotherapeutic agent is an immunosuppressive agent. In some embodiments, the GCGR antagonist is a humanized version of antibody 6B5 and the immunotherapeutic agent is an immunosuppressive agent (e.g., azathioprine, mycophenolate mofetil, or cyclosporine). In some embodiments, the GCGR antagonist is a humanized version of antibody 6B5 and the immunotherapeutic agent is an anti-CD3 antibody (e.g., Muromab, otelixizumab, teplizumab, visilizumab, foralumab, humanized M291). In some embodiments, the GCGR antagonist is a humanized version of antibody 6B5 and the immunotherapeutic agent is an IL-1 inhibitor (e.g., an anti-IL-1β antibody, an anti-IL-1α antibody, or an anti-IL-1R antibody). In some embodiments, the GCGR antagonist is a humanized version of antibody 6B5 and the immunotherapeutic agent is an anti-CD20 antibody (e.g., rituximab (RITUXAN)). In some embodiments, the GCGR antagonist is a humanized version of antibody 6B5 and the immunotherapeutic agent is an IL-6 inhibitor (e.g., an anti-IL-6 antibody or an anti-IL-6R antibody). In some embodiments, the GCGR antagonist is a humanized version of antibody 6B5 and the immunotherapeutic agent is an IL-17 inhibitor (e.g., an anti-IL17 antibody or an anti-IL-17 antibody). In some embodiments, the subject is human.

In some embodiments, a method of preventing beta cell destruction in a subject (e.g., a human) comprises administering to the subject a therapeutically effective amount of a GCGR antagonist and a therapeutically effective amount of an immunotherapeutic agent. In some embodiments, a method of preventing beta cell destruction in a subject comprises administering to the subject a therapeutically effective amount of a GCGR antagonist and a therapeutically effective amount of an immunotherapeutic agent, wherein the GCGR antagonist is an antibody that specifically binds GCGR (e.g., an anti-GCGR antibody described herein). In some embodiments, a method of preventing beta cell destruction in a subject comprises administering to the subject a therapeutically effective amount of a GCGR antagonist and a therapeutically effective amount of an immunotherapeutic agent, wherein the GCGR antagonist is an antibody that specifically binds GCGR (e.g., an anti-GCGR antibody described herein) and wherein the immunotherapeutic agent is an immunosuppressive agent. In some embodiments, the GCGR antagonist is a humanized version of antibody 6B5 and the immunotherapeutic agent is an immunosuppressive agent (e.g., azathioprine, mycophenolate mofetil, or cyclosporine). In some embodiments, the GCGR antagonist is a humanized version of antibody 6B5 and the immunotherapeutic agent is an anti-CD3 antibody (e.g., Muromab, otelixizumab, teplizumab, visilizumab, foralumab, humanized M291). In some embodiments, the GCGR antagonist is a humanized version of antibody 6B5 and the immunotherapeutic agent is an IL-1 inhibitor (e.g., an anti-IL-1β antibody, an anti-IL-1α antibody, or an anti-IL-1R antibody). In some embodiments, the GCGR antagonist is a humanized version of antibody 6B5 and the immunotherapeutic agent is an anti-CD20 antibody (e.g., rituximab (RITUXAN)). In some embodiments, the GCGR antagonist is a humanized version of antibody 6B5 and the immunotherapeutic agent is an IL-6 inhibitor (e.g., an anti-IL-6 antibody or an anti-IL-6R antibody). In some embodiments, the GCGR antagonist is a humanized version of antibody 6B5 and the immunotherapeutic agent is an IL-17 inhibitor (e.g., an anti-IL17 antibody or an anti-IL-17 antibody). In some embodiments, the subject is human.

In some embodiments of the methods described herein, the subject has been newly diagnosed with diabetes. In some embodiments of the methods described herein, the subject has been newly diagnosed with Type 1 diabetes. In some embodiments of the methods described herein, the subject has new onset Type 1 diabetes. In some embodiments of the methods described herein, the subject has been newly diagnosed with Type 2 diabetes. In some embodiments of the methods described herein, the subject has been diagnosed as prediabetic. In some embodiments of the method described herein, the subject is considered to be prediabetic. To one of skill in the art, prediabetes generally means that a subject has blood glucose levels higher than normal but not high enough to be considered or diagnosed as diabetes. Generally, subjects that are considered to be prediabetic have a blood glucose level of from 100 to 125 mg/dL.

In some embodiments of the methods described herein, beta cell function (or dysfunction) is assessed by measuring C-peptide levels in the blood or in the pancreas. In some embodiments, beta cell dysfunction is identified in a subject (e.g., a human) by determining that the subject has a low level of C-peptide as compared to a normal reference level (e.g., Type 1 diabetes). In some embodiments, beta cell dysfunction is identified in a subject by determining that the subject has a high level of C-peptide as compared to a normal reference level (e.g., Type 2 diabetes). A "normal" reference level of C-peptide ranges from about 0.5-2.7 ng/mL or 0.2-0.9 nmol/L. Assays to determine C-peptide levels are known in the art (e.g., ELISA).

In some embodiments of the methods described herein, beta cell function (or dysfunction) is assessed by measuring HbA1c levels in the blood. When glucose rises in a subject's blood, it binds to the hemoglobin in their red blood cells. The HbA1c test measures how much glucose is bound to the red blood cells. Red blood cells live for about 3 months, so the test shows the average level of glucose in your blood for the past 3 months. Glucose levels may increase due to insufficient insulin production from the beta cells. Thus, in some embodiments, beta cell dysfunction is identified in a subject by determining that the subject has a high level of HbA1c as compared to a normal reference level. A "normal" reference level of HbA1c ranges from about 4-5.6%. HbA1c levels of 5.7-6.4% are considered to be prediabetic. HbA1c levels above 6.5% or higher are considered diagnostic for diabetes. Assays to determine HbA1c levels are known in the art (e.g., ELISA or HPLC).

In some embodiments of the methods described herein, beta cell function (or dysfunction) is assessed by measuring glucose levels in the blood. In some embodiments of the methods described herein, beta cell function (or dysfunction) is assessed by the amount of supplemental insulin used by the subject. In some embodiments of the methods described herein, the parameters measured to assess beta cell function, e.g., C-peptide levels, HbA1c levels, or glucose levels, are compared to levels that are considered normal by those of skill in the art. In some embodiments of the methods described herein, the parameters measured to assess beta cell function, e.g., C-peptide levels, HbA1c levels, or glucose levels, are compared to results obtained from the subject prior to treatment.

Type 1 diabetes is considered to be an autoimmune disease characterized by the specific destruction of the insulin-producing pancreatic beta cells. It is believed that genetic and environmental factors act together to precipitate the disease. However, understanding of the biological reasons for development of diabetes are still under investigation. It is believed that the destruction of beta cells is carried out by cytotoxic CD4+ and CD8+ T-cells and macrophages. These effector populations are generally controlled by or in balance with other components of the immune system, for example, T regulatory (Treg) cells and/or macrophage-derived suppressor cells (MDSCs). Defects or suppression of Treg cells and/or MDSCs may be at least one mechanism for the destruction of pancreatic beta cells by "out-of-control" autoreactive T-cells.

In some embodiments of the methods described herein, the combination of a GCGR antagonist and an immunotherapeutic agent increases or enhances Treg activity. In some embodiments, the combination of a GCGR antagonist and an immunotherapeutic agent increases or enhances MDSC activity. In some embodiments, the combination of a GCGR antagonist and an immunotherapeutic agent decreases cytolytic cell activity. In some embodiments, the combination of a GCGR antagonist and an immunotherapeutic agent decreases CD4+ and/or CD8+ cytolytic T-cell activity. In some embodiments, the combination of a GCGR antagonist and an immunotherapeutic agent increases the number or percentage of Treg cells. In some embodiments, the combination of a GCGR antagonist and an immunotherapeutic agent increases the number or percentage of MDSCs.

In some embodiments of the methods described herein, the GCGR antagonist is a small molecule. In some embodiments of the methods described herein, the GCGR antagonist is an antibody. In some embodiments of the methods described herein, the GCGR antagonist is an antibody that specifically binds GCGR (i.e., an anti-GCGR antibody). In some embodiments of the methods described herein, an anti-GCGR antibody is selected from the group consisting of: antibodies 6B5, 3H5, 5B11, 1C1, 1C3, 1H2, 4F8, 13G9, 14F4, and 14E9 described herein. In some embodiments of the methods described herein, an anti-GCGR antibody is selected from the group consisting of antibodies having the six CDRs of any one of: 6B5, 3H5, 5B11, 1C1, 1C3, 1H2, 4F8, 13G9, 14F4, and 14E9. In some embodiments of the methods described herein, an anti-GCGR antibody is selected from the group consisting of: a humanized version of antibodies 6B5, 3H5, 5B11, 1C1, 1C3, 1H2, 4F8, 13G9, 14F4, and 14E9 described herein. In some embodiments of the methods described herein, an anti-GCGR antibody is a humanized version of antibody 6B5. In some embodiments of the methods described herein, an anti-GCGR antibody is antibody Hz6B5. In some embodiments of the methods described herein, an anti-GCGR antibody comprises: a heavy chain variable region CDR1 comprising SEQ ID NO:6, a heavy chain variable region CDR2 comprising SEQ ID NO:7, a heavy chain variable region CDR3 comprising SEQ ID NO:8, a light chain variable region CDR1 comprising SEQ ID NO:9, a light chain variable region CDR2 comprising SEQ ID NO:10, and a light chain variable region CDR3 comprising SEQ ID NO:11. In some embodiments of the methods described herein, an anti-GCGR antibody comprises a heavy chain variable region comprising SEQ ID NO:14. In some embodiments of the methods described herein, an anti-GCGR antibody comprises a light chain variable region comprising SEQ ID NO:15. In some embodiments of the methods described herein, an anti-GCGR antibody comprises a heavy chain variable region comprising SEQ ID NO:14 and a light chain variable region comprising SEQ ID NO:15. In some embodiments of the methods described herein, an anti-GCGR antibody comprises a heavy chain comprising SEQ ID NO:79. In some embodiments of the methods described herein, an anti-GCGR antibody comprises a light chain comprising SEQ ID NO:81. In some embodiments of the methods described herein, an anti-GCGR antibody comprises a heavy chain comprising SEQ ID NO:79 and a light chain comprising SEQ ID NO:81.

In some embodiments of the methods described herein, the treatment (i) reduces blood glucose levels in the subject, (ii) increases C-peptide levels in the blood of the subject, (iii) increases C-peptide levels in the pancreas of the subject, (iv) reduces HbA1c in the blood of the subject, and/or (v) reduces supplemental insulin use by the subject. In some embodiments of the methods described herein, the treatment reduces blood glucose levels in the subject. In some embodiments of the methods described herein, the treatment increases C-peptide level in the blood of the subject. In some embodiments of the methods described herein, the treatment increases C-peptide levels in the pancreas of the subject. In some embodiments of the methods described herein, the treatment reduces HbA1c in the blood of the subject. In some embodiments of the methods described herein, the treatment reduces supplemental insulin use by the subject. In some embodiments, the treatment increases insulin (e.g., endogenous insulin) levels in the blood of the subject. In some embodiments, the treatment increases insulin levels/content in the pancreas of the subject.

In certain embodiments, a method comprises assessing the efficacy of a GCGR antagonist (e.g., an anti-GCGR antibody) in combination with an immunotherapeutic agent in preventing or treating a disease, disorder, or condition associated with beta cell dysfunction in a subject (e.g., a human), wherein the method comprises comparing the beta cell function in the subject before and after administration of the agents. In some embodiments, an increase in beta cell function after administration of the agents as compared to before administration of the agents is indicative of the efficacy of the agents in preventing or treating the disease, disorder, or condition associated with beta cell dysfunction. In some embodiments, an increase in beta cell function is identified by an increase in C-peptide levels and/or a decrease in HbA1c levels. In some embodiments, a decrease in blood glucose after administration of the agents as compared to before administration of the agents is indicative of the efficacy of the agents in preventing or treating the disease, disorder, or condition associated with beta cell dysfunction.

In some embodiments, a method comprises assessing the efficacy of a GCGR antagonist (e.g., an anti-GCGR antibody) in combination with an immunotherapeutic agent in preventing or treating a disease, disorder, or condition associated with beta cell dysfunction in a subject (e.g., a human), wherein the method comprises comparing serum or plasma C-peptide in the subject before and after administration of the agents. In some embodiments, an increase in serum or plasma C-peptide after administration of the agents as compared to before administration of the agents is indicative of the efficacy of the agents in preventing or treating the disease, disorder, or condition associated with beta cell dysfunction.

In some embodiments, a method comprises assessing the efficacy of a GCGR antagonist (e.g., an anti-GCGR antibody) in combination with an immunotherapeutic agent in preventing or treating a disease, disorder, or condition associated with beta cell dysfunction in a subject (e.g., a human), wherein the method comprises comparing gene expression of Ins1, Ins2, and/or Ngn3 in pancreatic tissue from the subject before and after administration of the agents. In some embodiments, an increase in expression of Ins1, Ins2, and/or Ngn3 after administration of the agents as compared to before administration of the agents is indicative of the efficacy of the agents in preventing or treating the disease, disorder, or condition associated with beta cell dysfunction. Gene expression of Ins1, Ins2, and/or Ngn3 in pancreatic tissue can be determined by techniques known in the art (e.g., RT-PCR).

In some embodiments, a method comprises selecting a subject (e.g., a human) having a disease, disorder, or condition associated with beta cell dysfunction, based on evaluation of the function of the subject's beta cells. In certain embodiments, a method comprises selecting a subject (e.g., a human) having a disease, disorder, or condition associated with beta cell dysfunction, based on evaluation of C-peptide, blood insulin, pancreatic insulin, and/or blood glucose levels. In certain embodiments, a method comprises selecting a subject (e.g., a human) having a disease, disorder, or condition associated with beta cell dysfunction based on the evaluation of gene expression of Ins1, Ins2, and/or Ngn3 in pancreatic tissue from the subject. In some embodiments of the methods, selection of the subject is for the purpose of predicting a clinical response, monitoring a clinical response, or monitoring subject compliance. In some embodiments of the methods, the subject has increased beta cell function after treatment. In some embodiments of the methods, the subject has increased C-peptide levels after treatment. In some embodiments of the methods, the subject has increased insulin levels after treatment. In some embodiments of the methods, the subject has reduced blood glucose levels after treatment. In some embodiments of the methods, the subject has increased pancreatic expression of Ins1, Ins2, and/or Ngn3 after treatment. In certain embodiments, the levels are compared to standards and/or levels that are considered "normal" by those of skill in the art.

In some embodiments of the methods described herein, a method comprises administering a GCGR antagonist (e.g., an anti-GCGR antibody) and an immunotherapeutic agent in combination with at least one additional therapeutic agent or therapeutic therapy (e.g., a third agent). In some embodiments, the at least one additional therapeutic agent comprises 1, 2, 3, or more additional therapeutic agents. Treatment with multiple therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects and/or increasing the therapeutic index of the agent(s). Combination therapy may decrease the likelihood that resistance to any one of the agents will develop.

In some embodiments, the combination of a GCGR antagonist (e.g., an anti-GCGR antibody) and an immunotherapeutic agent described herein and at least one additional therapeutic agent results in additive or synergistic results. In some embodiments, the combination therapy results in an increase in the therapeutic index of the GCGR antagonist. In some embodiments, the combination therapy results in an increase in the therapeutic index of the immunotherapeutic agent. In some embodiments, the combination therapy results in an increase in the therapeutic index of the additional therapeutic agent(s). In some embodiments, the combination therapy results in a decrease in the toxicity and/or side effects of the GCGR antagonist. In some embodiments, the combination therapy results in a decrease in the toxicity and/or side effects of the immunotherapeutic agent. In some embodiments, the combination therapy results in a decrease in the toxicity and/or side effects of the additional therapeutic agent(s).

In some embodiments, an additional therapeutic agent can be administered prior to, concurrently with, and/or subsequently to, administration of the GCGR antagonist and immunotherapeutic agent.

Combined administration can include co-administration, either in a single pharmaceutical formulation or using separate formulations, or consecutive administration in any order but generally within a time span such that all active agents can exert their biological activities. Preparation and dosing schedules for additional therapeutic agents can be used according to manufacturers' instructions, standard-of-care methods, or as determined empirically by the skilled practitioner.

In some embodiments, the additional (third or more) therapeutic agent is a hyperglycemia or diabetes drug. Hyperglycemia or diabetes drugs include, but are not limited to, insulin and insulin mimetics; PPAR (peroxisome proliferator-activated receptor) γ-agonists, such as pioglitazone, troglitazone, ciglitazone, rivoglitazone, rosiglitazone, and other 2,4-thiazolidinedione derivatives; DPP-4 inhibitors, such as sitagliptin (JANUVIA), vildagliptin, saxagliptin, linagliptin (TRADJENTA), dutogliptin, gemigliptin, and alogliptin (NESINA); GLP-1 analogs, such as exenatide, liraglutide, taspoglutide, albiglutide, and lixisenatide; biguanidine derivatives, such as metformin (GLUMETZA, GLUCOPHAGE), buformin, and phenformin; ATP-sensitive potassium channel modulators, such as mitiglinide, repaglinide, and nateglinide; sulfonylurea derivatives, such as tolbutamide, chlorpropamide, tolazamide, acetohexamide, glipizide, gliclazide, glimepiride, gliquidone, glibornuride, glisoxepid, glibenclamide, glisentide, glisolamide, glybuzole, and glyclopyramide; α-glucosidase inhibitors, such as miglitol (GLYSET), acarbose (PRECOSE), and voglibose; and SGLT2 inhibitors, such as canagliflozin (INVOKANA), dapagliflozin (FARXIGA), and empagliflozin (JARDIANCE).

In some embodiments, the additional (third or more) therapeutic agent is an obesity drug. Obesity drugs include, but are not limited to, orlistat (XENICAL), phentermine/topiramate (QSYMIA), lorcaserin (BELVIQ), naltrexone/bupropion (CONTRAVE) and liraglutide (SAXENDA).

In some embodiments, the additional (third or more) therapeutic agent is a lipid-lowering drug or a cholesterol-lowering drug. Lipid-lowering drugs include, but are not limited to, fibrates, statins, omega-3 fatty acids, and niacin. In some embodiments, the additional therapeutic agent is a fibrate. Fibrates are a class of amphipathic carboxylic acids and include, but are not limited to, aluminum clofibrate, bezafibrate, ciprofibrate, choline fenofibrae, clinofibrate, clofibrate (e.g., ATROMID-S), clofibride, fenofibrate (e.g., FIBRICOR, LOFIBRA, TRICOR), gemfibrozil (e.g., LOPID), ronifibrate, simfibrate, and fenofibric acid. In some embodiments, an additional therapeutic agent is a statin. Statins are HMG-CoA reductase inhibitors and include, but are not limited to, atorvastatin (LIPITOR), fluvastatin (LESCOL), lovastatin (MEVACOR), pravastatin (PRAVACHOL), rosuvastatin (ZOCOR), and pitavastatin (LIVALO). In some embodiments, the additional therapeutic agent is niacin (vitamin B3). In some embodiments, the additional therapeutic agent is an omega-3 fatty acid. Lipid-lowering drugs also include monoclonal antibodies, including but not limited to anti-PCSK9 antibodies such as evolocumab (REPATHA) and alirocumab (PRALUENT).

In some embodiments, an additional (third or more) therapeutic agent is selected from the group including, but to limited to, GLP-1, GLP-1 mimetics, and GLP-1 receptor agonists; GIP, GIP mimetics, and GIP receptor agonists; PACAP, PACAP mimetics, and PACAP receptor 3 agonists; cholesterol-lowering agents such as HMG-CoA reductase inhibitors, sequestrants, nicotinyl alcohol, nicotinic acid and salts thereof, PPAR alpha agonists, PPAR alpha/gamma dual agonists, inhibitors of cholesterol absorption, acyl CoA:cholesterol acyltransferase inhibitors, anti-oxidants, and LXR modulators; PPAR delta agonists; anti-obesity compounds; ileal bile acid transporter inhibitors; anti-inflammatory agents excluding glucocorticoids; protein tyrosine phosphatase-1B (PTP-IB) inhibitors, and CB1 antagonists/inverse agonists.

In some embodiments, an additional (third or more) therapeutic agent is a steroid such as prednisolone, prednisone, methylprednisolone, betamethasone, dexamethasone, or hydrocortisone.

In some embodiments, an additional (third or more) therapeutic agent is a cytokine suppressive anti-inflammatory drug (CSAID) or an antibody to or antagonist of other human cytokines or growth factors such as TNF, LT, IL-1β, IL-2, IL-6, IL-7, IL-8, IL-15, IL-16, IL-17, IL-18, EMAP-II, GM-CSF, FGF, and PDGF. In some embodiments, an additional (third or more) therapeutic agent is a TNF antagonist such as an anti-TNF antibody (e.g., REMICADE), an anti-TNF antibody fragment (e.g., CDP870), a soluble p55 or p75 TNF receptor or derivatives thereof, ENBREL, LENERCEPT, a soluble IL-13 receptor, a TNF-alpha converting enzyme (TACE) inhibitor, an IL-1 inhibitor, interleukin 11, an anti-P7s, p-selectin glycoprotein ligand (PSGL), interferon-beta-1a (AVONEX), or interferon-beta-1b (BETASERON). In some embodiments, an additional therapeutic agent is betatrophin. In some embodiments, an additional therapeutic agent is ciliary neurotrophic factor (CNTF).

For the treatment of a disease, disorder, or condition associated with beta cell dysfunction, the appropriate dosage of a GCGR antagonist (e.g., an anti-GCGR antibody) and the appropriate dosage of an immunotherapeutic agent depends on the disorder or disease to be treated, the severity and course of the disorder or disease, the responsiveness of the disorder or disease, whether the agents are administered for therapeutic or preventative purposes, previous therapy, the patient's clinical history, and so on. The GCGR antagonist and immunotherapeutic agent can be administered one time or over a series of treatments lasting from several days to several months, or until a cure is effected or a diminution of the disease state is achieved. The dosing schedule or strategy for the GCGR antagonist and the immunotherapeutic agent may be the same or may be different.

It will be appreciated that the combination of a GCGR antagonist (e.g., an anti-GCGR antibody) and an immunotherapeutic agent may be administered in any order or concurrently. In some embodiments, the GCGR antagonist and the immunotherapeutic agent are administered substantially simultaneously or concurrently. In some embodiments, a GCGR antagonist is administered within 1 year of the treatment with an immunotherapeutic agent. In some embodiments, a GCGR antagonist is administered within 10, 8, 6, 4, or 2 months of any treatment with an immunotherapeutic agent. In some embodiments, a GCGR antagonist is administered within 4, 3, 2, or 1 weeks of any treatment with an immunotherapeutic agent. In some embodiments, a GCGR antagonist is administered within 5, 4, 3, 2, or 1 days of any treatment with an immunotherapeutic agent. It will further be appreciated that the two (or more) agents or treatments may be administered to the subject within a matter of hours or minutes (i.e., substantially simultaneously).

The dose of a GCGR antagonist (e.g., an anti-GCGR antibody) described herein may vary depending on the nature and/or severity of the disease or disorder, as well as the condition of the subject. In some embodiments, dosage of the agent is from 0.01 µg/kg to 100 mg/kg of body weight, from 0.1 µg/kg to 100 mg/kg of body weight, from 1 µg/kg to 100 mg/kg of body weight, from 1 mg/kg to 100 mg/kg of body weight, 1 mg/kg to 80 mg/kg of body weight, from 1 mg/kg to 50 mg/kg of body weight, from 1 mg/kg to 25 mg/kg of body weight, from 1 mg/kg to 15 mg/kg of body weight, from 10 mg/kg to 100 mg/kg of body weight, from 10 mg/kg to 75 mg/kg of body weight, or from 10 mg/kg to 50 mg/kg of body weight. In some embodiments, dosage of the agent is from about 0.1 mg/kg to about 20 mg/kg of body weight. In some embodiments, dosage of the agent is about 0.5 mg/kg of body weight. In some embodiments, dosage of the agent is about 1 mg/kg of body weight. In some embodiments, dosage of the agent is about 1.5 mg/kg of body weight. In some embodiments, dosage of the agent is about 2 mg/kg of body weight. In some embodiments, dosage of the agent is about 2.5 mg/kg of body weight. In some embodiments, dosage of the agent is about 5 mg/kg of body weight. In some embodiments, dosage of the agent is about 7.5 mg/kg of body weight. In some embodiments, dosage of the agent is about 10 mg/kg of body weight. In some embodiments, dosage of the agents about 12.5 mg/kg of body weight. In some embodiments, dosage of the agent is about 15 mg/kg of body weight. In some embodiments, the agent is dosed once or more daily, weekly, monthly, or yearly. In some embodiments, the agent is dosed once every week, once every two weeks, once every three weeks, or once every four weeks.

In some embodiments of the methods described, a GCGR antagonist is administered as a composition. In some embodiments of the methods described, an immunotherapeutic is administered as a composition. In some embodiments of the methods described, a GCGR antagonist and an immunotherapeutic are administered as one composition.

In some embodiments of the methods described, a GCGR antagonist is administered as a pharmaceutical composition. In some embodiments of the methods described, an immunotherapeutic is administered as a pharmaceutical composition. In some embodiments of the methods described, a GCGR antagonist and an immunotherapeutic are administered as one pharmaceutical composition.

Pharmaceutical compositions or pharmaceutical formulation are prepared for storage and/or use by combining an agent of the present disclosure with a pharmaceutically acceptable vehicle (e.g., a carrier or excipient). Those of skill in the art generally consider pharmaceutically acceptable carriers, excipients, and/or stabilizers to be inactive ingredients of a formulation or pharmaceutical composition. A formulation prepared for storage of an agent or agents may be different or distinct from a formulation or composition prepared for use in a subject, for example, a preparation for intravenous injection.

Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol (PEG). (*Remington: The Science and Practice of Pharmacy*, $22^{nd}$ Edition, 2012, Pharmaceutical Press, London.). In some embodiments, the formulation is in the form of an aqueous solution. In some embodiments, the formulation is lyophilized or in an alternative dried form.

The pharmaceutical formulation can be in unit dosage form. Such formulations include tablets, pills, capsules, powders, granules, solutions or suspensions in water or non-aqueous media, or suppositories. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and diluents (e.g., water). These can be used to form a solid pre-formulation composition containing a homogeneous mixture of a compound of the present disclosure, or a non-toxic pharmaceutically acceptable salt thereof. The solid pre-formulation composition is then subdivided into unit dosage forms of a type described above. The tablets, pills, etc. of the formulation or composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials include a number of polymeric acids and mixtures of polymeric acids with such materials as shellac, cetyl alcohol, and cellulose acetate.

The agents (e.g., a GCGR antagonist and/or an immunotherapeutic agent) of the present disclosure may be formulated in any suitable form for delivery to a target cell/tissue. In some embodiments, an agent is formulated as a liposome, microparticle, microcapsule, albumin microsphere, microemulsion, nano-particle, nanocapsule, or macroemulsion. In some embodiments, the pharmaceutical formulation includes an agent of the present disclosure complexed with liposomes. Methods to produce liposomes are known to those of skill in the art. For example, some liposomes are generated by reverse phase evaporation with a lipid composition comprising phosphatidylcholine, cholesterol, and PEG-derivatized phosphatidylethanolamine (PEG-PE).

In some embodiments, an agent is formulated as a sustained-release preparation. Suitable examples of sustained-release preparations include semi-permeable matrices of solid hydrophobic polymers containing an agent, where the matrices are in the form of shaped articles (e.g., films or microcapsules). Sustained-release matrices include but are not limited to polyesters, hydrogels such as poly(2-hydroxy-ethyl-methacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions or formulations of the present disclosure can be administered in any number of ways for either local or systemic treatment. Administration can be topical by epidermal or transdermal patches, ointments, lotions, creams, gels, drops, suppositories, sprays, liquids and powders; pulmonary by inhalation or insufflation of powders or aerosols, including by nebulizer, intratracheal, and intranasal; oral; or parenteral including intravenous, intraarterial, intratumoral, subcutaneous, intraperitoneal, intramuscular (e.g., injection or infusion), or intracranial (e.g., intrathecal or intraventricular).

Various delivery systems are known and can be used to administer an agent described herein. In some embodiments, an agent or a composition described herein is delivered in a controlled release or sustained release system. In some embodiments, a pump is used to achieve a controlled or sustained release. In some embodiments, polymeric materials are used to achieve a controlled or sustained release of an agent described herein. Examples of polymers used in sustained release formulations include, but are not limited to, poly 2-hydroxy ethyl methacrylate, polymethyl methacrylate, polyacrylic acid, polyethylene-co-vinyl acetate, polymethacrylic acid, polyglycolides (PLG), polyanhydrides, poly N-vinyl pyrrolidone, polyvinyl alcohol (PVA), polyacrylamide, polyethylene glycol (PEG), polylactides (PLA), polylactide-co-glycolides (PLGA), and polyorthoesters. Any polymer used in a sustained release formulation should be inert, free of leachable impurities, stable on storage, sterile, and biodegradable.

In some embodiments, additional delivery systems are used to administer an agent described herein including, but not limited to, injectable drug delivery devices and osmotic pumps. Injectable drug delivery devices include, for example, hand-held devices (e.g., autoinjectors) or wearable devices. Different types of osmotic pump systems may include single compartment systems, dual compartment systems, and multiple compartment systems.

III. GCGR Antagonists

Amino acid (aa) sequences for human GCGR (e.g., UniProtKB No. P47871) are known to those of skill in the art and a representative sequence is provided herein as SEQ ID NO:1. As used herein, reference to amino acid positions of GCGR refer to the numbering of amino acid sequences including the signal sequence.

The present disclosure provides methods that comprise a GCGR antagonist. In some embodiments of the methods described herein, a GCGR antagonist is a small molecule. In some embodiments, a GCGR antagonist is a small molecule selected from the group consisting of: adomeglivant (LY-2409021), LY-2453905, LY-2393910, RVT-1502, DSR-17759, BAY 27-9955, PF-06291874, MK-0893, MK-3577, skyrin, CP-99711, NNC-92-1687, and NN-2501.

In some embodiments of the methods described herein, a GCGR antagonist is a polypeptide. In some embodiments, a GCGR antagonist is a small peptide. In some embodiments, a GCGR antagonist is an agent that specifically binds GCGR, i.e., "a GCGR-binding agent". In some embodiments, a GCGR-binding agent is an antibody, i.e., an anti-GCGR antibody. In some embodiments, a GCGR-binding agent is an antibody that specifically binds human GCGR. In some embodiments, a GCGR-binding agent specifically binds a fragment of GCGR. In some embodiments, a GCGR-binding agent specifically binds the extracellular domain of GCGR. In some embodiments, a GCGR-binding agent specifically binds a portion or fragment of the extracellular domain of GCGR. In some embodiments, a GCGR-binding agent specifically binds an epitope on GCGR. Non-limiting examples of GCGR-binding agents can be found in U.S. Patent Publication Nos. 2009/0041784, 2009/0252727, 2012/0128679; 2014/0335091, International Application No. PCT/US2018/015452, and International Publication No. WO 2011/030935.

In some embodiments of the methods described herein, a GCGR-binding agent (e.g., an anti-GCGR antibody) binds within amino acids 26-136 of human GCGR. In some embodiments, a GCGR-binding agent (e.g., an anti-GCGR antibody) binds within amino acids 28-123 of human GCGR. In some embodiments, a GCGR-binding agent (e.g., an anti-GCGR antibody) binds within amino acids 80-119 of human GCGR.

In some embodiments of the methods described herein, a GCGR-binding agent (e.g., an anti-GCGR antibody) binds within amino acids 26-136 of SEQ ID NO:1. In some embodiments, a GCGR-binding agent (e.g., an anti-GCGR antibody) binds within amino acids 28-123 of SEQ ID NO:1. In some embodiments, a GCGR-binding agent (e.g., an anti-GCGR antibody) binds within amino acids 80-119 of SEQ ID NO:1. In some embodiments, a GCGR-binding agent (e.g., an anti-GCGR antibody) binds within SEQ ID NO:3. In some embodiments, a GCGR-binding agent (e.g., an anti-GCGR antibody) binds within SEQ ID NO:4. In some embodiments, a GCGR-binding agent (e.g., an anti-GCGR antibody) binds within SEQ ID NO:5.

In some embodiments of the methods described herein, a GCGR-binding agent is an antibody. In some embodiments, the antibody is a recombinant antibody. In some embodiments, the antibody is a monoclonal antibody. In some embodiments, the antibody is a chimeric antibody. In some embodiments, the antibody is a humanized antibody. In some embodiments, the antibody is a human antibody. In some embodiments, the antibody is an IgA, IgD, IgE, IgG, or IgM antibody. In some embodiments, the antibody is an IgG1 antibody. In some embodiments, the antibody is an IgG2 antibody. In some embodiments, the antibody is an IgG3 antibody. In some embodiments, the antibody is an IgG4 antibody. In some embodiments, the antibody is an antibody fragment comprising at least one antigen-binding site. In some embodiments, the antibody is a bispecific antibody or a multispecific antibody. In some embodiments, the antibody is a monovalent antibody. In some embodiments, the antibody is a monospecific antibody. In some embodiments, the antibody is a bivalent antibody. In some instances, the antibody is an Fab, Fab', F(ab)$_2$, scFv, sc(Fv)$_2$, diabiody, or nanobody. In some embodiments, the antibody is isolated. In some embodiments, the antibody is substantially pure.

In some embodiments of the methods described herein, the GCGR-binding agents are polyclonal antibodies. Polyclonal antibodies can be prepared by any known method. In some embodiments, polyclonal antibodies are produced by immunizing an animal (e.g., a rabbit, rat, mouse, goat, donkey) with an antigen of interest (e.g., a purified peptide fragment, a recombinant protein, or a fusion protein) using multiple subcutaneous or intraperitoneal injections. In some embodiments, the antigen is conjugated to a carrier such as keyhole limpet hemocyanin (KLH), serum albumin, bovine thyroglobulin, or soybean trypsin inhibitor. The antigen (with or without a carrier protein) is diluted in sterile saline and usually combined with an adjuvant (e.g., Complete or Incomplete Freund's Adjuvant) to form a stable emulsion. After a sufficient period of time, polyclonal antibodies are recovered from the immunized animal, usually from blood or ascites. The polyclonal antibodies can be purified from serum or ascites according to standard methods in the art including, but not limited to, affinity chromatography, ion-exchange chromatography, gel electrophoresis, and dialysis.

In some embodiments of the methods described herein, a GCGR-binding agent is a monoclonal antibody. Monoclonal antibodies can be prepared by any known method. In some embodiments, monoclonal antibodies are prepared using hybridoma methods known to one of skill in the art. For example, using the hybridoma method, a mouse, rat, rabbit, hamster, or other appropriate host animal, is immunized as described above to elicit the production of antibodies. In some embodiments, lymphocytes are immunized in vitro. In some embodiments, the immunizing antigen is a human protein or a fragment thereof. In some embodiments, the immunizing antigen is a mouse protein or a fragment thereof.

Following immunization, lymphocytes are isolated and fused with a suitable myeloma cell line using, for example, polyethylene glycol. The hybridoma cells are selected using specialized media as known in the art and unfused lymphocytes and myeloma cells do not survive the selection process. Hybridomas that produce monoclonal antibodies directed specifically against a chosen antigen can be identified by a variety of screening methods including, but not limited to, immunoprecipitation, immunoblotting, and in vitro binding assays (e.g., flow cytometry, FACS, ELISA, SPR (e.g., Biacore), and radioimmunoassay). Once hybridoma cells that produce antibodies of the desired specificity, affinity, and/or activity are identified, the clones may be subcloned by limiting dilution techniques. The hybridomas can be propagated either in in vitro culture using standard methods or in vivo as ascites tumors in an animal. The monoclonal antibodies can be purified from the culture medium or ascites fluid according to standard methods in the art including, but not limited to, affinity chromatography, ion-exchange chromatography, gel electrophoresis, and dialysis.

In some embodiments, monoclonal antibodies are made using recombinant DNA techniques as known to one skilled in the art. For example, the polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using standard techniques. The isolated polynucleotides encoding the heavy and light chains are then cloned into suitable expression vectors which produce the monoclonal antibodies when transfected into host cells such as E. coli, simian COS cells, Chinese hamster ovary (CHO) cells, or myeloma cells that do not otherwise produce immunoglobulin proteins.

In some embodiments, recombinant monoclonal antibodies, or fragments thereof, are isolated from phage display libraries expressing variable domains or CDRs of a desired species. Screening of phage libraries can be accomplished by various techniques known in the art.

In some embodiments, a monoclonal antibody is modified using recombinant DNA technology to generate alternative antibodies. In some embodiments, the constant domains of the light chain and heavy chain of a mouse monoclonal antibody are substituted with constant regions from a human antibody to generate a chimeric antibody. In some embodiments, the constant domains are substituted with a non-immunoglobulin polypeptide to generate a fusion polypeptide. In some embodiments, the constant regions are truncated or removed to generate an antibody fragment of a monoclonal antibody. Site-directed or high-density mutagenesis of the variable region(s) can be used to optimize, for example, specificity and affinity of a monoclonal antibody.

In some embodiments of the methods described herein, a GCGR-binding agent is a humanized antibody. Various methods for generating humanized antibodies are known in the art. In some embodiments, a humanized antibody comprises one or more amino acid residues that have been introduced into its sequence from a source that is non-human. In some embodiments, humanization is performed by substituting one or more non-human CDR sequences for the corresponding CDR sequences of a human antibody. In some embodiments, the humanized antibodies are constructed by substituting all six CDRs of a non-human antibody (e.g., a mouse antibody) for the corresponding CDRs of a human antibody.

The choice of which human heavy chain variable region and/or light chain variable region are used for generating humanized antibodies can be made based on a variety of factors and by a variety of methods known in the art. In some embodiments, the "best-fit" method is used where the sequence of the variable region of a non-human (e.g., rodent) antibody is screened against the entire library of known human variable region sequences. The human sequence that is most similar to that of the non-human (e.g., rodent) sequence is selected as the human variable region framework for the humanized antibody. In some embodiments, a particular variable region framework derived from a consensus sequence of all human antibodies of a particular subgroup of light or heavy chains is selected as the variable region framework. In some embodiments, the variable region framework sequence is derived from the consensus sequences of the most abundant human subclasses. In some embodiments, human germline genes are used as the source of the variable region framework sequences.

Other methods for humanization include, but are not limited to, (i) a method called "superhumanization" that is described as the direct transfer of CDRs to a human germline framework, (ii) a method termed Human String Content (HSC) that is based on a metric of "antibody humanness", (iii) methods based on generation of large libraries of humanized variants (including phage, ribosomal, and yeast display libraries), and (iv) methods based on framework region shuffling.

In some embodiments, a GCGR-binding agent is a human antibody. Human antibodies can be prepared using various techniques known in the art. In some embodiments, human antibodies are generated from immortalized human B lymphocytes immunized in vitro. In some embodiments, human antibodies are generated from lymphocytes isolated from an immunized individual. In any case, cells that produce an antibody directed against a target antigen can be generated and isolated. In some embodiments, a human antibody is selected from a phage library, where that phage library expresses human antibodies. Alternatively, phage display technology may be used to produce human antibodies and antibody fragments in vitro, from immunoglobulin variable region gene repertoires from unimmunized donors. Techniques for the generation and use of antibody phage libraries are well-known in the art. Once antibodies are identified, affinity maturation strategies known in the art, including but not limited to, chain shuffling and site-directed mutagenesis, may be employed to generate higher affinity human antibodies. In some embodiments, human antibodies are produced in transgenic mice that contain human immunoglobulin loci. Upon immunization these mice are capable of producing the full repertoire of human antibodies in the absence of endogenous immunoglobulin production.

In some embodiments of the methods described herein, a GCGR-binding agent is a bispecific antibody. Bispecific antibodies are capable of recognizing and binding at least two different antigens or epitopes. The different epitopes can either be within the same molecule (e.g., two epitopes on GCGR) or on different molecules (e.g., one epitope on GCGR and one epitope on a different target). In some embodiments, a bispecific antibody has enhanced potency as compared to an individual antibody or to a combination of more than one antibody. In some embodiments, a bispecific antibody has reduced toxicity as compared to an individual antibody or to a combination of more than one antibody. It is known to those of skill in the art that any therapeutic agent may have unique pharmacokinetics (PK) (e.g., circulating half-life). In some embodiments, a bispecific antibody has the ability to synchronize the PK of two active binding agents wherein the two individual binding agents have different PK profiles. In some embodiments, a bispecific antibody has the ability to concentrate the actions of two agents in a common area (e.g., tissue) in a subject. In some embodiments, a bispecific antibody has the ability to concentrate the actions of two agents to a common target (e.g., a specific cell type). In some embodiments, a bispecific antibody has the ability to target the actions of two agents to more than one biological pathway or function. In some embodiments, a bispecific antibody has the ability to target two different cells and bring them closer together.

In some embodiments, a bispecific antibody has decreased toxicity and/or side effects. In some embodiments, a bispecific antibody has decreased toxicity and/or side effects as compared to a mixture of the two individual antibodies or the antibodies as single agents. In some embodiments, a bispecific antibody has an increased therapeutic index. In some embodiments, a bispecific antibody has an increased therapeutic index as compared to a mixture of the two individual antibodies or the antibodies as single agents.

Several techniques for making bispecific antibodies are known by those skilled in the art. In some embodiments, the bispecific antibodies comprise heavy chain constant regions with modifications in the amino acids which are part of the interface between the two heavy chains. In some embodiments, the bispecific antibodies are generated using a knobs-into-holes (KIH) strategy. In some embodiments, the bispecific antibodies comprise variant hinge regions incapable of forming disulfide linkages between the heavy chains. In some embodiments, the bispecific antibodies comprise heavy chains with changes in amino acids that result in altered electrostatic interactions. In some embodiments, the bispecific antibodies comprise heavy chains with changes in amino acids that result in altered hydrophobic/hydrophilic interactions.

Bispecific antibodies can be intact antibodies or antibody fragments comprising antigen-binding sites.

In some embodiments of the methods described herein, GCGR-binding agents with more than two specificities are contemplated. In some embodiments, trispecific or tetraspecific antibodies are generated. GCGR-binding agents with more than two valencies are contemplated. In some embodiments, trivalent or tetravalent antibodies are generated.

In some embodiments of the methods described herein, a GCGR-binding agent is an antibody that binds GCGR. In some embodiments, the GCGR-binding agent is an antibody that binds human GCGR. In some embodiments, the GCGR-binding agent is an antibody that binds a portion or fragment of GCGR. In some embodiments, the GCGR-binding agent is an antibody that binds the extracellular domain of GCGR. In some embodiments, the GCGR-binding agent is an antibody that binds a fragment or portion of the extracellular domain of GCGR. In some embodiments, the GCGR-binding agent is an antibody that binds a GCGR epitope. In some embodiments, the GCGR epitope is a linear epitope. In some embodiments, the GCGR epitope is a conformational epitope.

In some embodiments of the methods described herein, a GCGR antagonist is an antibody that comprises one, two, three, four, five, and/or six CDRs of any one of the antibodies described herein. In some embodiments, an anti-GCGR antibody comprises: (i) the heavy chain variable region CDR1, CDR2, and CDR3 from Table 1, and/or (ii) the light chain variable region CDR1, CDR2, and CDR3 from Table 1. In some embodiments, an anti-GCGR antibody comprises: (i) the heavy chain variable region CDR1, CDR2, and CDR3 from Table 2, and/or (ii) the light chain variable region CDR1, CDR2, and CDR3 from Table 2. In some embodiments, an anti-GCGR antibody comprises: (i) the heavy chain variable region CDR1, CDR2, and CDR3 from Table 3, and/or (ii) the light chain variable region CDR1, CDR2, and CDR3 from Table 3. In some embodiments, an anti-GCGR antibody comprises: (i) the heavy chain variable region CDR1, CDR2, and CDR3 from Table 4, and/or (ii) the light chain variable region CDR1, CDR2, and CDR3 from Table 4. In some embodiments, an anti-GCGR antibody comprises: (i) the heavy chain variable region CDR1, CDR2, and CDR3 from Table 5, and/or (ii) the light chain variable region CDR1, CDR2, and CDR3 from Table 5. In some embodiments, an anti-GCGR antibody comprises: (i) the heavy chain variable region CDR1, CDR2, and CDR3 from Table 6, and/or (ii) the light chain variable region CDR1, CDR2, and CDR3 from Table 6. In some embodiments, an anti-GCGR antibody comprises: (i)

the heavy chain variable region CDR1, CDR2, and CDR3 from Table 7, and/or (ii) the light chain variable region CDR1, CDR2, and CDR3 from Table 7. In some embodiments, an anti-GCGR antibody comprises: (i) the heavy chain variable region CDR1, CDR2, and CDR3 from Table 8, and/or (ii) the light chain variable region CDR1, CDR2, and CDR3 from Table 8. In some embodiments, an anti-GCGR antibody comprises: (i) the heavy chain variable region CDR1, CDR2, and CDR3 from Table 9, and/or (ii) the light chain variable region CDR1, CDR2, and CDR3 from Table 9. In some embodiments, an anti-GCGR antibody comprises: (i) the heavy chain variable region CDR1, CDR2, and CDR3 from Table 10, and/or (ii) the light chain variable region CDR1, CDR2, and CDR3 from Table 10.

CDRs are defined by a variety of methods/systems by those skilled in the art. These systems and/or definitions have been developed and refined over a number of years and include Kabat, Chothia, IMGT, AbM, Exemplary, and Contact. The Kabat definition is based on sequence variability and generally is the most commonly used. The Chothia definition is based on the location of the structural loop regions. The IMGT system is based on sequence variability and location within the structure of the variable domain. The AbM definition is a compromise between Kabat and Chothia. The Contact definition is based on analyses of the available antibody crystal structures. The Exemplary system is a combination of Kabat and Chothia. Software programs (e.g., abYsis) are available and known to those of skill in the art for analysis of antibody sequence and determination of CDRs.

The specific CDR sequences defined herein are generally based on a combination of Kabat and Chothia definitions (Exemplary system). However, it will be understood that reference to a heavy chain CDR or CDRs and/or a light chain CDR or CDRs of a specific antibody will encompass all CDR definitions as known to those of skill in the art. In one instance, the anti-GCGR antibody used in the methods described herein comprises the six CDRs of antibody 6B5 based on the Kabat definition. In one instance, the anti-GCGR antibody used in any of the methods described herein comprises the six CDRs of antibody 6B5 based on the Chothia definition. In one instance, the anti-GCGR antibody used in the methods described herein comprises the six CDRs of antibody 6B5 basedon the AbM definition. In one instance, the anti-GCGR antibody used in the methods described herein comprises the six CDRs of antibody 6B5 based on the IMGT definition. In one instance, the anti-GCGR antibody used in the methods described herein comprises the six CDRs of antibody 6B5 based on the contact definition.

In some embodiments of the methods described herein, an anti-GCGR antibody comprises a heavy chain variable region CDR1, CDR2, and CDR3 and a light chain variable region CDR1, CDR2, and CDR3 from the antibody designated 6B5. In some embodiments of the methods described herein, an anti-GCGR antibody comprises a heavy chain variable region CDR1, CDR2, and CDR3 and a light chain variable region CDR1, CDR2, and CDR3 from the antibody designated 3H5. In some embodiments of the methods described herein, an anti-GCGR antibody comprises a heavy chain variable region CDR1, CDR2, and CDR3 and a light chain variable region CDR1, CDR2, and CDR3 from the antibody designated 5B11. In some embodiments of the methods described herein, an anti-GCGR antibody comprises a heavy chain variable region CDR1, CDR2, and CDR3 and a light chain variable region CDR1, CDR2, and CDR3 from the antibody designated 1C1. In some embodiments of the methods described herein, an anti-GCGR antibody comprises a heavy chain variable region CDR1, CDR2, and CDR3 and a light chain variable region CDR1, CDR2, and CDR3 from the antibody designated 1C3. In some embodiments of the methods described herein, an anti-GCGR antibody comprises a heavy chain variable region CDR1, CDR2, and CDR3 and a light chain variable region CDR1, CDR2, and CDR3 from the antibody designated 1H2. In some embodiments of the methods described herein, an anti-GCGR antibody comprises a heavy chain variable region CDR1, CDR2, and CDR3 and a light chain variable region CDR1, CDR2, and CDR3 from the antibody designated 4F8. In some embodiments of the methods described herein, an anti-GCGR antibody comprises a heavy chain variable region CDR1, CDR2, and CDR3 and a light chain variable region CDR1, CDR2, and CDR3 from the antibody designated 13G9. In some embodiments of the methods described herein, an anti-GCGR antibody comprises a heavy chain variable region CDR1, CDR2, and CDR3 and a light chain variable region CDR1, CDR2, and CDR3 from the antibody designated 14F4. In some embodiments of the methods described herein, an anti-GCGR antibody comprises a heavy chain variable region CDR1, CDR2, and CDR3 and a light chain variable region CDR1, CDR2, and CDR3 from the antibody designated 14E9.

TABLE 1

| 6B5 | |
|---|---|
| Heavy Chain | |
| CDR1 | GFTFTNHWLG (SEQ ID NO: 6) |
| CDR2 | DIYPGGYYINYNEKFKG (SEQ ID NO: 7) |
| CDR3 | HTNYGSDY (SEQ ID NO: 8) |
| Light Chain | |
| CDR1 | RSSQSIVDSYGNTFLE (SEQ ID NO: 9) |
| CDR2 | KVSNRLS (SEQ ID NO: 10) |
| CDR3 | FQGSHVPWT (SEQ ID NO: 11) |

TABLE 2

| 3H5 | |
|---|---|
| Heavy Chain | |
| CDR1 | GNTFTNYWMH (SEQ ID NO: 16) |
| CDR2 | MIHPNSGSTHYNEKFKN (SEQ ID NO: 17) |
| CDR3 | TADYVMDY (SEQ ID NO: 18) |
| Light Chain | |
| CDR1 | KSTKSLLNSDGFTYLD (SEQ ID NO: 19) |
| CDR2 | LVSNRFS (SEQ ID NO: 20) |
| CDR3 | FQSNFLPLT (SEQ ID NO: 21) |

TABLE 3

| 5B11 | |
|---|---|
| Heavy Chain | |
| CDR1 | GNTFTSHWMH (SEQ ID NO: 24) |
| CDR2 | MSHPNSGSSNYSGKFKS (SEQ ID NO: 25) |
| CDR3 | TDYDYDGDY (SEQ ID NO: 26) |

TABLE 3-continued

5B11

Light Chain

| | |
|---|---|
| CDR1 | KSSKSLLNSDGLTYLD (SEQ ID NO: 27) |
| CDR2 | LVSNRFS (SEQ ID NO: 20) |
| CDR3 | FQSNFLPLT (SEQ ID NO: 21) |

TABLE 4

1C1

Heavy Chain

| | |
|---|---|
| CDR1 | GYTFTRNVIH (SEQ ID NO: 30) |
| CDR2 | YINPYNDGAKYNAKFKG (SEQ ID NO: 31) |
| CDR3 | WGNYEDFAMDY (SEQ ID NO: 32) |

Light Chain

| | |
|---|---|
| CDR1 | RASESVDIYGNSYMH (SEQ ID NO: 33) |
| CDR2 | LASNLES (SEQ ID NO: 34) |
| CDR3 | QQNNEDPFT (SEQ ID NO: 35) |

TABLE 5

1C3

Heavy Chain

| | |
|---|---|
| HC CDR1 | GYTFTSSVMH (SEQ ID NO: 38) |
| HC CDR2 | YINPYNDGTKYNENFKG (SEQ ID NO: 39) |
| HC CDR3 | GAGYDRGPMAMDY (SEQ ID NO: 40) |

Light Chain

| | |
|---|---|
| LC CDR1 | RASESVDSYGDSFVH (SEQ ID NO: 41) |
| LC CDR2 | FASNLES (SEQ ID NO: 42) |
| LC CDR3 | QQNNEVPFT (SEQ ID NO: 43) |

TABLE 6

1H2

Heavy Chain

| | |
|---|---|
| HC CDR1 | GYTFTSYWIT (SEQ ID NO: 46) |
| HC CDR2 | DIHPGGGDTNYNKKFKS (SEQ ID NO: 47) |
| HC CDR3 | DDNYVGFTY (SEQ ID NO: 48) |

Light Chain

| | |
|---|---|
| LC CDR1 | RSSQTIIHSDGNTYLE (SEQ ID NO: 49) |
| LC CDR2 | KVSNRFS (SEQ ID NO: 50) |
| LC CDR3 | FQGSHVPWT (SEQ ID NO: 11) |

TABLE 7

4F8

Heavy Chain

| | |
|---|---|
| HC CDR1 | GYTFSNYWIG (SEQ ID NO: 53) |
| HC CDR2 | DIYPGGFYDNYNDKFKG (SEQ ID NO: 54) |
| HC CDR3 | SGGLPGAGFTY (SEQ ID NO: 55) |

TABLE 7-continued

4F8

Light Chain

| | |
|---|---|
| LC CDR1 | RSSQHIVYSDGNTYLE (SEQ ID NO: 56) |
| LC CDR2 | KVSNRFS (SEQ ID NO: 50) |
| LC CDR3 | FQGSHVPWT (SEQ ID NO: 11) |

TABLE 8

13G9

Heavy Chain

| | |
|---|---|
| HC CDR1 | GYTFTNYWLG (SEQ ID NO: 59) |
| HC CDR2 | DIYPGGDYNNYNGKFKG (SEQ ID NO: 60) |
| HC CDR3 | SDDGYS (SEQ ID NO: 61) |

Light Chain

| | |
|---|---|
| LC CDR1 | RSSQSIVDSYGNTYLE (SEQ ID NO: 62) |
| LC CDR2 | KVSNRFA (SEQ ID NO: 63) |
| LC CDR3 | FQGSHIPWT (SEQ ID NO: 64) |

TABLE 9

14F4

Heavy Chain

| | |
|---|---|
| HC CDR1 | GYTFTNYWIG (SEQ ID NO: 67) |
| HC CDR2 | DIFPGGFYSNYNEKFKG (SEQ ID NO: 68) |
| HC CDR3 | IWDRGFDY (SEQ ID NO: 69) |

Light Chain

| | |
|---|---|
| LC CDR1 | RSSQSIVDSYGNTYLE (SEQ ID NO: 62) |
| LC CDR2 | KVSNRFS (SEQ ID NO: 50) |
| LC CDR3 | FQGSHVPYT (SEQ ID NO: 70) |

TABLE 10

14E9

Heavy Chain

| | |
|---|---|
| HC CDR1 | GYTFTNYWIG (SEQ ID NO: 67) |
| HC CDR2 | DISPGNYYTNYNAKFKD (SEQ ID NO: 73) |
| HC CDR3 | YDEFAY (SEQ ID NO: 74) |

Light Chain

| | |
|---|---|
| LC CDR1 | RSSQSIVHSDGNTYLE (SEQ ID NO: 75) |
| LC CDR2 | KVSNRFS (SEQ ID NO: 50) |
| LC CDR3 | FQGSHVPWT (SEQ ID NO: 11) |

In some embodiments of the methods described herein, an anti-GCGR antibody comprises (a) a heavy chain variable region CDR1 comprising GFTFTNHWLG (SEQ ID NO:6); a heavy chain variable region CDR2 comprising DIYPG-GYYINYNEKFKG (SEQ ID NO:7); and a heavy chain variable region CDR3 comprising HTNYGSDY (SEQ ID NO:8); and/or (b) a light chain variable region CDR1 comprising RSSQSIVDSYGNTFLE (SEQ ID NO:9); a light chain variable region CDR2 comprising KVSNRLS (SEQ ID NO:10); and a light chain variable region CDR3 comprising FQGSHVPWT (SEQ ID NO:11). In some embodiments, an anti-GCGR antibody comprises a heavy chain variable region CDR1 comprising GFTFTNHWLG (SEQ ID NO: 6); a heavy chain variable region CDR2 comprising DIYPGGYYINYNEKFKG (SEQ ID NO:7); and a heavy chain variable region CDR3 comprising HTNYGSDY (SEQ ID NO:8). In some embodiments, an anti-GCGR antibody comprises a light chain variable region CDR1 comprising RSSQSIVDSYGNTFLE (SEQ ID NO:9); a light chain variable region CDR2 comprising KVSNRLS (SEQ ID NO:10); and a light chain variable region CDR3 comprising FQGSHVPWT (SEQ ID NO:11). In some embodiments, an anti-GCGR antibody comprises a heavy chain variable region CDR1 comprising GFTFTNHWLG (SEQ ID NO:6); a heavy chain variable region CDR2 comprising DIYPGGYYINYNEKFKG (SEQ ID NO:7); a heavy chain variable region CDR3 comprising HTNYGSDY (SEQ ID NO:8); a light chain variable region CDR1 comprising RSSQSIVDSYGNTFLE (SEQ ID NO:9); a light chain variable region CDR2 comprising KVSNRLS (SEQ ID NO:10); and a light chain variable region CDR3 comprising FQGSHVPWT (SEQ ID NO:11).

In some embodiments, an anti-GCGR antibody comprises: (a) a heavy chain variable region CDR1 comprising GFTFTNHWLG (SEQ ID NO:6) or a variant thereof comprising 1, 2, 3, or 4 amino acid substitutions; a heavy chain variable region CDR2 comprising DIYPGGYY-INYNEKFKG (SEQ ID NO:7) or a variant thereof comprising 1, 2, 3, or 4 amino acid substitutions; a heavy chain variable region CDR3 comprising HTNYGSDY (SEQ ID NO:8) or a variant thereof comprising 1, 2, 3, or 4 amino acid substitutions; a light chain variable region CDR1 comprising RSSQSIVDSYGNTFLE (SEQ ID NO:9) or a variant thereof comprising 1, 2, 3, or 4 amino acid substitutions; a light chain variable region CDR2 comprising KVSNRLS (SEQ ID NO:10) or a variant thereof comprising 1, 2, 3, or 4 amino acid substitutions; and a light chain variable region CDR3 comprising FQGSHVPWT (SEQ ID NO:11) or a variant thereof comprising 1, 2, 3, or 4 amino acid substitutions. In some embodiments, the amino acid substitutions are conservative substitutions. In some embodiments, the substitutions are made as part of a humanization process. In some embodiments, the substitutions are made as part of a germline humanization process. In some embodiments, the substitutions are made as part of an affinity maturation process. In some embodiments, the substitutions are made as part of an optimization process.

In some embodiments, an anti-GCGR antibody comprises (a) a heavy chain variable region CDR1 comprising SEQ ID NO:16; a heavy chain variable region CDR2 comprising SEQ ID NO:17; and a heavy chain variable region CDR3 comprising SEQ ID NO:18; and/or (b) a light chain variable region CDR1 comprising SEQ ID NO:19; a light chain variable region CDR2 comprising SEQ ID NO:20; and a light chain variable region CDR3 comprising SEQ ID NO:21. In some embodiments, an anti-GCGR antibody comprises a heavy chain variable region CDR1 comprising SEQ ID NO:16; a heavy chain variable region CDR2 comprising SEQ ID NO:17; and a heavy chain variable region CDR3 comprising SEQ ID NO:18. In some embodiments, an anti-GCGR antibody comprises a light chain variable region CDR1 comprising SEQ ID NO:19; a light chain variable region CDR2 comprising SEQ ID NO:20; and a light chain variable region CDR3 comprising SEQ ID NO:21. In some embodiments, an anti-GCGR antibody comprises (a) a heavy chain variable region CDR1 comprising SEQ ID NO:16; a heavy chain variable region CDR2 comprising SEQ ID NO:17; and a heavy chain variable region CDR3 comprising SEQ ID NO:18; and (b) a light chain variable region CDR1 comprising SEQ ID NO:19; a light chain variable region CDR2 comprising SEQ ID NO:20; and a light chain variable region CDR3 comprising SEQ ID NO:21.

In some embodiments, an anti-GCGR antibody comprises (a) a heavy chain variable region CDR1 comprising SEQ ID NO:24; a heavy chain variable region CDR2 comprising SEQ ID NO:25; and a heavy chain variable region CDR3 comprising SEQ ID NO:26; and/or (b) a light chain variable region CDR1 comprising SEQ ID NO:27; a light chain variable region CDR2 comprising SEQ ID NO:20; and a light chain variable region CDR3 comprising SEQ ID NO:21. In some embodiments, an anti-GCGR antibody comprises a heavy chain variable region CDR1 comprising SEQ ID NO:24; a heavy chain variable region CDR2 comprising SEQ ID NO:25; and a heavy chain variable region CDR3 comprising SEQ ID NO:26. In some embodiments, an anti-GCGR antibody comprises a light chain variable region CDR1 comprising SEQ ID NO:27; a light chain variable region CDR2 comprising SEQ ID NO:20; and a light chain variable region CDR3 comprising SEQ ID NO:21. In some embodiments, an anti-GCGR antibody comprises (a) a heavy chain variable region CDR1 comprising SEQ ID NO:24; a heavy chain variable region CDR2 comprising SEQ ID NO:25; and a heavy chain variable region CDR3 comprising SEQ ID NO:26; and (b) a light chain variable region CDR1 comprising SEQ ID NO:27; a light chain variable region CDR2 comprising SEQ ID NO:20; and a light chain variable region CDR3 comprising SEQ ID NO:21.

In some embodiments, an anti-GCGR antibody comprises (a) a heavy chain variable region CDR1 comprising SEQ ID NO:30; a heavy chain variable region CDR2 comprising SEQ ID NO:31; and a heavy chain variable region CDR3 comprising SEQ ID NO:32; and/or (b) a light chain variable region CDR1 comprising SEQ ID NO:33; a light chain variable region CDR2 comprising SEQ ID NO:34; and a light chain variable region CDR3 comprising SEQ ID NO:35. In some embodiments, an anti-GCGR antibody comprises a heavy chain variable region CDR1 comprising SEQ ID NO:30; a heavy chain variable region CDR2 comprising SEQ ID NO:31; and a heavy chain variable region CDR3 comprising SEQ ID NO:32. In some embodiments, an anti-GCGR antibody comprises a light chain variable region CDR1 comprising SEQ ID NO:33; a light chain variable region CDR2 comprising SEQ ID NO:34; and a light chain variable region CDR3 comprising SEQ ID NO:35. In some embodiments, an anti-GCGR antibody comprises (a) a heavy chain variable region CDR1 comprising SEQ ID NO:30; a heavy chain variable region CDR2 comprising SEQ ID NO:31; and a heavy chain variable region CDR3 comprising SEQ ID NO:32; and (b) a light chain variable region CDR1 comprising SEQ ID NO:33; a light chain variable region CDR2 comprising SEQ ID NO:34; and a light chain variable region CDR3 comprising SEQ ID NO:35.

In some embodiments, an anti-GCGR antibody comprises (a) a heavy chain variable region CDR1 comprising SEQ ID NO:38; a heavy chain variable region CDR2 comprising SEQ ID NO:39; and a heavy chain variable region CDR3 comprising SEQ ID NO:40; and/or (b) a light chain variable region CDR1 comprising SEQ ID NO:41; a light chain variable region CDR2 comprising SEQ ID NO:42; and a light chain variable region CDR3 comprising SEQ ID NO:43. In some embodiments, an anti-GCGR antibody comprises a heavy chain variable region CDR1 comprising SEQ ID NO:38; a heavy chain variable region CDR2 comprising SEQ ID NO:39; and a heavy chain variable region CDR3 comprising SEQ ID NO:40. In some embodiments, an anti-GCGR antibody comprises a light chain variable region CDR1 comprising SEQ ID NO:41; a light chain variable region CDR2 comprising SEQ ID NO:42; and a light chain variable region CDR3 comprising SEQ ID NO:43. In some embodiments, an anti-GCGR antibody comprises (a) a heavy chain variable region CDR1 comprising SEQ ID NO:38; a heavy chain variable region CDR2 comprising SEQ ID NO:39; and a heavy chain variable region CDR3 comprising SEQ ID NO:40; and (b) a light chain variable region CDR1 comprising SEQ ID NO:41; a light chain variable region CDR2 comprising SEQ ID NO:42; and a light chain variable region CDR3 comprising SEQ ID NO:43.

In some embodiments, an anti-GCGR antibody comprises (a) a heavy chain variable region CDR1 comprising SEQ ID NO:46; a heavy chain variable region CDR2 comprising SEQ ID NO:47; and a heavy chain variable region CDR3 comprising SEQ ID NO:48; and/or (b) a light chain variable region CDR1 comprising SEQ ID NO:49; a light chain variable region CDR2 comprising SEQ ID NO:50; and a light chain variable region CDR3 comprising SEQ ID NO:11. In some embodiments, an anti-GCGR antibody comprises a heavy chain variable region CDR1 comprising SEQ ID NO:46; a heavy chain variable region CDR2 comprising SEQ ID NO:47; and a heavy chain variable region CDR3 comprising SEQ ID NO:48. In some embodiments, an anti-GCGR antibody comprises a light chain variable region CDR1 comprising SEQ ID NO:49; a light chain variable region CDR2 comprising SEQ ID NO:50; and a light chain variable region CDR3 comprising SEQ ID NO:11. In some embodiments, an anti-GCGR antibody comprises (a) a heavy chain variable region CDR1 comprising SEQ ID NO:46; a heavy chain variable region CDR2 comprising SEQ ID NO:47; and a heavy chain variable region CDR3 comprising SEQ ID NO:48; and (b) a light chain variable region CDR1 comprising SEQ ID NO:49; a light chain variable region CDR2 comprising SEQ ID NO:50; and a light chain variable region CDR3 comprising SEQ ID NO:11.

In some embodiments, an anti-GCGR antibody comprises (a) a heavy chain variable region CDR1 comprising SEQ ID NO:53; a heavy chain variable region CDR2 comprising SEQ ID NO:54; and a heavy chain variable region CDR3 comprising SEQ ID NO:55; and/or (b) a light chain variable region CDR1 comprising SEQ ID NO:56; a light chain variable region CDR2 comprising SEQ ID NO:50; and a light chain variable region CDR3 comprising SEQ ID NO:11. In some embodiments, an anti-GCGR antibody comprises a heavy chain variable region CDR1 comprising SEQ ID NO:53; a heavy chain variable region CDR2 comprising SEQ ID NO:54; and a heavy chain variable region CDR3 comprising SEQ ID NO:55. In some embodiments, an anti-GCGR antibody comprises a light chain variable region CDR1 comprising SEQ ID NO:56; a light chain variable region CDR2 comprising SEQ ID NO:50; and a light chain variable region CDR3 comprising SEQ ID NO:11. In some embodiments, an anti-GCGR antibody comprises (a) a heavy chain variable region CDR1 comprising SEQ ID NO:53; a heavy chain variable region CDR2 comprising SEQ ID NO:54; and a heavy chain variable region CDR3 comprising SEQ ID NO:55; and (b) a light chain variable region CDR1 comprising SEQ ID NO:56; a light chain variable region CDR2 comprising SEQ ID NO:50; and a light chain variable region CDR3 comprising SEQ ID NO:11.

In some embodiments, an anti-GCGR antibody comprises (a) a heavy chain variable region CDR1 comprising SEQ ID NO:59; a heavy chain variable region CDR2 comprising SEQ ID NO:60; and a heavy chain variable region CDR3 comprising SEQ ID NO:61; and/or (b) a light chain variable region CDR1 comprising SEQ ID NO:62; a light chain variable region CDR2 comprising SEQ ID NO:63; and a light chain variable region CDR3 comprising SEQ ID NO:64. In some embodiments, an anti-GCGR antibody comprises a heavy chain variable region CDR1 comprising SEQ ID NO:59; a heavy chain variable region CDR2 comprising SEQ ID NO:60; and a heavy chain variable region CDR3 comprising SEQ ID NO:61. In some embodiments, an anti-GCGR antibody comprises a light chain variable region CDR1 comprising SEQ ID NO:62; a light chain variable region CDR2 comprising SEQ ID NO:63; and a light chain variable region CDR3 comprising SEQ ID NO:64. In some embodiments, an anti-GCGR antibody comprises (a) a heavy chain variable region CDR1 comprising SEQ ID NO:59; a heavy chain variable region CDR2 comprising SEQ ID NO:60; and a heavy chain variable region CDR3 comprising SEQ ID NO:61; and (b) a light chain variable region CDR1 comprising SEQ ID NO:62; a light chain variable region CDR2 comprising SEQ ID NO:63; and a light chain variable region CDR3 comprising SEQ ID NO:64.

In some embodiments, an anti-GCGR antibody comprises (a) a heavy chain variable region CDR1 comprising SEQ ID NO:67; a heavy chain variable region CDR2 comprising SEQ ID NO:68; and a heavy chain variable region CDR3 comprising SEQ ID NO:69; and/or (b) a light chain variable region CDR1 comprising SEQ ID NO:62; a light chain variable region CDR2 comprising SEQ ID NO:50; and a light chain variable region CDR3 comprising SEQ ID NO:70. In some embodiments, an anti-GCGR antibody comprises a heavy chain variable region CDR1 comprising SEQ ID NO:67; a heavy chain variable region CDR2 comprising SEQ ID NO:68; and a heavy chain variable region CDR3 comprising SEQ ID NO:69. In some embodiments, an anti-GCGR antibody comprises a light chain variable region CDR1 comprising SEQ ID NO:62; a light chain variable region CDR2 comprising SEQ ID NO:50; and a light chain variable region CDR3 comprising SEQ ID NO:70. In some embodiments, an anti-GCGR antibody comprises (a) a heavy chain variable region CDR1 comprising SEQ ID NO:67; a heavy chain variable region CDR2 comprising SEQ ID NO:68; and a heavy chain variable region CDR3 comprising SEQ ID NO:69; and (b) a light chain variable region CDR1 comprising SEQ ID NO:62; a light chain variable region CDR2 comprising SEQ ID NO:50; and a light chain variable region CDR3 comprising SEQ ID NO:70.

In some embodiments, an anti-GCGR antibody comprises (a) a heavy chain variable region CDR1 comprising SEQ ID NO:67; a heavy chain variable region CDR2 comprising SEQ ID NO:73; and a heavy chain variable region CDR3 comprising SEQ ID NO:74; and/or (b) a light chain variable region CDR1 comprising SEQ ID NO:75; a light chain variable region CDR2 comprising SEQ ID NO:50; and a light chain variable region CDR3 comprising SEQ ID NO:11. In some embodiments, an anti-GCGR antibody comprises a heavy chain variable region CDR1 comprising SEQ ID NO:67; a heavy chain variable region CDR2 comprising SEQ ID NO:73; and a heavy chain variable region CDR3 comprising SEQ ID NO:74. In some embodiments, an anti-GCGR antibody comprises a light chain variable region CDR1 comprising SEQ ID NO:75; a light chain variable region CDR2 comprising SEQ ID NO:50; and a light chain variable region CDR3 comprising SEQ ID NO:11. In some embodiments, an anti-GCGR antibody comprises (a) a heavy chain variable region CDR1 comprising SEQ ID NO:67; a heavy chain variable region CDR2 comprising SEQ ID NO:73; and a heavy chain variable region CDR3 comprising SEQ ID NO:74; and (b) a light chain variable region CDR1 comprising SEQ ID NO:75; a light chain variable region CDR2 comprising SEQ ID NO:50; and a light chain variable region CDR3 comprising SEQ ID NO:11.

In some embodiments, an anti-GCGR antibody comprises a heavy chain variable region having at least about 80% sequence identity to SEQ ID NO:12. In some embodiments, an anti-GCGR antibody comprises a light chain variable region having at least about 80% sequence identity to SEQ ID NO:13. In some embodiments, an anti-GCGR antibody comprises a heavy chain variable region having at least about 80% sequence identity to SEQ ID NO:12 and/or a light chain variable region having at least 80% sequence identity to SEQ ID NO:13. In some embodiments, an anti-GCGR antibody comprises a heavy chain variable region having at least about 85%, at least about 90%, at least about 95%, at least about 97%, or at least about 99% sequence identity to SEQ ID NO:12. In some embodiments, an anti-GCGR antibody comprises a light chain variable region having at least about 85%, at least about 90%, at least about 95%, at least about 97%, or at least about 99% sequence identity to SEQ ID NO:13. In some embodiments, an anti-GCGR antibody comprises a heavy chain variable region having at least about 95% sequence identity to SEQ ID NO:12 and/or a light chain variable region having at least about 95% sequence identity to SEQ ID NO:13. In some embodiments, an anti-GCGR antibody comprises a heavy chain variable region comprising SEQ ID NO:12 and/or a light chain variable region comprising SEQ ID NO:13. In some embodiments, an anti-GCGR antibody comprises a heavy chain variable region comprising SEQ ID NO:12. In some embodiments, an anti-GCGR antibody comprises a light chain variable region comprising SEQ ID NO:13. In some embodiments, an anti-GCGR antibody comprises a heavy chain variable region comprising SEQ ID NO:12 and a light chain variable region comprising SEQ ID NO:13. In some embodiments, an anti-GCGR antibody comprises a heavy chain variable region consisting of SEQ ID NO:12 and a light chain variable region consisting of SEQ ID NO:13.

In some embodiments, an anti-GCGR antibody comprises a heavy chain variable region having at least about 80% sequence identity to SEQ ID NO:22. In some embodiments, an anti-GCGR antibody comprises a light chain variable region having at least about 80% sequence identity to SEQ ID NO:23. In some embodiments, an anti-GCGR antibody comprises a heavy chain variable region having at least about 80% sequence identity to SEQ ID NO:22 and/or a light chain variable region having at least 80% sequence identity to SEQ ID NO:23. In some embodiments, an anti-GCGR antibody comprises a heavy chain variable region having at least about 85%, at least about 90%, at least about 95%, at least about 97%, or at least about 99% sequence identity to SEQ ID NO:22. In some embodiments, an anti-GCGR antibody comprises a light chain variable region having at least about 85%, at least about 90%, at least about 95%, at least about 97%, or at least about 99% sequence identity to SEQ ID NO:23. In some embodiments, an anti-GCGR antibody comprises a heavy chain variable region having at least about 95% sequence identity to SEQ ID NO:22 and/or a light chain variable region having at least about 95% sequence identity to SEQ ID NO:23. In some embodiments, an anti-GCGR antibody comprises a heavy chain variable region comprising SEQ ID NO:22 and/or a light chain variable region comprising SEQ ID NO:23. In some embodiments, an anti-GCGR antibody comprises a heavy chain variable region comprising SEQ ID NO:22. In some embodiments, an anti-GCGR antibody comprises a light chain variable region comprising SEQ ID NO:23. In some embodiments, an anti-GCGR antibody comprises a heavy chain variable region comprising SEQ ID NO:22 and a light chain variable region comprising SEQ ID NO:23. In some embodiments, an anti-GCGR antibody comprises a heavy chain variable region consisting of SEQ ID NO:22 and a light chain variable region consisting of SEQ ID NO:23.

In some embodiments, an anti-GCGR antibody comprises a heavy chain variable region having at least about 80% sequence identity to SEQ ID NO:28. In some embodiments, an anti-GCGR antibody comprises a light chain variable region having at least 80% sequence identity to SEQ ID NO:29. In some embodiments, an anti-GCGR antibody comprises a heavy chain variable region having at least about 80% sequence identity to SEQ ID NO:28 and/or a light chain variable region having at least 80% sequence identity to SEQ ID NO:29. In some embodiments, an anti-GCGR antibody comprises a heavy chain variable region having at least about 85%, at least about 90%, at least about 95%, at least about 97%, or at least about 99% sequence identity to SEQ ID NO:28. In some embodiments, an anti-GCGR antibody comprises a light chain variable region having at least about 85%, at least about 90%, at least about 95%, at least about 97%, or at least about 99% sequence identity to SEQ ID NO:29. In some embodiments, an anti-GCGR antibody comprises a heavy chain variable region having at least about 95% sequence identity to SEQ ID NO:28 and/or a light chain variable region having at least about 95% sequence identity to SEQ ID NO:29. In some embodiments, an anti-GCGR antibody comprises a heavy chain variable region comprising SEQ ID NO:28 and/or a light chain variable region comprising SEQ ID NO:29. In some embodiments, an anti-GCGR antibody comprises a heavy chain variable region comprising SEQ ID NO:28. In some embodiments, an anti-GCGR antibody comprises a light chain variable region comprising SEQ ID NO:29. In some embodiments, an anti-GCGR antibody comprises a heavy chain variable region comprising SEQ ID NO:28 and a light chain variable region comprising SEQ ID NO:29. In some embodiments, an anti-GCGR antibody comprises a heavy chain variable region consisting of SEQ ID NO:28 and a light chain variable region consisting of SEQ ID NO:29.

In some embodiments, an anti-GCGR antibody comprises a heavy chain variable region having at least about 80% sequence identity to SEQ ID NO:36. In some embodiments, an anti-GCGR antibody comprises a light chain variable region having at least 80% sequence identity to SEQ ID NO:37. In some embodiments, an anti-GCGR antibody comprises a heavy chain variable region having at least about 80% sequence identity to SEQ ID NO:36 and/or a light chain variable region having at least 80% sequence identity to SEQ ID NO:37. In some embodiments, an anti-GCGR antibody comprises a heavy chain variable region having at least about 85%, at least about 90%, at least about 95%, at least about 97%, or at least about 99% sequence identity to SEQ ID NO:36. In some embodiments, an anti-GCGR antibody comprises a light chain variable region having at least about 85%, at least about 90%, at least about 95%, at least about 97%, or at least about 99% sequence identity to SEQ ID NO:37. In some embodiments, an anti-GCGR antibody comprises a heavy chain variable region having at least about 95% sequence identity to SEQ ID NO:36 and/or a light chain variable region having at least about 95% sequence identity to SEQ ID NO:37. In some embodiments, an anti-GCGR antibody comprises a heavy chain variable region comprising SEQ ID NO:36 and/or a light chain variable region comprising SEQ ID NO:37. In some embodiments, an anti-GCGR antibody comprises a heavy chain variable region comprising SEQ ID NO:36. In some embodiments, an anti-GCGR antibody comprises a light chain variable region comprising SEQ ID NO:37. In some embodiments, an anti-GCGR antibody comprises a heavy chain variable region comprising SEQ ID NO:36 and a light chain variable region comprising SEQ ID NO:37. In some embodiments, an anti-GCGR antibody comprises a heavy chain variable region consisting of SEQ ID NO:36 and a light chain variable region consisting of SEQ ID NO:37.

In some embodiments, an anti-GCGR antibody comprises a heavy chain variable region having at least about 80% sequence identity to SEQ ID NO:44. In some embodiments, an anti-GCGR antibody comprises a light chain variable region having at least 80% sequence identity to SEQ ID NO:45. In some embodiments, an anti-GCGR antibody comprises a heavy chain variable region having at least about 80% sequence identity to SEQ ID NO:44 and/or a light chain variable region having at least 80% sequence identity to SEQ ID NO:45. In some embodiments, an anti-GCGR antibody comprises a heavy chain variable region having at least about 85%, at least about 90%, at least about 95%, at least about 97%, or at least about 99% sequence identity to SEQ ID NO:44. In some embodiments, an anti-GCGR antibody comprises a light chain variable region having at least about 85%, at least about 90%, at least about 95%, at least about 97%, or at least about 99% sequence identity to SEQ ID NO:45. In some embodiments, an anti-GCGR antibody comprises a heavy chain variable region having at least about 95% sequence identity to SEQ ID NO:44 and/or a light chain variable region having at least about 95% sequence identity to SEQ ID NO:45. In some embodiments, an anti-GCGR antibody comprises a heavy chain variable region comprising SEQ ID NO:44 and/or a light chain variable region comprising SEQ ID NO:45. In some embodiments, an anti-GCGR antibody comprises a heavy chain variable region comprising SEQ ID NO:44. In some embodiments, an anti-GCGR antibody comprises a light chain variable region comprising SEQ ID NO:45. In some embodiments, an anti-GCGR antibody comprises a heavy chain variable region comprising SEQ ID NO:44 and a light chain variable region comprising SEQ ID NO:45. In some embodiments, an anti-GCGR antibody comprises a heavy chain variable region consisting of SEQ ID NO:44 and a light chain variable region consisting of SEQ ID NO:45.

In some embodiments, an anti-GCGR antibody comprises a heavy chain variable region having at least about 80% sequence identity to SEQ ID NO:51. In some embodiments, an anti-GCGR antibody comprises a light chain variable region having at least 80% sequence identity to SEQ ID NO:52. In some embodiments, an anti-GCGR antibody comprises a heavy chain variable region having at least about 80% sequence identity to SEQ ID NO:51 and/or a light chain variable region having at least 80% sequence identity to SEQ ID NO:52. In some embodiments, an anti-GCGR antibody comprises a heavy chain variable region having at least about 85%, at least about 90%, at least about 95%, at least about 97%, or at least about 99% sequence identity to SEQ ID NO:51. In some embodiments, an anti-GCGR antibody comprises a light chain variable region having at least about 85%, at least about 90%, at least about 95%, at least about 97%, or at least about 99% sequence identity to SEQ ID NO:52. In some embodiments, an anti-GCGR antibody comprises a heavy chain variable region having at least about 95% sequence identity to SEQ ID NO:51 and/or a light chain variable region having at least about 95% sequence identity to SEQ ID NO:52. In some embodiments, an anti-GCGR antibody comprises a heavy chain variable region comprising SEQ ID NO:51 and/or a light chain variable region comprising SEQ ID NO:52. In some embodiments, an anti-GCGR antibody comprises a heavy chain variable region comprising SEQ ID NO:51. In some embodiments, an anti-GCGR antibody comprises a light chain variable region comprising SEQ ID NO:52. In some embodiments, an anti-GCGR antibody comprises a heavy chain variable region comprising SEQ ID NO:51 and a light chain variable region comprising SEQ ID NO:52. In some embodiments, an anti-GCGR antibody comprises a heavy chain variable region consisting of SEQ ID NO:51 and a light chain variable region consisting of SEQ ID NO:52.

In some embodiments, an anti-GCGR antibody comprises a heavy chain variable region having at least about 80% sequence identity to SEQ ID NO:57. In some embodiments, an anti-GCGR antibody comprises a light chain variable region having at least 80% sequence identity to SEQ ID NO:58. In some embodiments, an anti-GCGR antibody comprises a heavy chain variable region having at least about 80% sequence identity to SEQ ID NO:57 and/or a light chain variable region having at least 80% sequence identity to SEQ ID NO:58. In some embodiments, an anti-GCGR antibody comprises a heavy chain variable region having at least about 85%, at least about 90%, at least about 95%, at least about 97%, or at least about 99% sequence identity to SEQ ID NO:57. In some embodiments, an anti-GCGR antibody comprises a light chain variable region having at least about 85%, at least about 90%, at least about 95%, at least about 97%, or at least about 99% sequence identity to SEQ ID NO:58. In some embodiments, an anti-GCGR antibody comprises a heavy chain variable region having at least about 95% sequence identity to SEQ ID NO:57 and/or a light chain variable region having at least about 95% sequence identity to SEQ ID NO:58. In some embodiments, an anti-GCGR antibody comprises a heavy chain variable region comprising SEQ ID NO:57 and/or a light chain variable region comprising SEQ ID NO:58. In some embodiments, an anti-GCGR antibody comprises a heavy chain variable region comprising SEQ ID NO:57. In some embodiments, an anti-GCGR antibody comprises a light chain variable region comprising SEQ ID NO:58. In some embodiments, an anti-GCGR antibody comprises a heavy chain variable region comprising SEQ ID NO:57 and a light chain variable region comprising SEQ ID NO:58. In some embodiments, an anti-GCGR antibody comprises a heavy chain variable region consisting of SEQ ID NO:57 and a light chain variable region consisting of SEQ ID NO:58.

In some embodiments, an anti-GCGR antibody comprises a heavy chain variable region having at least about 80% sequence identity to SEQ ID NO:65. In some embodiments, an anti-GCGR antibody comprises a light chain variable region having at least 80% sequence identity to SEQ ID NO:66. In some embodiments, an anti-GCGR antibody comprises a heavy chain variable region having at least about 80% sequence identity to SEQ ID NO:65 and/or a light chain variable region having at least 80% sequence identity to SEQ ID NO:66. In some embodiments, an anti-GCGR antibody comprises a heavy chain variable region having at least about 85%, at least about 90%, at least about 95%, at least about 97%, or at least about 99% sequence identity to SEQ ID NO:65. In some embodiments, an anti-GCGR antibody comprises a light chain variable region having at least about 85%, at least about 90%, at least about 95%, at least about 97%, or at least about 99% sequence identity to SEQ ID NO:66. In some embodiments, an anti-GCGR antibody comprises a heavy chain variable region having at least about 95% sequence identity to SEQ ID NO:65 and/or a light chain variable region having at least about 95% sequence identity to SEQ ID NO:66. In some embodiments, an anti-GCGR antibody comprises a heavy chain variable region comprising SEQ ID NO:65 and/or a light chain variable region comprising SEQ ID NO:66. In some embodiments, an anti-GCGR antibody comprises a heavy chain variable region comprising SEQ ID NO:65. In some embodiments, an anti-GCGR antibody comprises a light chain variable region comprising SEQ ID NO:66. In some embodiments, an anti-GCGR antibody comprises a heavy chain variable region comprising SEQ ID NO:65 and a light chain variable region comprising SEQ ID NO:66. In some embodiments, an anti-GCGR antibody comprises a heavy chain variable region consisting of SEQ ID NO:65 and a light chain variable region consisting of SEQ ID NO:66.

In some embodiments, an anti-GCGR antibody comprises a heavy chain variable region having at least about 80% sequence identity to SEQ ID NO:71. In some embodiments, an anti-GCGR antibody comprises a light chain variable region having at least 80% sequence identity to SEQ ID NO:72. In some embodiments, an anti-GCGR antibody comprises a heavy chain variable region having at least about 80% sequence identity to SEQ ID NO:71 and/or a light chain variable region having at least 80% sequence identity to SEQ ID NO:72. In some embodiments, an anti-GCGR antibody comprises a heavy chain variable region having at least about 85%, at least about 90%, at least about 95%, at least about 97%, or at least about 99% sequence identity to SEQ ID NO:71. In some embodiments, an anti-GCGR antibody comprises a light chain variable region having at least about 85%, at least about 90%, at least about 95%, at least about 97%, or at least about 99% sequence identity to SEQ ID NO:72. In some embodiments, an anti-GCGR antibody comprises a heavy chain variable region having at least about 95% sequence identity to SEQ ID NO:71 and/or a light chain variable region having at least about 95% sequence identity to SEQ ID NO:72. In some embodiments, an anti-GCGR antibody comprises a heavy chain variable region comprising SEQ ID NO:71 and/or a light chain variable region comprising SEQ ID NO:72. In some embodiments, an anti-GCGR antibody comprises a heavy chain variable region comprising SEQ ID NO:71. In some embodiments, an anti-GCGR antibody comprises a light chain variable region comprising SEQ ID NO:72. In some embodiments, an anti-GCGR antibody comprises a heavy chain variable region comprising SEQ ID NO:71 and a light chain variable region comprising SEQ ID NO:72. In some embodiments, an anti-GCGR antibody comprises a heavy chain variable region consisting of SEQ ID NO:71 and a light chain variable region consisting of SEQ ID NO:72.

In some embodiments, an anti-GCGR antibody comprises a heavy chain variable region having at least about 80% sequence identity to SEQ ID NO:76. In some embodiments, an anti-GCGR antibody comprises a light chain variable region having at least 80% sequence identity to SEQ ID NO:77. In some embodiments, an anti-GCGR antibody comprises a heavy chain variable region having at least about 80% sequence identity to SEQ ID NO:76 and/or a light chain variable region having at least 80% sequence identity to SEQ ID NO:77. In some embodiments, an anti-GCGR antibody comprises a heavy chain variable region having at least about 85%, at least about 90%, at least about 95%, at least about 97%, or at least about 99% sequence identity to SEQ ID NO:76. In some embodiments, an anti-GCGR antibody comprises a light chain variable region having at least about 85%, at least about 90%, at least about 95%, at least about 97%, or at least about 99% sequence identity to SEQ ID NO:77. In some embodiments, an anti-GCGR antibody comprises a heavy chain variable region having at least about 95% sequence identity to SEQ ID NO:76 and/or a light chain variable region having at least about 95% sequence identity to SEQ ID NO:77. In some embodiments, an anti-GCGR antibody comprises a heavy chain variable region comprising SEQ ID NO:76 and/or a light chain variable region comprising SEQ ID NO:77. In some embodiments, an anti-GCGR antibody comprises a heavy chain variable region comprising SEQ ID NO:76 and a light chain variable region comprising SEQ ID NO:77. In some embodiments, an anti-GCGR antibody comprises a heavy chain variable region comprising SEQ ID NO:76. In some embodiments, an anti-GCGR antibody comprises a light chain variable region comprising SEQ ID NO:77. In some embodiments, an anti-GCGR antibody comprises a heavy chain variable region consisting of SEQ ID NO:76 and a light chain variable region consisting of SEQ ID NO:77.

In some embodiments, an anti-GCGR antibody is a humanized version of any one of the antibodies disclosed herein. In some embodiments, an anti-GCGR antibody is a humanized version of the antibody 6B5, 3H5, 5B11, 1C1, 1C3, 1H2, 4F8, 13G9, 14F4, or 14E9. In some embodiments, an anti-GCGR antibody is a humanized version of the antibody 6B5, for example, Hz6B5. In some embodiments, an anti-GCGR antibody comprises a heavy chain variable region having at least about 80% sequence identity to SEQ ID NO:14 and/or a light chain variable region having at least 80% sequence identity to SEQ ID NO:15. In some embodiments, an anti-GCGR antibody comprises a heavy chain variable region having at least about 85%, at least about 90%, at least about 95%, at least about 97%, or at least about 99% sequence identity to SEQ ID NO:14. In some embodiments, an anti-GCGR antibody comprises a light chain variable region having at least about 85%, at least about 90%, at least about 95%, at least about 97%, or at least about 99% sequence identity to SEQ ID NO:15. In some embodiments, an anti-GCGR antibody comprises a heavy chain variable region having at least about 95% sequence identity to SEQ ID NO:14 and/or a light chain variable region having at least about 95% sequence identity to SEQ ID NO:15. In some embodiments, an anti-GCGR antibody comprises a heavy chain variable region comprising SEQ ID NO:14 and/or a light chain variable region comprising SEQ ID NO:15. In some embodiments, an anti-GCGR antibody comprises a heavy chain variable region comprising SEQ ID NO:14. In some embodiments, an anti-GCGR antibody comprises a light chain variable region comprising SEQ ID NO:15. In some embodiments, an anti-GCGR antibody comprises a heavy chain variable region comprising SEQ ID NO:14 and a light chain variable region comprising SEQ ID NO:15. In some embodiments, an anti-GCGR antibody comprises a heavy chain variable region consisting of SEQ ID NO:14 and a light chain variable region consisting of SEQ ID NO:15.

In some embodiments, the GCGR-binding agents described herein comprise antibodies (e.g., full-length antibodies) in which at least one or more of the constant region domains has been modified or deleted. In some embodiments, the antibodies may comprise modifications to one or more of the three heavy chain constant region domains (CH1, CH2 or CH3) and/or to the light chain constant region (CL). In some embodiments, the heavy chain constant region of the modified antibodies comprises at least one human constant region domain. In some embodiments, the heavy chain constant region of the modified antibodies comprises more than one human constant region domain. In some embodiments, modifications to the constant region comprise additions, deletions, or substitutions of one or more amino acids in one or more domains. In some embodiments, one or more domains are partially or entirely deleted from the constant regions of the modified antibodies. In some embodiments, the entire CH2 domain has been removed from an antibody (ΔCH2 constructs). In some embodiments, a deleted constant region domain is replaced by a short amino acid spacer that provides some of the molecular flexibility typically imparted by the absent constant region domain. In some embodiments, a modified antibody comprises a CH3 domain directly fused to the hinge region of the antibody. In some embodiments, a modified antibody comprises a peptide spacer inserted between the hinge region and modified CH2 and/or CH3 domain.

It is known in the art that the constant region(s) of an antibody mediates several effector functions. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can be involved in autoimmune hypersensitivity. In addition, the Fc region of an antibody can bind a cell expressing a Fc receptor (FcR). There are a number of Fc receptors that are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell cytotoxicity or ADCC), release of inflammatory mediators, placental transfer, and control of immunoglobulin production.

In some embodiments, an antibody comprises a variant Fc region. The amino acid sequences of the Fc region of human IgG1, IgG2, IgG3, and IgG4 are known to those of ordinary skill in the art (e.g., Fc region of human IgG1—approximately aa 104-330 of SEQ ID NO:82). Fc regions with amino acid variations have been identified in native antibodies. In some embodiments, a variant Fc region is engineered with substitutions at specific amino acid positions as compared to a native Fc region (e.g., SEQ ID NO:83 and SEQ ID NO:84).

In some embodiments, the modified antibodies provide for altered effector functions that, in turn, affect the biological profile of the administered antibody. For example, in some embodiments, the deletion or inactivation (through point mutations or other means) of a constant region may reduce Fc receptor binding of the circulating modified antibody. In some embodiments, the constant region modifications increase the serum half-life of the antibody. In some embodiments, the constant region modifications reduce the serum half-life of the antibody. In some embodiments, the constant region modifications enhance or increase ADCC and/or complement-dependent cytotoxicity (CDC) of the antibody. In some embodiments, the constant region modifications decrease or remove ADCC and/or CDC of the antibody. For example, specific amino acid substitutions in a human IgG1 Fc region with corresponding IgG2 or IgG4 residues may reduce effector functions (e.g., ADCC and/or CDC) in the modified antibody. Thus, in some embodiments, an antibody does not have one or more effector functions. In some embodiments, the antibody has no ADCC activity and/or no CDC activity. In some embodiments, the antibody does not bind an Fc receptor and/or complement factors. In some embodiments, the antibody has no effector function(s). In some embodiments, the constant region is modified to eliminate disulfide linkages or oligosaccharide moieties. In some embodiments, the constant region is modified to add/substitute one or more amino acids to provide, for example, one or more cytotoxin or carbohydrate attachment sites. In this respect, it may be possible to disrupt the activity or effector function provided by a specific sequence or region while substantially maintaining the structure, binding activity, and other desired characteristics of the modified antibody.

Modifications to the constant region of antibodies described herein may be made using well known biochemical or molecular engineering techniques. In some embodiments, antibody variants can be prepared by introducing appropriate nucleotide changes into the encoding DNA, and/or by synthesis of the desired antibody or polypeptide.

The present disclosure further embraces additional variants and equivalents that are substantially homologous to the recombinant, monoclonal, chimeric, humanized, and human antibodies, or antibody fragments thereof, described herein. In some embodiments, it may be desirable to improve the binding affinity of the antibody. In some embodiments, it may be desirable to modulate other biological properties of the antibody, including but not limited to, specificity, thermostability, expression level, effector function(s), glycosylation, immunogenicity, and/or solubility. Those skilled in the art will appreciate that some amino acid changes may alter post-translational modifications of an antibody, such as changing the number or position of glycosylation sites or altering membrane anchoring characteristics.

Variations may be a substitution, deletion, or insertion of one or more nucleotides encoding the antibody or polypeptide that results in a change in the amino acid sequence as compared with the native antibody or polypeptide sequence. Amino acid substitutions can be the result of replacing one amino acid with another amino acid having similar structural and/or chemical properties, such as the replacement of a leucine with a serine, e.g., conservative amino acid replacements. Insertions or deletions may optionally be in the range of about 1 to 5 amino acids. In some embodiments, the substitution, deletion, or insertion comprises less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the parent molecule. Variations in the amino acid sequence that are biologically useful and/or relevant may be determined by systematically making insertions, deletions, or substitutions in the sequence and testing the resulting variant proteins for activity as compared to the parental protein.

In some embodiments, variants may include addition of amino acid residues at the amino- and/or carboxyl-terminal end of the antibody or polypeptide. The length of additional amino acids residues may range from one residue to a hundred or more residues. In some embodiments, a variant comprises an N-terminal methionyl residue. In some embodiments, the variant comprises an additional polypeptide/protein, i.e., a fusion protein. In some embodiments, a variant comprises a detectable label and/or protein (e.g., an enzyme).

In some embodiments, a cysteine residue not involved in maintaining the proper conformation of an antibody may be substituted or deleted to modulate the antibody's characteristics, for example, to improve oxidative stability and/or prevent aberrant disulfide crosslinking. Conversely, in some embodiments, one or more cysteine residues may be added to create disulfide bond(s) to improve stability.

In some embodiments, an antibody of the present disclosure is "deimmunized". The deimmunization of antibodies generally consists of introducing specific amino acid mutations (e.g., substitutions, deletions, additions) to remove T-cell epitopes without significantly reducing the binding affinity or other desired activities of the antibody.

The variant antibodies or polypeptides described herein may be generated using methods known in the art, including but not limited to, site-directed mutagenesis, alanine scanning mutagenesis, and PCR mutagenesis.

In some embodiments, a GCGR antagonist (e.g., an anti-GCGR antibody) described herein is chemically modified. In some embodiments, a GCGR antagonist is an antibody that has been chemically modified by glycosylation, acetylation, pegylation, phosphorylation, amidation, derivatization by known protecting/blocking groups, proteolytic cleavage, and/or linkage to another protein. Any of numerous chemical modifications may be carried out by known techniques.

The present disclosure encompasses agents built upon non-immunoglobulin backbones, wherein the agents bind to the same epitope or essentially the same epitope as an anti-GCGR antibody disclosed herein. In some embodiments, a non-immunoglobulin-based binding agent is a protein that competes with an anti-GCGR antibody described herein in a competitive binding assay. In some embodiments, an alternative binding agent comprises a scaffold protein. Generally, scaffold proteins can be assigned to one of three groups based on the architecture of their backbone: (1) scaffolds consisting of α-helices; (2) small scaffolds with few secondary structures or an irregular architecture of α-helices and β-sheets; and (3) scaffolds consisting of predominantly β-sheets. Scaffold proteins include, but are not limited to, anticalins, which are based upon the lipocalin scaffold; adnectins, which are based on the 10$^{th}$ domain of human fibronectin type 3; affibodies, which are based on the B-domain in the Ig-binding region of *Staphylococcus aureus* protein A; darpins, which are based on ankyrin repeat domain proteins; fynomers, which are based on the SH3 domain of the human Fyn protein kinase; affitins, which are based on Sac7d from *Sulfolobus acidocaldarius*; affilins, which are based on human γ-B-crystallin or human ubiquitin; avimers, which are based on the A-domains of membrane receptor proteins; knottins (cysteine knot miniproteins), which are based upon a stable 30-amino acid anti-parallel β-strand protein fold; and Kunitz domain inhibitor scaffolds, which are based upon a structure that contains three disulfide bonds and three loops. In some embodiments, a GCGR-binding agent comprises an engineered scaffold protein comprising one or more CDRs from an antibody defined in Tables 1-10. In some embodiments, a GCGR-binding agent comprises an engineered scaffold protein comprising the heavy chain variable region CDR1, CDR2, and CD3 and the light chain variable region CDR1, CDR2, and CDR3 from Table 1. In some embodiments, a GCGR-binding agent comprises an engineered scaffold protein comprising the heavy chain variable region CDR1, CDR2, and CD3 and the light chain variable region CDR1, CDR2, and CDR3 from Table 2. In some embodiments, a GCGR-binding agent comprises an engineered scaffold protein comprising the heavy chain variable region CDR1, CDR2, and CD3 and the light chain variable region CDR1, CDR2, and CDR3 from Table 3. In some embodiments, a GCGR-binding agent comprises an engineered scaffold protein comprising the heavy chain variable region CDR1, CDR2, and CD3 and the light chain variable region CDR1, CDR2, and CDR3 from Table 4. In some embodiments, a GCGR-binding agent comprises an engineered scaffold protein comprising the heavy chain variable region CDR1, CDR2, and CD3 and the light chain variable region CDR1, CDR2, and CDR3 from Table 5. In some embodiments, a GCGR-binding agent comprises an engineered scaffold protein comprising the heavy chain variable region CDR1, CDR2, and CD3 and the light chain variable region CDR1, CDR2, and CDR3 from Table 6. In some embodiments, a GCGR-binding agent comprises an engineered scaffold protein comprising the heavy chain variable region CDR1, CDR2, and CD3 and the light chain variable region CDR1, CDR2, and CDR3 from Table 7. In some embodiments, a GCGR-binding agent comprises an engineered scaffold protein comprising the heavy chain variable region CDR1, CDR2, and CD3 and the light chain variable region CDR1, CDR2, and CDR3 from Table 8. In some embodiments, a GCGR-binding agent comprises an engineered scaffold protein comprising the heavy chain variable region CDR1, CDR2, and CD3 and the light chain variable region CDR1, CDR2, and CDR3 from Table 9. In some embodiments, a GCGR-binding agent comprises an engineered scaffold protein comprising the heavy chain variable region CDR1, CDR2, and CD3 and the light chain variable region CDR1, CDR2, and CDR3 from Table 10.

Generally speaking, antigen-antibody interactions are non-covalent and reversible, formed by a combination of hydrogen bonds, hydrophobic interactions, electrostatic and van der Waals forces. When describing the strength of an antigen-antibody complex, affinity and/or avidity are usually mentioned. The binding of an antibody to its antigen is a reversible process, and the affinity of the binding is typically reported as an equilibrium dissociation constant ($K_D$). $K_D$ is the ratio of an antibody dissociation rate ($k_{off}$) (how quickly it dissociates from its antigen) to the antibody association rate ($k_{on}$) (how quickly it binds to its antigen). In some embodiments, $K_D$ values are determined by measuring the $k_{on}$ and $k_{off}$ rates of a specific antibody/antigen interaction and then using a ratio of these values to calculate the $K_D$ value. $K_D$ values may be used to evaluate and rank order the strength of individual antibody/antigen interactions. The lower the $K_D$ of an antibody, the higher the affinity of the antibody for its target. Avidity gives a measure of the overall strength of an antibody-antigen complex. It is dependent on three major parameters: (i) affinity of the antibody for the epitope, (ii) valency of both the antibody and antigen, and (iii) structural arrangement of the parts that interact.

In some embodiments, a GCGR-binding agent (e.g., an antibody) binds GCGR with a dissociation constant ($K_D$) of about 1 µM or less, about 100 nM or less, about 40 nM or less, about 20 nM or less, about 10 nM or less, about 1 nM or less, about 0.1 nM or less, 50 pM or less, 10 pM or less, or 1 pM or less. In some embodiments, a GCGR-binding agent binds GCGR with a $K_D$ of about 20 nM or less. In some embodiments, a GCGR-binding agent binds GCGR with a $K_D$ of about 10 nM or less. In some embodiments, a GCGR-binding agent binds GCGR with a KD of about 5 nM or less. In some embodiments, a GCGR-binding agent binds GCGR with a KD of about 3 nM or less. In some embodiments, a GCGR-binding agent binds GCGR with a KD of about 2 nM or less. In some embodiments, a GCGR-binding agent binds GCGR with a $K_D$ of about 1 nM or less. In some embodiments, a GCGR-binding agent binds GCGR with a $K_D$ of about 0.5 nM or less. In some embodiments, a GCGR-binding agent binds GCGR with a $K_D$ of about 0.1 nM or less. In some embodiments, a GCGR-binding agent binds GCGR with a $K_D$ of about 50 pM or less. In some embodiments, a GCGR-binding agent binds GCGR with a $K_D$ of about 25 pM or less. In some embodiments, a GCGR-binding agent binds GCGR with a $K_D$ of about 10 pM or less. In some embodiments, a GCGR-binding agent binds GCGR with a $K_D$ of about 1 pM or less. In some embodiments, a GCGR-binding agent binds GCGR with a KD of about 0.01 nM to about 2.5 nM. In some embodiments, a GCGR-binding agent binds GCGR with a KD of about 0.1 nM to about 5 nM. In some embodiments, a GCGR-binding agent binds GCGR with a KD of about 1 nM to about 5 nM. In some embodiments, the dissociation constant of the binding agent (e.g., an antibody) to GCGR is the dissociation constant determined using a GCGR fusion protein comprising at least a portion or fragment of GCGR immobilized on a Biacore chip. In some embodiments, the dissociation constant of the binding agent (e.g., an antibody) to GCGR is the dissociation constant determined using the extracellular domain of GCGR (or a portion/fragment of the extracellular domain) immobilized on a Biacore chip. In some embodiments, the dissociation constant of the binding agent (e.g., an antibody) to GCGR is the dissociation constant determined using the binding agent captured by an anti-human IgG antibody on a Biacore chip and soluble GCGR or a fragment thereof.

In some embodiments, a GCGR-binding agent (e.g., an antibody) binds GCGR with a half maximal effective concentration (EC50) of about 1 µM or less, about 100 nM or less, about 40 nM or less, about 20 nM or less, about 10 nM or less, about 1 nM or less, or about 0.1 nM or less. In some embodiments, a GCGR-binding agent binds to human GCGR with an EC50 of about 1 µM or less, about 100 nM or less, about 40 nM or less, about 20 nM or less, about 10 nM or less, about 1 nM or less, or about 0.1 nM or less. In some embodiments, a GCGR-binding agent binds mouse GCGR and/or human GCGR with an EC50 of about 40 nM or less, about 20 nM or less, about 10 nM or less, about 1 nM or less or about 0.1 nM or less.

The binding agents (e.g., antibodies) described herein can be produced by any suitable method known in the art. Such methods range from direct protein synthesis methods to constructing a DNA sequence encoding polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional variants thereof. In some embodiments, a DNA sequence encoding a polypeptide of interest is constructed by chemical synthesis using an oligonucleotide synthesizer. Oligonucleotides can be designed based on the amino acid sequence of the desired polypeptide and selecting those codons that are favored in the host cell in which the recombinant polypeptide of interest will be produced. Standard methods can be applied to synthesize a polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), the polynucleotide sequences encoding a particular polypeptide of interest can be inserted into an expression vector and operatively linked to an expression control sequence appropriate for expression of the protein in a desired host. Proper assembly can be confirmed by nucleotide sequencing, restriction enzyme mapping, and/or expression of a biologically active polypeptide in a suitable host. As is well-known to those of skill in the art, in order to obtain high expression levels of a transfected gene in a host, the gene must be operatively linked to transcriptional and translational expression control sequences that are functional in the chosen expression host.

In some embodiments, recombinant expression vectors are used to amplify and express DNA encoding antibodies, or fragments thereof, against human GCGR. For example, recombinant expression vectors can be replicable DNA constructs which have synthetic or cDNA-derived DNA fragments encoding a polypeptide chain of a GCGR-binding agent, such as an anti-GCGR antibody, or an antigen-binding fragment thereof, operatively linked to suitable transcriptional and/or translational regulatory elements derived from mammalian, microbial, viral, or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can additionally be incorporated. DNA regions are "operatively linked" when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host cell. In some embodiments, in situations where recombinant protein is expressed without a leader or transport sequence, a polypeptide may include an N-terminal methionine residue. This residue can optionally be subsequently cleaved from the expressed recombinant protein to provide a final product.

The choice of an expression control sequence and an expression vector generally depends upon the choice of host. A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from *E. coli*, including pCR1, pBR322, pMB9 and their derivatives, and wider host range plasmids, such as M13 and other filamentous single-stranded DNA phages.

The GCGR-binding agents (e.g., antibodies) of the present disclosure can be expressed from one or more vectors. For example, in some embodiments, a heavy chain polypeptide is expressed by one vector and a light chain polypeptide is expressed by a second vector. In some embodiments, a heavy chain polypeptide and a light chain polypeptide are expressed by one vector.

Suitable host cells for expression of a GCGR-binding agent (e.g., an antibody) or a GCGR protein or fragment thereof to use as an antigen or immunogen include prokaryotes, yeast cells, insect cells, or higher eukaryotic cells under the control of appropriate promoters. Prokaryotes include gram-negative or gram-positive organisms, for example, *E. coli* or *Bacillus*. Higher eukaryotic cells include established cell lines of mammalian origin as described herein. Cell-free translation systems may also be employed. Appropriate cloning and expression vectors for use with bacterial, fungal, yeast, and mammalian cellular hosts, as well as methods of protein production, including antibody production are well known in the art.

Various mammalian culture systems may be used to express recombinant polypeptides.

Expression of recombinant proteins in mammalian cells may be desirable because these proteins are generally correctly folded, appropriately modified, and biologically functional. Examples of suitable mammalian host cell lines include, but are not limited to, COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), HEK-293 (human embryonic kidney-derived) cell lines and variants thereof. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences.

Expression of recombinant proteins in insect cell culture systems (e.g., baculovirus) also offers a robust method for producing correctly folded and biologically functional proteins. Baculovirus systems for production of heterologous proteins in insect cells are well known to those of skill in the art.

Thus, the present disclosure provides cells comprising the GCGR-binding agents described herein. In some embodiments, the cells produce the GCGR-binding agents described herein. In some embodiments, the cells produce an antibody. In some embodiments, the cells produce an antibody that binds human GCGR. In some embodiments, the cells produce an antibody that binds cyno GCGR. In some embodiments, the cells produce an antibody that binds human GCGR and cyno GCGR. In some embodiments, the cells produce an antibody designated 6B5, 3H5, 5B11, 1C1, 1C3, 1H2, 4F8, 13G9, 14F4, or 14E9. In some embodiments, the cells produce an antibody designated 6B5. In some embodiments, the cells produce a humanized version of antibody 6B5, referred to as Hz6B5. In some embodiments, the cell is a hybridoma cell. In some embodiments, the cell is a mammalian cell. In some embodiments, the cell is a prokaryotic cell. In some embodiments, the cell is an eukaryotic cell.

Proteins produced by a host cell can be purified according to any suitable method. Standard methods include chromatography (e.g., ion exchange, affinity, and sizing column chromatography), centrifugation, differential solubility, or by any other standard technique for protein purification. Affinity tags such as hexa-histidine (SEQ ID NO:85), maltose binding domain, influenza coat sequence, and glutathione-S-transferase can be attached to the protein to allow easy purification by passage over an appropriate affinity column. Affinity chromatography used for purifying immunoglobulins can include Protein A, Protein G, and Protein L chromatography. Isolated proteins can be physically characterized using such techniques as proteolysis, size exclusion chromatography (SEC), mass spectrometry (MS), nuclear magnetic resonance (NMR), isoelectric focusing (IEF), high performance liquid chromatography (HPLC), and x-ray crystallography. The purity of isolated proteins can be determined using techniques known to those of skill in the art, including but not limited to, SDS-PAGE, SEC, capillary gel electrophoresis, IEF, and capillary isoelectric focusing (cIEF).

In some embodiments, supernatants from expression systems that secrete recombinant protein into culture media are first concentrated using a commercially available protein concentration filter, for example, an Amicon® or Millipore Pellicon® ultrafiltration unit. Following the concentration step, the concentrate can be applied to a suitable purification matrix. In some embodiments, an anion exchange resin is employed, for example, a matrix or substrate having pendant diethylaminoethyl (DEAE) groups. The matrices can be acrylamide, agarose, dextran, cellulose, or other types commonly employed in protein purification. In some embodiments, a cation exchange step is employed. Suitable cation exchangers include various insoluble matrices comprising sulfopropyl or carboxymethyl groups. In some embodiments, a hydroxyapatite media is employed, including but not limited to, ceramic hydroxyapatite (CHT). In some embodiments, one or more reverse-phase HPLC steps employing hydrophobic RP-HPLC media, e.g., silica gel having pendant methyl or other aliphatic groups, are employed to further purify a recombinant protein. In some embodiments, hydrophobic interaction chromatography (HIC) is used to separate recombinant proteins based on their hydrophobicity. HIC is a useful separation technique for purifying proteins while maintaining biological activity due to the use of conditions and matrices that operate under less denaturing conditions than some other techniques. Some or all of the foregoing purification steps, in various combinations, can be employed to provide a homogeneous recombinant protein.

GCGR-binding agents of the present disclosure may be analyzed for their physical/chemical properties and/or biological activities by various assays known in the art. In some embodiments, a GCGR-binding agent (e.g., an anti-GCGR antibody) is evaluated for its ability to bind GCGR. Binding assays include, but are not limited to, Biacore, ELISA, and FACS.

In some embodiments, antibodies generated against GCGR are characterized based upon their binding properties. In some embodiments, antibodies are grouped together based upon the epitope each individual antibody recognizes and/or binds to, a process known as "epitope binning" Generally, in epitope binning antibodies are tested in a pairwise combinatorial manner and antibodies that compete with each other (i.e., bind the same or similar epitopes) are grouped together into bins. For example, in a binning assay, a first antibody is immobilized on a surface and a premixed solution of a second antibody and antigen/target protein is flowed over the immobilized first antibody. In tandem, the antigen/target protein is immobilized on a surface and the two antibodies are flowed over the immobilized antigen and compete to bind to the immobilized antigen/target protein. In each of these techniques, antibodies that block one another can be identified. A competitive blocking profile is created for each antibody relative to the other antibodies. The results determine which bin each antibody is placed in. High-throughput methods of epitope binning are known in the art and allow for screening and characterization of large numbers of antibodies within a short period of time. Antibodies that bind similar epitopes often share similar functions. Conversely, antibodies that bind different epitopes may have different functional activities.

Epitope mapping is the process of identifying the binding site (e.g., epitope) on a target protein where an antibody (or other binding agent) binds. A variety of methods are known in the art for mapping binding sites and/or epitopes on target proteins. These methods include mutagenesis, including but not limited to, shotgun mutagenesis, site-directed mutagenesis, and alanine scanning mutagenesis; domain or fragment scanning; peptide scanning (e.g., Pepscan technology); display methods (e.g., phage display, microbial display, and ribosome/mRNA display); methods involving proteolysis and mass spectroscopy; and structural determination (e.g., X-ray crystallography and NMR).

In some embodiments, anti-GCGR antibodies are characterized by assays including, but not limited to, N-terminal sequencing, amino acid analysis, high pressure liquid chromatography (HPLC), mass spectrometry, ion exchange chromatography, and papain digestion.

In some embodiments, a GCGR-binding agent (e.g., an anti-GCGR antibody) is tested for its ability to modulate GCGR activity. In some embodiments, assays are provided for identifying anti-GCGR antibodies that enhance GCGR activity. In some embodiments, assays are provided for identifying anti-GCGR antibodies that inhibit GCGR activity. Cyclic AMP (cAMP) is one of the most important GPCR intracellular mediators. In many cell types, cAMP production results from the regulation of adenylate cyclase by the Ga subunit of a G-protein. For example, activation of GCGR by glucagon results in production of cAMP. In some embodiments, GCGR activation can be assessed by assaying for production of cAMP and in turn, GCGR antagonists can be screened for their ability to inhibit cAMP production. For example, in some embodiments, cells are prepared and dispensed into plates and then incubated with a GCGR-binding agent (e.g., an anti-GCGR antibody). After an appropriate period of time, the cell/GCGR-binding agent mixture is incubated with glucagon. Finally, cAMP levels are determined in the cells treated with the GCGR-binding agents and compared to the cAMP levels in appropriate control cells. In some embodiments, the IC50 of a GCGR antagonist (e.g., an anti-GCGR antibody) is determined. "IC50" refers to the half maximal inhibitory concentration of an agent and is a measure of the effectiveness of the agent in inhibiting a specific biological or biochemical function.

The present disclosure also provides conjugates comprising any one of the GCGR-binding agents described herein. In some embodiments, an anti-GCGR antibody is attached to a second molecule. In some embodiments, an anti-GCGR antibody is conjugated to a cytotoxic agent or moiety. In some embodiments, an anti-GCGR antibody is conjugated to a cytotoxic agent to form an ADC (antibody-drug conjugate). In some embodiments, the cytotoxic agent is a chemotherapeutic agent including, but not limited to, methotrexate, adriamycin/doxorubicin, melphalan, mitomycin C, chlorambucil, duocarmycin, daunorubicin, pyrrolobenzodiazepines (PBDs), or other intercalating agents. In some embodiments, the cytotoxic agent is a microtubule inhibitor including, but not limited to, auristatins, maytansinoids (e.g., DMI and DM4), and tubulysins. In some embodiments, the cytotoxic agent is an enzymatically active toxin of bacterial, fungal, plant, or animal origin, or fragments thereof, including, but not limited to, diphtheria A chain, non-binding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In some embodiments, a GCGR-binding agent (e.g., an antibody) is conjugated to one or more small molecule toxins, such as calicheamicins, maytansinoids, trichothenes, and CC1065. A derivative of any of these toxins can also be used, as long as the derivative retains cytotoxic activity.

Conjugates comprising a protein (e.g., an antibody) may be made using any suitable method known in the art. In some embodiments, conjugates are made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

In some embodiments, a GCGR-binding agent (e.g., an anti-GCGR antibody) is conjugated to a detectable substance or molecule that allows the protein to be used for diagnosis and/or detection. The detectable substance may be selected from a group including but not limited to, enzymes, such as horseradish peroxidase, alkaline phosphatase, beta-galactosidase, and acetylcholinesterase; prosthetic groups, such as streptavidin/biotin and avidin/biotin; fluorescent materials, such as, umbelliferone, fluorescein, fluorescein isothiocynate, rhodamine, dichlorotriazinylamine fluorescein, dansyl chloride, and phycoerythrin; bioluminescent materials, such as luciferase, luciferin, and aequorin; chemiluminescent materials, such as luminol and acridinium; radioactive materials, such as $^{131}$I, $^{125}$I, $^{123}$I, $^{121}$I, $^{14}$C, $^{35}$S, $^{3}$H, $^{115}$In, $^{113}$In, $^{112}$In, $^{111}$In, $^{99m}$Tc, $^{201}$Ti, $^{68}$Ga, $^{67}$Ga, $^{103}$Pd, $^{99}$Mo, $^{133}$Xe, $^{18}$F, $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, $^{67}$Cu, $^{212}$Bi and $^{117}$Sn; positron emitting metals; and non-radioactive paramagnetic metal ions.

In some embodiments, a GCGR-binding agent (e.g., an anti-GCGR antibody) described herein can be conjugated to a second antibody to form an antibody heteroconjugate.

In some embodiments, a GCGR-binding agent (e.g., an anti-GCGR antibody) described herein may be attached to a solid support and used in immunoassays or for purification of the target antigen. Such solid supports include, but are not limited to, glass, cellulose, polyacrylamide, nylon, polystyrene, polyvinyl chloride, or polypropylene.

IV. Immunotherapeutic Agents

The present disclosure provides GCGR antagonists for use in combination therapy with immunotherapeutic agents for treatment of diseases, disorders, and/or conditions associated with beta cell dysfunction. In some embodiments of the methods described herein, the immunotherapeutic agent is a small molecule, a peptide, a polypeptide, an antibody, or a fusion protein. In some embodiments of the methods described herein, the immunotherapeutic agent is an immunosuppressive agent. In some embodiments of the methods described herein, the immunotherapeutic agent is an anti-inflammatory agent.

In some embodiments of the methods described herein, an immunotherapeutic agent is an interleukin antagonist and/or inhibitor. In some embodiments of the methods described herein, an immunotherapeutic agent is an interleukin receptor antagonist and/or inhibitor. In some embodiments, the immunotherapeutic agent is an interleukin-1 beta antagonist and/or inhibitor. Interleukin-1 beta antagonists and/or inhibitors include, but are not limited to, anti-IL-1-beta antibodies, canakinumab, gevokizumab, TK-002, lutkikmab, LY-2189102, APX-002, rilonacept, and HL-2351. In some embodiments, the immunotherapeutic agent is an interleukin-2 (IL-2) receptor (CD25) antagonist and/or inhibitor. IL-2 receptor antagonists and/or inhibitors include, but are not limited to, anti-CD25 antibodies, daclizumab, basiliximab, inolimomab, camidanlumab, MT-204, CHT-25, and NKTR-358. In some embodiments, the immunotherapeutic agent is an interleukin-2 derivative or mutein. IL-2 derivatives include, but are not limited to, AMG-592. In some embodiments, the immunotherapeutic agent is an interleukin-6 (IL-6) or IL-6 receptor (IL-6R) antagonist and/or inhibitor. IL-6 or IL-6R antagonists and/or inhibitors include, but are not limited to, anti-IL-6 antibodies, anti-IL-6R antibodies, tocilizumab, clazakizumab, sirukumab, silituximab, olokizumab, SA-237, MEDI-5117, and FB-704A. In some embodiments, the immunotherapeutic agent is an interleukin-17 (IL-17) antagonist and/or inhibitor. IL-17 antagonists and/or inhibitors include, but are not limited to, anti-IL-17 antibodies, ixekizumab, CAT-2200, and OREG-203. In some embodiments, the immunotherapeutic agent is an interleukin-21 (IL-21) antagonist and/or inhibitor. IL-21 antagonists and/or inhibitors include, but are not limited to, anti-IL-21 antibodies, LY-3200327, GED-0408, ATR-107, NNC0114-0005, and NNC0114-0006.

In some embodiments of the methods described herein, an immunotherapeutic agent is a TNF or TNF receptor antagonist and/or inhibitor. In some embodiments of the methods described herein, an immunotherapeutic agent is a TNF-alpha antagonist and/or inhibitor. TNF-alpha antagonists and/or inhibitors include, but are not limited to, adalimumab, certolizumab, infliximab, golimumab, afelimomab, placulumab, SSS-07, etanercept, MDL-20112, and pegsunercept.

In some embodiments of the methods described herein, an immunotherapeutic agent is an antagonist and/or inhibitor of a T-cell or a B-cell. In some embodiments of the methods described herein, an immunotherapeutic agent is an anti-CD3 antibody. Anti-CD3 antibodies include, but are not limited to, teplizumab, otelixizumab, visilizumab, foralumab, ELV-001, ES-301, and TRX-318. In some embodiments of the methods described herein, an immunotherapeutic agent is an anti-CD20 antibody. Anti-CD20 antibodies include, but are not limited to, rituximab (RITUXAN), ocrelizumab, obinutuzumab, veltuzumab, ofatumumab, tositumomab, ocaratuzumab, SCT-400, GM-04, CHO-H01, PRO-131921, MIL-62 and SM-09.

In some embodiments of the methods described herein, an immunotherapeutic agent is an anti-CD28 antibody. In some embodiments of the methods described herein, an immunotherapeutic agent is a CTLA4-Ig fusion protein (belatacept).

EXAMPLES

Example 1

Generation of Antibodies

Antibodies to glucagon receptor (GCGR) were generated by injecting mice (i) with cells expressing human GCGR or (ii) with a His-tagged soluble protein comprising the extracellular domain of human GCGR.

GCGR-expressing cells were prepared as follows. CHO 3E7 cells were transfected with a nucleic acid sequence encoding human GCGR. Cells were analyzed for expression of GCGR by FACS and positive cells were isolated. The soluble protein comprising the extracellular domain of human GCGR was generated by standard recombinant techniques and purified using the His tag. Mice were immunized with a membrane preparation of the GCGR-expressing cells or the soluble GCGR protein. Mice were boosted to induce high titers. Antibody titers in serum were determined by ELISA and FACS. Single cell suspensions of lymphocytes were obtained from the spleen and draining lymph nodes of mice with suitable titers. Lymphocytes were fused with SP2/0 myeloma cells at a ratio of 1:1 by electrofusion. Fused cells were plated into 384-well plates in the presence of HAT selection media. After 10-14 days of culture, supernatants were collected and initially screened by (i) FACS using GCGR-expressing cells or (ii) Biacore using soluble GCGR (e.g., the extracellular domain of GCGR) to identify binders.

Supernatants produced from the hybridoma fusions were screened for binding to human GCGR using CHO cells that stably expressed full length GCGR in a FACS-based binding assay or a CellInsight™ HCS platform (ThermoFischer Scientific). Briefly, hybridoma supernatants were incubated with human GCGR-expressing cells for 30 minutes at 4° C. After washing with PBS/1% BSA/0.1% azide, the cells were incubated with a labeled anti-mouse Fc antibody (Jackson Immunoresearch) for 30 minutes at 4° C. After washing with PBS/1% BSA/0.1% azide, the cells were analyzed using (i) a flow cytometer (BD FACSCalibur instrument) and cytometric analytical software (FlowJo) or (ii) a CellInsight™ Platform.

In addition, supernatants were screened for binding to human GCGR using a Biacore SPR system. Briefly, anti-mouse Fc antibody (Sigma-Aldrich) was immobilized on all four flow cells of a CM5 chip using amine coupling reagents (GE Healthcare LifeSciences). Hybridoma supernatants were diluted three-fold with PBS-P buffer (PBS containing 0.005% P20-PBS-P) and injected for 30 seconds over flow cells 2, 3 and 4 to capture the test antibodies and using flow cell 1 as a reference. The next step was an injection of soluble human GCGR extracellular domain (100 nM in PBS-P buffer) at a flow rate of 50 µL/min and monitoring of the binding kinetics at 25° C. Kinetic data were collected over time and fit using the simultaneous global fit equation to yield affinity constants ($K_D$ values) for each antibody.

More than 1500 antibodies were identified as binding to human GCGR. A subset of the antibodies that bound to GCGR were purified and re-tested for their binding affinities to human GCGR.

Representative results are reported as $K_D$ (nM) values as shown in Table 11.

TABLE 11

| Anti-GCGR Antibody | $K_D$ (nM) |
|---|---|
| 6B5 | 0.2 |
| 3H5 | 2.2 |
| 5B11 | 1.2 |
| 1C1 | 1.9 |
| 1C3 | 1.4 |
| 1H2 | 3.7 |
| 4F8 | 0.5 |
| 13G9 | 0.2 |
| 14F4 | 0.6 |
| 14E9 | 0.8 |

Several of the anti-GCGR antibodies were selected for sequence analysis including the ten antibodies listed in Table 11. CDR sequences for these ten antibodies are shown in Tables 1-10. An exemplary anti-GCGR antibody, 6B5, was selected for humanization and Hz6B5 was generated.

Example 2

Combination Treatment with Anti-GCGR Antibody and Immunotherapeutic Agent

An exemplary anti-GCGR antibody in combination with an immunotherapeutic agent was evaluated in a mouse model. Non-obese diabetic (NOD) mice are commonly used as an animal model for Type 1 diabetes. Diabetes in NOD mice is characterized by insulitis, a leukocytic infiltrate of the pancreatic islets. Marked decreases in pancreatic insulin content occur in females at about 12 weeks of age and several weeks later in males. Onset of diabetes is marked by moderate glycosuria and by a non-fasting hyperglycemia (blood glucose higher than 250 mg/dL). Diabetic mice are hypoinsulinemic and hyperglucagonemic, indicating a selective destruction of pancreatic islet beta cells (Jackson Laboratories website).

Female NOD mice were monitored for blood glucose levels and the study was initiated when blood glucose levels were greater than 250 mg/dL for two consecutive days. NOD mice were treated with 10 mg/kg anti-GCGR antibody, 0.2 mg/kg anti-CD3 antibody, a combination of 10 mg/kg anti-GCGR antibody and 0.2 mg/kg anti-CD3 antibody, or 10 mg/kg anti-KLH control antibody (n=8 or 10 mice per group). For the anti-GCGR antibody and anti-KLH antibody, mice were dosed by subcutaneous injection on a weekly schedule; for the anti-CD3 antibody, mice were dosed by intraperitoneal injection for 5 consecutive days in the first week of treatment. Blood glucose was measured twice a week and plasma C-peptide was measured at week 0, 4, and at the end of the study. The study was terminated approximately 8 weeks after treatment started.

As expected, treatment with the control antibody had no effect and after 2 to 3 weeks all of the mice had blood glucose levels of at least 600 mg/dL. The mice treated with the anti-CD3 antibody had a variety of responses in individual mice: (i) 3 mice had a reduction in glucose levels to near normal levels (between 100 and 200 mg/dL) that was maintained until end of the study, (ii) one mouse had a reduction in glucose levels (approximately 100 mg/dL by week 4) but the reduction was not maintained and by the end of the study its blood glucose was above 500 mg/dL, and (iii) 4 mice had no reduction in glucose levels with increasing glucose levels to at least 600 mg/dL. All of the mice treated with the anti-GCGR antibody had a reduction of glucose levels to approximately 100-200 mg/dL within the first week, however increasing blood glucose levels were observed in all of the mice over the ensuing weeks. Surprisingly, 7 out of 8 mice treated with the combination of anti-GCGR antibody and anti-CD3 antibody showed an immediate (within the first week) reduction of blood glucose to normal levels, i.e., approximately 100 mg/dL which was maintained until the end of the study (FIG. 1).

Figure 2:
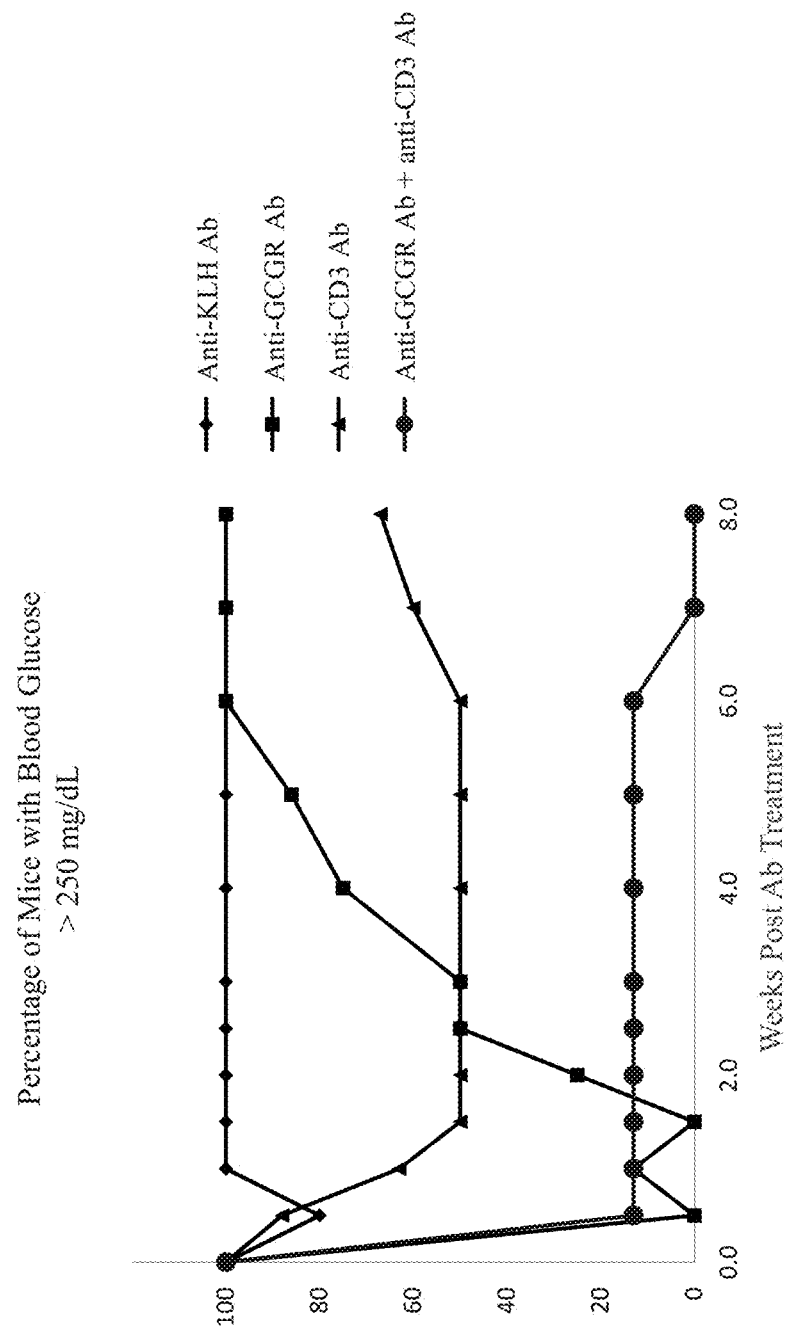
FIG. 2. Percentage of mice with blood glucose levels below 250 mg/dL after treatment.

FIG. 2 shows the results of the study presented as the percentage of mice with a blood glucose level greater than 250 mg/dL (i.e., diabetic) in each treatment group. This figure illustrates the profound effect an anti-GCGR antibody combined with an anti-CD3 antibody had in reducing the percentage of mice with hyperglycemia and diabetes.

Figure 3:
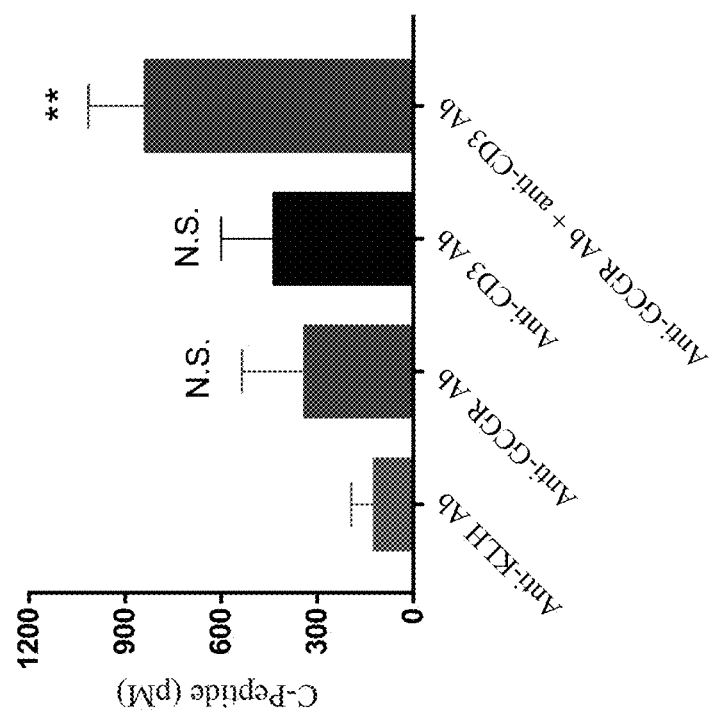
FIG. 3. Plasma C-peptide levels in mice after treatment.

FIG. 3 shows the plasma level of C-peptide in the four treatment groups at the end of the study. The figure shows that treatment with an anti-GCGR antibody in combination with an anti-CD3 antibody resulted in a higher level of C-peptide than either antibody as a single agent.

Figure 4:
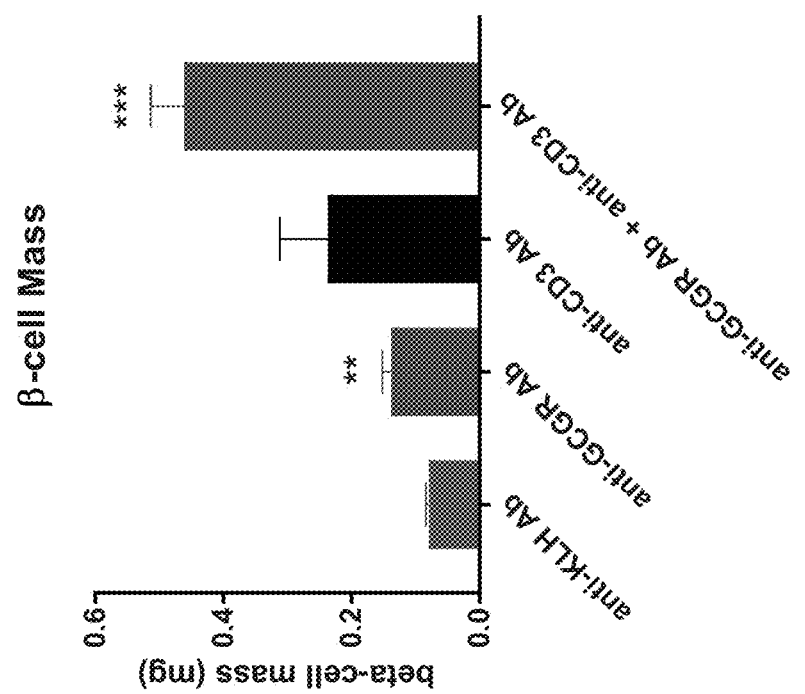
FIG. 4. β-cell mass in mice after treatment.

FIG. 4 shows β-cell mass in the four treatment groups at the end of the study. Quantitative measurement of β-cell mass shows that anti-GCGR antibody alone led to a statistically significant increase. Combination of anti-GCGR and anti-CD3 resulted in a marked increase of β-cell mass compared to either single agent alone. This is accompanied by the significant increase of plasma C-peptide as shown in FIG. 3. Taken together, it demonstrates a synergistic effect on β-cell regeneration by combination of anti-GCGR and anti-CD3.

These results indicate that treatment with a GCGR antagonist (e.g., an anti-GCGR antibody) in combination with an immunotherapeutic agent (e.g., an anti-CD3 antibody) is able to profoundly reduce blood glucose levels and increase β-cell mass in an animal model of autoimmune diabetes and that the combination appears to be more effective than either agent alone.

Although the foregoing present disclosure has been described in some detail by way of illustration and example for purposes of clarity of understanding, the descriptions and examples should not be construed as limiting the scope of the present disclosure. The embodiments of the present disclosure described herein are intended to be merely exemplary, and those skilled in the art will recognize numerous equivalents to the specific procedures described herein. All such equivalents are considered to be within the scope of the present disclosure and are covered by the embodiments.

All publications, patents, patent applications, internet sites, and accession numbers/database sequences including both polynucleotide and polypeptide sequences cited herein are hereby incorporated by reference in their entirety for all purposes to the same extent as if each individual publication, patent, patent application, internet site, or accession number/database sequence were specifically and individually indicated to be so incorporated by reference.

Following are sequences disclosed in the application with the exception of the CDR sequences defined in Tables 1-10.

Human GCGR amino acid sequence with predicted
signal sequence underlined
(SEQ ID NO: 1)
MPPCQPQRPLLLLLLLLACQPQVPSAQVMDFLFEKWKLYGDQCHHNLSLL

PPPTELVCNRTFDKYSCWPDTPANTTANISCPWYLPWHHKVQHRFVFKRC

GPDGQWVRGPRGQPWRDASQCQMDGEEIEVQKEVAKMYSSFQVMYTVGYS

LSLGALLLALAILGGLSKLHCTRNAIHANLFASFVLKASSVLVIDGLLRT

RYSQKIGDDLSVSTWLSDGAVAGCRVAAVFMQYGIVANYCWLLVEGLYLH

NLLGLATLPERSFFSLYLGIGWGAPMLFVVPWAVVKCLFENVQCWTSNDN

MGFWWILRFPVFLAILINFFIFVRIVQLLVAKLRARQMHHTDYKFRLAKS

TLTLIPLLGVHEVVFAFVTDEHAQGTLRSAKLFFDLFLSSFQGLLVAVLY

CFLNKEVQSELRRRWHRWRLGKVLWEERNTSNHRASSSPGHGPPSKELQF

GRGGGSQDSSAETPLAGGLPRLAESPF

Human GCGR amino acid sequence without predicted
signal sequence
(SEQ ID NO: 2)
AQVMDFLFEKWKLYGDQCHHNLSLLPPPTELVCNRTFDKYSCWPDTPANT

TANISCPWYLPWHHKVQHRFVFKRCGPDGQWVRGPRGQPWRDASQCQMDG

EEIEVQKEVAKMYSSFQVMYTVGYSLSLGALLLALAILGGLSKLHCTRNA

IHANLFASFVLKASSVLVIDGLLRTRYSQKIGDDLSVSTWLSDGAVAGCR

VAAVFMQYGIVANYCWLLVEGLYLHNLLGLATLPERSFFSLYLGIGWGAP

MLFVVPWAVVKCLFENVQCWTSNDNMGFWWILRFPVFLAILINFFIFVRI

VQLLVAKLRARQMHHTDYKFRLAKSTLTLIPLLGVHEVVFAFVTDEHAQG

TLRSAKLFFDLFLSSFQGLLVAVLYCFLNKEVQSELRRRWHRWRLGKVLW

EERNTSNHRASSSPGHGPPSKELQFGRGGGSQDSSAETPLAGGLPRLAES

PF

Human GCGR extracellular domain
(amino acids 26-136)
(SEQ ID NO: 3)
AQVMDFLFEKWKLYGDQCHHNLSLLPPPTELVCNRTFDKYSCWPDTPANT

TANISCPWYLPWHHKVQHRFVFKRCGPDGQWVRGPRGQPWRDASQCQMDG

EEIEVQKEVAK

Human GCGR extracellular domain
(amino acids 28-123)
(SEQ ID NO: 4)
VMDFLFEKWKLYGDQCHHNLSLLPPPTELVCNRTFDKYSCWPDTPANTTA

NISCPWYLPWHHKVQHRFVFKRCGPDGQWVRGPRGQPWRDASQCQM

Human GCGR extracellular domain
(amino acids 80-119)
(SEQ ID NO: 5)
SCPWYLPWHHKVQHRFVFKRCGPDGQWVRGPRGQPWRDAS 6B5 Heavy chain variable region
(SEQ ID NO: 12)
QVQLQQSGTELVRPGTSVKISCKASGFTFTNHWLGWVKQRPGHGLEWIGD

IYPGGYYINYNEKFKGKATLTADTSSSTAYMQLSSLTSEDSAVYFCARHT

NYGSDYWGQGTTLTVSS

6B5 Light chain variable region
(SEQ ID NO: 13)
DVLMTQIPLSLPVSLGDQASISCRSSQSIVDSYGNTFLEWYLQKPGQSPK

LLIYKVSNRLSGVPDRFSGTGAGTDFTLKISRVEAEDLGIYYCFQGSHVP

WTFGGGTKLEIK

Hz6B5 Heavy chain variable region
(SEQ ID NO: 14)
QVQLVQSGAEVKKPGSSVKVSCKASGFTFTNHWLGWVRQAPGQGLEWIGD

IYPGGYYINYNEKFKGRVTITADESTSTAYMELSSLRSEDTAVYYCARHT

NYGSDYWGQGTTVTVSS

Hz6B5 Light chain variable region
(SEQ ID NO: 15)
DVVMTQSPLSLPVTLGQPASISCRSSQSIVDSYGNTFLEWYQQRPGQSPR

LLIYKVSNRLSGVPDRFSGSGSGTDFTLKISRVEAEDVGVYYCFQGSHVP

WTFGQGTKLEIK

3H5 Heavy chain variable region
(SEQ ID NO: 22)
QVQLQQSGAELVKPGASVRLSCKASGNTFTNYWMHWVKQRPGQGLEWIGM

IHPNSGSTHYNEKFKNKATLTVDKSSNTAYMQLSGLTSEDSAVYYCGATA

DYVMDYWGQGTSVTVSS

3H5 Light chain variable region
(SEQ ID NO: 23)
DIVLTQTPLSLPVNIGDQASISCKSTKSLLNSDGFTYLDWYLQKPGQSPQ

LLINLVSNRFSGVPDRFSGSGSGTEFILKISRVEAEDLGVYYCFQSNFLP

LTFGAGTKLELK

5B11 Heavy Chain variable region
(SEQ ID NO: 28)
QVQLQQSGAELVKPGASVKLSCKASGNTFTSHWMHWVKQRPGQGLEWIGM

SHPNSGSSNYSGKFKSKATLTVDRSSSTAYMQLNSLTSEDSAVYYCARTD

YDYDGDYWGQGTTLTVSS

5B11 Light Chain variable region
(SEQ ID NO: 29)
DVVLTQTPLSLPVNIGDQASISCKSSKSLLNSDGLTYLDWYLQKPGQSPQ
LLIYLVSNRFSGVPDRFSGSGSGTDFTLKISRVEADDLGVYYCFQSNFLP
LTFGAGTKLELK 1C1 Heavy chain variable region
(SEQ ID NO: 36)
EVQLQQSGPELVKPGATVKMSCKASGYTFTRNVIHWVKQKPGQGLEWIGY
INPYNDGAKYNAKFKGKATVTSDKSSTAYMELSSLTSEDSAVYYCARWG
NYEDFAMDYWGQGTSVTVSS 1C1 Light chain variable region
(SEQ ID NO: 37)
NIVLTQSPPSLAVSLGQRATISCRASESVDIYGNSYMHWYQQKPGQPPKL
LIYLASNLESGVPARFSGSGSRTEFSLTIDPVEAGDAATYYCQQNNEDPF
TFGGGTKLEIK 1C3 Heavy chain variable region
(SEQ ID NO: 44)
EVQLQQSGPELVKPGASVKMSCKASGYTFTSSVMHWVKQKPGQALEWIGY
INPYNDGTKYNENFKGKATLTSDRSSTTAYMELSSLTSEDSAVYYCVTGA
GYDRGPMAMDYWGQGTSVTVSS 1C3 Light chain variable region
(SEQ ID NO: 45)
NIVLTQSPASLAVSLGQRATISCRASESVDSYGDSFVHWYQQKPGQPPKL
LIYFASNLESGVPARFSGSGSRTDFTLTIDPVEADDTATYYCQQNNEVPF
TFGSGTKLELK 1H2 Heavy chain variable region
(SEQ ID NO: 51)
QVQLQQPGAELVKPGASVKMSCKVSGYTFTSYWITWVKQRPGQGLEWIGD
IHPGGGDTNYNKKFKSKATLTVDTSSSTAYMQLSSLTSEDSAVYHCTSDD
NYVGFTYWGQGTLVTVSA 1H2 Light chain variable region
(SEQ ID NO: 52)
DVLMTQTPLSLPVSLGDQASISCRSSQTIIHSDGNTYLEWYLQKPGQSPI
LLIYKVSNRFSGVPDRFSGSGSGTDFTLKISRVEAEDLGVYYCFQGSHVP
WTFGGGTKLEIK 4F8 Heavy chain variable region
(SEQ ID NO: 57)
QVQLQQSGAELVRPGTSVTMSCKAAGYTFSNYWIGWVKQRPGHGLEWIGD
IYPGGFYDNYNDKFKGKATLTTDTSSSTAYMQLSSLTSEDSAIYYCTRSG
GLPGAGFTYWGQGTLVTVSA 4F8 Light chain variable region
(SEQ ID NO: 58)
DVLMTQTPLSLPVSLGDQASISCRSSQHIVYSDGNTYLEWYLQKPGQSPK
LLIYKVSNRFSGVPDRFSGSGSGTDFTLEISRVEAEDLGVYYCFQGSHVP
WTFGGGTKLEIK 13G9 Heavy chain variable region
(SEQ ID NO: 65)
QVQLQQSGAELVRPGTSVKISCKASGYTFTNYWLGWVKQRPGHGLEWIGD
IYPGGDYNNYNGKFKGKATLTADTSSSTAYIQLSSLTSEDSAVYFCVRSD
DGYSWGQGTTLTVSS 13G9 Light chain variable region
(SEQ ID NO: 66)
DVLMTQTPLSLPVSLGDQASISCRSSQSIVDSYGNTYLEWYQQKPGQSPT
LLIYKVSNRFAGVPDRFSGSGSGTDFTLKISRVEAEDLGVYYCFQGSHIPW
TFGGGTKVEIK 14F4 Heavy chain variable region
(SEQ ID NO: 71)
QVQLQQSGAELVRPGTSVNMSCKATGYTFTNYWIGWVKQRPGHGLEWIGD
IFPGGFYSNYNEKFKGKATLTTDTSSSTGYMQLSSLTSEDSAIYYCARIW
DRGFDYWGQGTTLTVSS 14F4 Light chain variable region
(SEQ ID NO: 72)
DVLMTQSPLSLPVSLGDQASISCRSSQSIVDSYGNTYLEWYLQKPGQSPK
LLIYKVSNRFSGVPDRFSGSGSGTDFTLKISRVEAEDRGLYYCFQGSHVP
YTFGGGTKLEIK 14E9 Heavy chain variable region
(SEQ ID NO: 76)
QVQLQQSGAELVRPGTSVKMSCKAAGYTFTNYWIGWVKQRPGHGLEWIGD
ISPGNYYTNYNAKFKDKVSLTADTSSSTAYMQLSSLTSEDSAIYYCARYD
EFAYWGQGTLVTVSA 14E9 Light chain variable region
(SEQ ID NO: 77)
DVLMTQTPLSLSVSLGDQASISCRSSQSIVHSDGNTYLEWYLQKPGQSPK
LLIYKVSNRFSGVPDRFSGSGSGTDFTLKISRVEAEDLGVYYCFQGSHVP
WTFGGGTKLEIK Hz6B5 Heavy chain amino acid sequence with signal
sequence underlined
(SEQ ID NO: 78)
<u>MDMRVPAQLLGLLLLWLRGARC</u>QVQLVQSGAEVKKPGSSVKVSCKASGFT
FTNHWLGWVRQAPGQGLEWIGDIYPGGYYINYNEKFKGRVTITADESTST
AYMELSSLRSEDTAVYYCARHTNYGSDYWGQGTTVTVSSASTKGPSVFPL

APSSKSTSGGTAALGCLVKDYFPEPVTVSWNSGALTSGVHTFPAVLQSSG

LYSLSSVVTVPSSSLGTQTYICNVNHKPSNTKVDKKVEPKSCDKTHTCPP

CPAPALAGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKAL

PAPIEKTISKAKGQPREPQVYTLPPSREEMTKNQVSLTCLVKGFYPSDIA

VEWESNGQPENNYKTTPPVLDSDGSFFLYSKLTVDKSRWQQGNVFSCSVM

HEALHNHYTQKSLSLSPGK

Hz6B5 Heavy chain amino acid sequence without
signal sequence
(SEQ ID NO: 79)
QVQLVQSGAEVKKPGSSVKVSCKASGFTFTNHWLGWVRQAPGQGLEWIGD

IYPGGYYINYNEKFKGRVTITADESTSTAYMELSSLRSEDTAVYYCARHT

NYGSDYWGQGTTVTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKKVEPKSCDKTHTCPPCPAPALAGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGK

Hz6B5 Light chain with signal sequence underlined
(SEQ ID NO: 80)
MDMRVPAQLLGLLLLWLRGARCDVVMTQSPLSLPVTLGQPASISCRSSQS

IVDSYGNTFLEWYQQRPGQSPRLLIYKVSNRLSGVPDRFSGSGSGTDFTL

KISRVEAEDVGVYYCFQGSHVPWTFGQGTKLEIKRTVAAPSVFIFPPSDE

QLKSGTASVVCLLNNFYPREAKVQWKVDNALQSGNSQESVTEQDSKDSTY

SLSSTLTLSKADYEKHKVYACEVTHQGLSSPVTKSFNRGEC

Hz6B5 Light chain without signal sequence
(SEQ ID NO: 81)
DVVMTQSPLSLPVTLGQPASISCRSSQSIVDSYGNTFLEWYQQRPGQSPR

LLIYKVSNRLSGVPDRFSGSGSGTDFTLKISRVEAEDVGVYYCFQGSHVP

WTFGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

Human IgG1 constant region
(SEQ ID NO: 82)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK

Human IgG1 constant region E233A/L235A
(SEQ ID NO: 83)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPALAGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK

Human IgG1 constant region L234A/L235A
(SEQ ID NO: 84)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPEAAGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK

---

What is claimed:

1. A method of reducing a blood glucose level in a human subject, the method comprising administering to the human subject a therapeutically effective amount of a glucagon receptor (GCGR) antagonist and a therapeutically effective amount of an immunotherapeutic agent, wherein the GCGR antagonist is an antibody that specifically binds human GCGR, wherein the immunotherapeutic agent is an anti-CD3 antibody.

2. The method of claim 1, wherein the antibody that specifically binds human GCGR comprises: a heavy chain variable region (VH) comprising a VH complementarity determining region (CDR)1, a VH CDR2, and a VH CDR3 from the amino acid sequence set forth in SEQ ID NO:14; and a light chain variable region (VL) comprising a VL CDR1, a VL CDR2, and a VL CDR3 from the amino acid sequence set forth in SEQ ID NO:15.

3. The method of claim 2, wherein the antibody that specifically binds human GCGR comprises: a VH comprising a VH CDR1 comprising the amino acid sequence of SEQ ID NO:6, a VH CDR2 comprising the amino acid sequence of SEQ ID NO:7, and a VH CDR3 comprising the amino acid sequence of SEQ ID NO:8; and a VL comprising a VL CDR1 comprising the amino acid sequence of SEQ ID NO:9, a VL CDR2 comprising the amino acid sequence of SEQ ID NO:10, and a VL CDR3 comprising the amino acid sequence of SEQ ID NO:11.

4. The method of claim 2, wherein:
(a) the VH of the antibody that specifically binds human GCGR comprises a sequence having at least 90% sequence identity to the amino acid sequence of SEQ ID NO:14; and/or
(b) the VL of the antibody that specifically binds human GCGR comprises a sequence having at least 90% sequence identity to the amino acid sequence of SEQ ID NO:15.

5. The method of claim 2, wherein the VH of the antibody that specifically binds human GCGR comprises the amino acid sequence of SEQ ID NO:14 and the VL of the antibody that specifically binds human GCGR comprises the amino acid sequence of SEQ ID NO:15.

6. The method of claim 2, wherein the antibody that specifically binds human GCGR comprises a heavy chain comprising the amino acid sequence of SEQ ID NO:79 and a light chain comprising the amino acid sequence of SEQ ID NO:81.

7. The method of claim 1, wherein:
(a) the antibody that specifically binds human GCGR comprises: a VH comprising a VH CDR1, a VH CDR2, and a VH CDR3 from the amino acid sequence set forth in SEQ ID NO:22; and a VL comprising a VL CDR1, a VL CDR2, and a VL CDR3 from the amino acid sequence set forth in SEQ ID NO:23;
(b) the antibody that specifically binds human GCGR comprises: a VH comprising a VH CDR1, a VH CDR2, and a VH CDR3 from the amino acid sequence set forth in SEQ ID NO:28; and a VL comprising a VL CDR1, a VL CDR2, and a VL CDR3 from the amino acid sequence set forth in SEQ ID NO:29;
(c) the antibody that specifically binds human GCGR comprises: a VH comprising a VH CDR1, a VH CDR2, and a VH CDR3 from the amino acid sequence set forth in SEQ ID NO:36; and a VL comprising a VL CDR1, a VL CDR2, and a VL CDR3 from the amino acid sequence set forth in SEQ ID NO:37;
(d) the antibody that specifically binds human GCGR comprises: a VH comprising a VH CDR1, a VH CDR2, and a VH CDR3 from the amino acid sequence set forth in SEQ ID NO:44; and a VL comprising a VL CDR1, a VL CDR2, and a VL CDR3 from the amino acid sequence set forth in SEQ ID NO:45;
(e) the antibody that specifically binds human GCGR comprises: a VH comprising a VH CDR1, a VH CDR2, and a VH CDR3 from the amino acid sequence set forth in SEQ ID NO:51; and a VL comprising a VL CDR1, a VL CDR2, and a VL CDR3 from the amino acid sequence set forth in SEQ ID NO:52;

(f) the antibody that specifically binds human GCGR comprises: a VH comprising a VH CDR1, a VH CDR2, and a VH CDR3 from the amino acid sequence set forth in SEQ ID NO:57; and a VL comprising a VL CDR1, a VL CDR2, and a VL CDR3 from the amino acid sequence set forth in SEQ ID NO:58;

(g) the antibody that specifically binds human GCGR comprises: a VH comprising a VH CDR1, a VH CDR2, and a VH CDR3 from the amino acid sequence set forth in SEQ ID NO:65; and a VL comprising a VL CDR1, a VL CDR2, and a VL CDR3 from the amino acid sequence set forth in SEQ ID NO:66;

(h) the antibody that specifically binds human GCGR comprises: a VH comprising a VH CDR1, a VH CDR2, and a VH CDR3 from the amino acid sequence set forth in SEQ ID NO:71; and a VL comprising a VL CDR1, a VL CDR2, and a VL CDR3 from the amino acid sequence set forth in SEQ ID NO:72; or (i) the antibody that specifically binds human GCGR comprises: a VH comprising a VH CDR1, a VH CDR2, and a VH CDR3 from the amino acid sequence set forth in SEQ ID NO:76; and a VL comprising a VL CDR1, a VL CDR2, and a VL CDR3 from the amino acid sequence set forth in SEQ ID NO:77.

8. The method of claim 7, wherein the antibody that specifically binds human GCGR comprises:

(a) a VH comprising a VH CDR1 comprising the amino acid sequence of SEQ ID NO:16, a VH CDR2 comprising the amino acid sequence of SEQ ID NO:17, and a VH CDR3 comprising the amino acid sequence of SEQ ID NO:18; and a VL comprising a VL CDR1 comprising the amino acid sequence of SEQ ID NO:19, a VL CDR2 comprising the amino acid sequence of SEQ ID NO:20, and a VL CDR3 comprising the amino acid sequence of SEQ ID NO:21;

(b) a VH comprising a VH CDR1 comprising the amino acid sequence of SEQ ID NO:24, a VH CDR2 comprising the amino acid sequence of SEQ ID NO:25, and a VH CDR3 comprising the amino acid sequence of SEQ ID NO:26; and a VL comprising a VL CDR1 comprising the amino acid sequence of SEQ ID NO:27, a VL CDR2 comprising the amino acid sequence of SEQ ID NO:20, and a VL CDR3 comprising the amino acid sequence of SEQ ID NO:21;

(c) a VH comprising a VH CDR1 comprising the amino acid sequence of SEQ ID NO:30, a VH CDR2 comprising the amino acid sequence of SEQ ID NO:31, and a VH CDR3 comprising the amino acid sequence of SEQ ID NO:32; and a VL comprising a VL CDR1 comprising the amino acid sequence of SEQ ID NO:33, a VL CDR2 comprising the amino acid sequence of SEQ ID NO:34, and a VL CDR3 comprising the amino acid sequence of SEQ ID NO:35;

(d) a VH comprising a VH CDR1 comprising the amino acid sequence of SEQ ID NO:38, a VH CDR2 comprising the amino acid sequence of SEQ ID NO:39, and a VH CDR3 comprising the amino acid sequence of SEQ ID NO:40; and a VL comprising a VL CDR1 comprising the amino acid sequence of SEQ ID NO:41, a VL CDR2 comprising the amino acid sequence of SEQ ID NO:42, and a VL CDR3 comprising the amino acid sequence of SEQ ID NO:43;

(e) a VH comprising a VH CDR1 comprising the amino acid sequence of SEQ ID NO:46, a VH CDR2 comprising the amino acid sequence of SEQ ID NO:47, and a VH CDR3 comprising the amino acid sequence of SEQ ID NO:48; and a VL comprising a VL CDR1 comprising the amino acid sequence of SEQ ID NO:49, a VL CDR2 comprising the amino acid sequence of SEQ ID NO:50, and a VL CDR3 comprising the amino acid sequence of SEQ ID NO:11;

(f) a VH comprising a VH CDR1 comprising the amino acid sequence of SEQ ID NO:53, a VH CDR2 comprising the amino acid sequence of SEQ ID NO:54, and a VH CDR3 comprising the amino acid sequence of SEQ ID NO:55; and a VL comprising a VL CDR1 comprising the amino acid sequence of SEQ ID NO:56, a VL CDR2 comprising the amino acid sequence of SEQ ID NO:50, and a VL CDR3 comprising the amino acid sequence of SEQ ID NO:11;

(g) a VH comprising a VH CDR1 comprising the amino acid sequence of SEQ ID NO:59, a VH CDR2 comprising the amino acid sequence of SEQ ID NO:60, and a VH CDR3 comprising the amino acid sequence of SEQ ID NO:61; and a VL comprising a VL CDR1 comprising the amino acid sequence of SEQ ID NO:62, a VL CDR2 comprising the amino acid sequence of SEQ ID NO:63, and a VL CDR3 comprising the amino acid sequence of SEQ ID NO:64;

(h) a VH comprising a VH CDR1 comprising the amino acid sequence of SEQ ID NO:67, a VH CDR2 comprising the amino acid sequence of SEQ ID NO:68, and a VH CDR3 comprising the amino acid sequence of SEQ ID NO:69; and a VL comprising a VL CDR1 comprising the amino acid sequence of SEQ ID NO:62, a VL CDR2 comprising the amino acid sequence of SEQ ID NO:50, and a VL CDR3 comprising the amino acid sequence of SEQ ID NO:70; or (i) a VH comprising a VH CDR1 comprising the amino acid sequence of SEQ ID NO:67, a VH CDR2 comprising the amino acid sequence of SEQ ID NO:73, and a VH CDR3 comprising the amino acid sequence of SEQ ID NO:74; and a VL comprising a VL CDR1 comprising the amino acid sequence of SEQ ID NO:75, a VL CDR2 comprising the amino acid sequence of SEQ ID NO:50, and a VL CDR3 comprising the amino acid sequence of SEQ ID NO:11.

9. The method of claim 7, wherein:

(a) the VH of the antibody that specifically binds human GCGR comprises a sequence having at least 90% sequence identity to the amino acid sequence of SEQ ID NO:22; and/or the VL of the antibody that specifically binds human GCGR comprises a sequence having at least 90% sequence identity to the amino acid sequence of SEQ ID NO:23;

(b) the VH of the antibody that specifically binds human GCGR comprises a sequence having at least 90% sequence identity to the amino acid sequence of SEQ ID NO:28; and/or the VL of the antibody that specifically binds human GCGR comprises a sequence having at least 90% sequence identity to the amino acid sequence of SEQ ID NO:29;

(c) the VH of the antibody that specifically binds human GCGR comprises a sequence having at least 90% sequence identity to the amino acid sequence of SEQ ID NO:36; and/or the VL of the antibody that specifically binds human GCGR comprises a sequence having at least 90% sequence identity to the amino acid sequence of SEQ ID NO:37;

(d) the VH of the antibody that specifically binds human GCGR comprises a sequence having at least 90% sequence identity to the amino acid sequence of SEQ ID NO:44; and/or the VL of the antibody that specifically binds human GCGR comprises a sequence having at least 90% sequence identity to the amino acid sequence of SEQ ID NO:45;

(e) the VH of the antibody that specifically binds human GCGR comprises a sequence having at least 90% sequence identity to the amino acid sequence of SEQ ID NO:51; and/or the VL of the antibody that specifically binds human GCGR comprises a sequence having at least 90% sequence identity to the amino acid sequence of SEQ ID NO:52;

(f) the VH of the antibody that specifically binds human GCGR comprises a sequence having at least 90% sequence identity to the amino acid sequence of SEQ ID NO:57; and/or the VL of the antibody that specifically binds human GCGR comprises a sequence having at least 90% sequence identity to the amino acid sequence of SEQ ID NO:58;

(g) the VH of the antibody that specifically binds human GCGR comprises a sequence having at least 90% sequence identity to the amino acid sequence of SEQ ID NO:65; and/or the VL of the antibody that specifically binds human GCGR comprises a sequence having at least 90% sequence identity to the amino acid sequence of SEQ ID NO:66;

(h) the VH of the antibody that specifically binds human GCGR comprises a sequence having at least 90% sequence identity to the amino acid sequence of SEQ ID NO:71; and/or the VL of the antibody that specifically binds human GCGR comprises a sequence having at least 90% sequence identity to the amino acid sequence of SEQ ID NO:72; or (i) the VH of the antibody that specifically binds human GCGR comprises a sequence having at least 90% sequence identity to the amino acid sequence of SEQ ID NO:76; and/or the VL of the antibody that specifically binds human GCGR comprises a sequence having at least 90% sequence identity to the amino acid sequence of SEQ ID NO:77.

10. The method of claim 7, wherein:

(a) the VH of the antibody that specifically binds human GCGR comprises the amino acid sequence of SEQ ID NO:22 and the VL of the antibody that specifically binds human GCGR comprises the amino acid sequence of SEQ ID NO:23;

(b) the VH of the antibody that specifically binds human GCGR comprises the amino acid sequence of SEQ ID NO:28 and the VL of the antibody that specifically binds human GCGR comprises the amino acid sequence of SEQ ID NO:29;

(c) the VH of the antibody that specifically binds human GCGR comprises the amino acid sequence of SEQ ID NO:36 and the VL of the antibody that specifically binds human GCGR comprises the amino acid sequence of SEQ ID NO:37;

(d) the VH of the antibody that specifically binds human GCGR comprises the amino acid sequence of SEQ ID NO:44 and the VL of the antibody that specifically binds human GCGR comprises the amino acid sequence of SEQ ID NO:45;

(e) the VH of the antibody that specifically binds human GCGR comprises the amino acid sequence of SEQ ID NO:51 and the VL of the antibody that specifically binds human GCGR comprises the amino acid sequence of SEQ ID NO:52;

(f) the VH of the antibody that specifically binds human GCGR comprises the amino acid sequence of SEQ ID NO:57 and the VL of the antibody that specifically binds human GCGR comprises the amino acid sequence of SEQ ID NO:58;

(g) the VH of the antibody that specifically binds human GCGR comprises the amino acid sequence of SEQ ID NO:65 and the VL of the antibody that specifically binds human GCGR comprises the amino acid sequence of SEQ ID NO:66;

(h) the VH of the antibody that specifically binds human GCGR comprises the amino acid sequence of SEQ ID NO:71 and the VL of the antibody that specifically binds human GCGR comprises the amino acid sequence of SEQ ID NO:72; or (i) the VH of the antibody that specifically binds human GCGR comprises the amino acid sequence of SEQ ID NO:76 and the VL of the antibody that specifically binds human GCGR comprises the amino acid sequence of SEQ ID NO:77.

11. The method of claim 1, wherein the antibody that specifically binds human GCGR is a humanized antibody.

12. The method of claim 1, wherein the antibody that specifically binds human GCGR is an IgG1 antibody, an IgG2 antibody, or an IgG4 antibody.

13. The method of claim 1, wherein the anti-CD3 antibody is a humanized antibody.

14. The method of claim 1, wherein the anti-CD3 antibody is an IgG1 antibody or an IgG2 antibody.

15. The method of claim 1, wherein the method:
(i) increases C-peptide levels in the blood in the human subject;
(ii) increases C-peptide levels in the pancreas in the human subject;
(iii) reduces HbA1c in the blood in the human subject; and/or
(iv) reduces supplemental insulin use by the human subject.

16. The method of claim 1, which comprises administering at least one additional therapeutic agent to the human subject.

17. The method of claim 16, wherein the at least one additional therapeutic agent is a diabetes or hyperglycemia drug.

18. The method of claim 16, wherein the at least one additional therapeutic agent is an obesity drug, an appetite suppressant, or a weight loss drug.

19. A method of treating hyperglycemia in a human subject, the method comprising administering to the human subject a therapeutically effective amount of a glucagon receptor (GCGR) antagonist and a therapeutically effective amount of an immunotherapeutic agent, wherein the GCGR antagonist is an antibody that specifically binds human GCGR, and wherein the immunotherapeutic agent is an anti-CD3 antibody.

20. The method of claim 19, wherein:
(a) the antibody that specifically binds human GCGR comprises: a heavy chain variable region (VH) comprising a VH complementarity determining region (CDR)1, a VH CDR2, and a VH CDR3 from the amino acid sequence set forth in SEQ ID NO:14; and a light chain variable region (VL) comprising a VL CDR1, a VL CDR2, and a VL CDR3 from the amino acid sequence set forth in SEQ ID NO:15;
(b) the antibody that specifically binds human GCGR comprises: a VH comprising a VH CDR1, a VH CDR2, and a VH CDR3 from the amino acid sequence set forth in SEQ ID NO:22; and a VL comprising a VL CDR1, a VL CDR2, and a VL CDR3 from the amino acid sequence set forth in SEQ ID NO:23;

(c) the antibody that specifically binds human GCGR comprises: a VH comprising a VH CDR1, a VH CDR2, and a VH CDR3 from the amino acid sequence set forth in SEQ ID NO:28; and a VL comprising a VL CDR1, a VL CDR2, and a VL CDR3 from the amino acid sequence set forth in SEQ ID NO:29;

(d) the antibody that specifically binds human GCGR comprises: a VH comprising a VH CDR1, a VH CDR2, and a VH CDR3 from the amino acid sequence set forth in SEQ ID NO:36; and a VL comprising a VL CDR1, a VL CDR2, and a VL CDR3 from the amino acid sequence set forth in SEQ ID NO:37;

(e) the antibody that specifically binds human GCGR comprises: a VH comprising a VH CDR1, a VH CDR2, and a VH CDR3 from the amino acid sequence set forth in SEQ ID NO:44; and a VL comprising a VL CDR1, a VL CDR2, and a VL CDR3 from the amino acid sequence set forth in SEQ ID NO:45;

(f) the antibody that specifically binds human GCGR comprises: a VH comprising a VH CDR1, a VH CDR2, and a VH CDR3 from the amino acid sequence set forth in SEQ ID NO:51; and a VL comprising a VL CDR1, a VL CDR2, and a VL CDR3 from the amino acid sequence set forth in SEQ ID NO:52;

(g) the antibody that specifically binds human GCGR comprises: a VH comprising a VH CDR1, a VH CDR2, and a VH CDR3 from the amino acid sequence set forth in SEQ ID NO:57; and a VL comprising a VL CDR1, a VL CDR2, and a VL CDR3 from the amino acid sequence set forth in SEQ ID NO:58;

(h) the antibody that specifically binds human GCGR comprises: a VH comprising a VH CDR1, a VH CDR2, and a VH CDR3 from the amino acid sequence set forth in SEQ ID NO:65; and a VL comprising a VL CDR1, a VL CDR2, and a VL CDR3 from the amino acid sequence set forth in SEQ ID NO:66;

(i) the antibody that specifically binds human GCGR comprises: a VH comprising a VH CDR1, a VH CDR2, and a VH CDR3 from the amino acid sequence set forth in SEQ ID NO:71; and a VL comprising a VL CDR1, a VL CDR2, and a VL CDR3 from the amino acid sequence set forth in SEQ ID NO:72; or (j) the antibody that specifically binds human GCGR comprises: a VH comprising a VH CDR1, a VH CDR2, and a VH CDR3 from the amino acid sequence set forth in SEQ ID NO:76; and a VL comprising a VL CDR1, a VL CDR2, and a VL CDR3 from the amino acid sequence set forth in SEQ ID NO:77.

21. The method of claim 20, wherein the antibody that specifically binds human GCGR comprises:

(a) a VH comprising a VH CDR1 comprising the amino acid sequence of SEQ ID NO:6, a VH CDR2 comprising the amino acid sequence of SEQ ID NO:7, and a VH CDR3 comprising the amino acid sequence of SEQ ID NO:8; and a VL comprising a VL CDR1 comprising the amino acid sequence of SEQ ID NO:9, a VL CDR2 comprising the amino acid sequence of SEQ ID NO:10, and a VL CDR3 comprising the amino acid sequence of SEQ ID NO:11;

(b) a VH comprising a VH CDR1 comprising the amino acid sequence of SEQ ID NO:16, a VH CDR2 comprising the amino acid sequence of SEQ ID NO:17, and a VH CDR3 comprising the amino acid sequence of SEQ ID NO:18; and a VL comprising a VL CDR1 comprising the amino acid sequence of SEQ ID NO:19, a VL CDR2 comprising the amino acid sequence of SEQ ID NO:20, and a VL CDR3 comprising the amino acid sequence of SEQ ID NO:21;

(c) a VH comprising a VH CDR1 comprising the amino acid sequence of SEQ ID NO:24, a VH CDR2 comprising the amino acid sequence of SEQ ID NO:25, and a VH CDR3 comprising the amino acid sequence of SEQ ID NO:26; and a VL comprising a VL CDR1 comprising the amino acid sequence of SEQ ID NO:27, a VL CDR2 comprising the amino acid sequence of SEQ ID NO:20, and a VL CDR3 comprising the amino acid sequence of SEQ ID NO:21;

(d) a VH comprising a VH CDR1 comprising the amino acid sequence of SEQ ID NO:30, a VH CDR2 comprising the amino acid sequence of SEQ ID NO:31, and a VH CDR3 comprising the amino acid sequence of SEQ ID NO:32; and a VL comprising a VL CDR1 comprising the amino acid sequence of SEQ ID NO:33, a VL CDR2 comprising the amino acid sequence of SEQ ID NO:34, and a VL CDR3 comprising the amino acid sequence of SEQ ID NO:35;

(e) a VH comprising a VH CDR1 comprising the amino acid sequence of SEQ ID NO:38, a VH CDR2 comprising the amino acid sequence of SEQ ID NO:39, and a VH CDR3 comprising the amino acid sequence of SEQ ID NO:40; and a VL comprising a VL CDR1 comprising the amino acid sequence of SEQ ID NO:41, a VL CDR2 comprising the amino acid sequence of SEQ ID NO:42, and a VL CDR3 comprising the amino acid sequence of SEQ ID NO:43;

(f) a VH comprising a VH CDR1 comprising the amino acid sequence of SEQ ID NO:46, a VH CDR2 comprising the amino acid sequence of SEQ ID NO:47, and a VH CDR3 comprising the amino acid sequence of SEQ ID NO:48; and a VL comprising a VL CDR1 comprising the amino acid sequence of SEQ ID NO:49, a VL CDR2 comprising the amino acid sequence of SEQ ID NO:50, and a VL CDR3 comprising the amino acid sequence of SEQ ID NO:11;

(g) a VH comprising a VH CDR1 comprising the amino acid sequence of SEQ ID NO:53, a VH CDR2 comprising the amino acid sequence of SEQ ID NO:54, and a VH CDR3 comprising the amino acid sequence of SEQ ID NO:55; and a VL comprising a VL CDR1 comprising the amino acid sequence of SEQ ID NO:56, a VL CDR2 comprising the amino acid sequence of SEQ ID NO:50, and a VL CDR3 comprising the amino acid sequence of SEQ ID NO:11;

(h) a VH comprising a VH CDR1 comprising the amino acid sequence of SEQ ID NO:59, a VH CDR2 comprising the amino acid sequence of SEQ ID NO:60, and a VH CDR3 comprising the amino acid sequence of SEQ ID NO:61; and a VL comprising a VL CDR1 comprising the amino acid sequence of SEQ ID NO:62, a VL CDR2 comprising the amino acid sequence of SEQ ID NO:63, and a VL CDR3 comprising the amino acid sequence of SEQ ID NO:64;

(i) a VH comprising a VH CDR1 comprising the amino acid sequence of SEQ ID NO:67, a VH CDR2 comprising the amino acid sequence of SEQ ID NO:68, and a VH CDR3 comprising the amino acid sequence of SEQ ID NO:69; and a VL comprising a VL CDR1 comprising the amino acid sequence of SEQ ID NO:62, a VL CDR2 comprising the amino acid sequence of SEQ ID NO:50, and a VL CDR3 comprising the amino acid sequence of SEQ ID NO:70; or (j) a VH comprising a VH CDR1 comprising the amino acid sequence of SEQ ID NO:67, a VH CDR2 comprising the amino acid sequence of SEQ ID NO:73, and a VH CDR3 comprising the amino acid sequence of SEQ ID NO:74; and a VL comprising a VL CDR1 comprising the amino acid sequence of SEQ ID NO:75, a VL CDR2 comprising the amino acid sequence of SEQ ID NO:50, and a VL CDR3 comprising the amino acid sequence of SEQ ID NO:11.

22. A method of increasing beta cell mass or beta cell regeneration in a human subject, the method comprising administering to the human subject a therapeutically effective amount of a glucagon receptor (GCGR) antagonist and a therapeutically effective amount of an immunotherapeutic agent, wherein the GCGR antagonist is an antibody that specifically binds human GCGR, and wherein the immunotherapeutic agent is an anti-CD3 antibody.

23. The method of claim 22, wherein the antibody that specifically binds human GCGR comprises:

(a) a heavy chain variable region (VH) comprising a VH complementarity determining region (CDR)1 comprising the amino acid sequence of SEQ ID NO:6, a VH CDR2 comprising the amino acid sequence of SEQ ID NO:7, and a VH CDR3 comprising the amino acid sequence of SEQ ID NO:8; and a light chain variable region (VL) comprising a VL CDR1 comprising the amino acid sequence of SEQ ID NO:9, a VL CDR2 comprising the amino acid sequence of SEQ ID NO:10, and a VL CDR3 comprising the amino acid sequence of SEQ ID NO:11;

(b) a VH comprising a VH CDR1 comprising the amino acid sequence of SEQ ID NO:16, a VH CDR2 comprising the amino acid sequence of SEQ ID NO:17, and a VH CDR3 comprising the amino acid sequence of SEQ ID NO:18; and a VL comprising a VL CDR1 comprising the amino acid sequence of SEQ ID NO:19, a VL CDR2 comprising the amino acid sequence of SEQ ID NO:20, and a VL CDR3 comprising the amino acid sequence of SEQ ID NO:21;

(c) a VH comprising a VH CDR1 comprising the amino acid sequence of SEQ ID NO:24, a VH CDR2 comprising the amino acid sequence of SEQ ID NO:25, and a VH CDR3 comprising the amino acid sequence of SEQ ID NO:26; and a VL comprising a VL CDR1 comprising the amino acid sequence of SEQ ID NO:27, a VL CDR2 comprising the amino acid sequence of SEQ ID NO:20, and a VL CDR3 comprising the amino acid sequence of SEQ ID NO:21;

(d) a VH comprising a VH CDR1 comprising the amino acid sequence of SEQ ID NO:30, a VH CDR2 comprising the amino acid sequence of SEQ ID NO:31, and a VH CDR3 comprising the amino acid sequence of SEQ ID NO:32; and a VL comprising a VL CDR1 comprising the amino acid sequence of SEQ ID NO:33, a VL CDR2 comprising the amino acid sequence of SEQ ID NO:34, and a VL CDR3 comprising the amino acid sequence of SEQ ID NO:35;

(e) a VH comprising a VH CDR1 comprising the amino acid sequence of SEQ ID NO:38, a VH CDR2 comprising the amino acid sequence of SEQ ID NO:39, and a VH CDR3 comprising the amino acid sequence of SEQ ID NO:40; and a VL comprising a VL CDR1 comprising the amino acid sequence of SEQ ID NO:41, a VL CDR2 comprising the amino acid sequence of SEQ ID NO:42, and a VL CDR3 comprising the amino acid sequence of SEQ ID NO:43;

(f) a VH comprising a VH CDR1 comprising the amino acid sequence of SEQ ID NO:46, a VH CDR2 comprising the amino acid sequence of SEQ ID NO:47, and a VH CDR3 comprising the amino acid sequence of SEQ ID NO:48; and a VL comprising a VL CDR1 comprising the amino acid sequence of SEQ ID NO:49, a VL CDR2 comprising the amino acid sequence of SEQ ID NO:50, and a VL CDR3 comprising the amino acid sequence of SEQ ID NO:11;

(g) a VH comprising a VH CDR1 comprising the amino acid sequence of SEQ ID NO:53, a VH CDR2 comprising the amino acid sequence of SEQ ID NO:54, and a VH CDR3 comprising the amino acid sequence of SEQ ID NO:55; and a VL comprising a VL CDR1 comprising the amino acid sequence of SEQ ID NO:56, a VL CDR2 comprising the amino acid sequence of SEQ ID NO:50, and a VL CDR3 comprising the amino acid sequence of SEQ ID NO:11;

(h) a VH comprising a VH CDR1 comprising the amino acid sequence of SEQ ID NO:59, a VH CDR2 comprising the amino acid sequence of SEQ ID NO:60, and a VH CDR3 comprising the amino acid sequence of SEQ ID NO:61; and a VL comprising a VL CDR1 comprising the amino acid sequence of SEQ ID NO:62, a VL CDR2 comprising the amino acid sequence of SEQ ID NO:63, and a VL CDR3 comprising the amino acid sequence of SEQ ID NO:64;

(i) a VH comprising a VH CDR1 comprising the amino acid sequence of SEQ ID NO:67, a VH CDR2 comprising the amino acid sequence of SEQ ID NO:68, and a VH CDR3 comprising the amino acid sequence of SEQ ID NO:69; and a VL comprising a VL CDR1 comprising the amino acid sequence of SEQ ID NO:62, a VL CDR2 comprising the amino acid sequence of SEQ ID NO:50, and a VL CDR3 comprising the amino acid sequence of SEQ ID NO:70; or (j) a VH comprising a VH CDR1 comprising the amino acid sequence of SEQ ID NO:67, a VH CDR2 comprising the amino acid sequence of SEQ ID NO:73, and a VH CDR3 comprising the amino acid sequence of SEQ ID NO:74; and a VL comprising a VL CDR1 comprising the amino acid sequence of SEQ ID NO:75, a VL CDR2 comprising the amino acid sequence of SEQ ID NO:50, and a VL CDR3 comprising the amino acid sequence of SEQ ID NO:11.

* * * * *

UNITED STATES PATENT AND TRADEMARK OFFICE
CERTIFICATE OF CORRECTION

| | | |
|---|---|---|
| PATENT NO. | : 11,845,802 B2 | Page 1 of 1 |
| APPLICATION NO. | : 17/177762 | |
| DATED | : December 19, 2023 | |
| INVENTOR(S) | : Zhonghao Liu | |

It is certified that error appears in the above-identified patent and that said Letters Patent is hereby corrected as shown below:

On the Title Page

Item (54), in the Title:
Delete "THERAPY" and insert -- THERAPIES --.

In the Specification

Column 1, Line 1:
Delete "THERAPY" and insert -- THERAPIES --.

Signed and Sealed this
Sixth Day of February, 2024

Katherine Kelly Vidal
*Director of the United States Patent and Trademark Office*

SEQUENCE LISTING

<160> NUMBER OF SEQ ID NOS: 85

<210> SEQ ID NO 1
<211> LENGTH: 477
<212> TYPE: PRT
<213> ORGANISM: Homo sapiens

<400> SEQUENCE: 1

Met Pro Pro Cys Gln Pro Gln Arg Pro Leu Leu Leu Leu Leu Leu
1               5                   10                  15

Leu Ala Cys Gln Pro Gln Val Pro Ser Ala Gln Val Met Asp Phe Leu
            20                  25                  30

-continued

```
Phe Glu Lys Trp Lys Leu Tyr Gly Asp Gln Cys His His Asn Leu Ser
         35                  40                  45

Leu Leu Pro Pro Pro Thr Glu Leu Val Cys Asn Arg Thr Phe Asp Lys
 50                  55                  60

Tyr Ser Cys Trp Pro Asp Thr Pro Ala Asn Thr Thr Ala Asn Ile Ser
 65                  70                  75                  80

Cys Pro Trp Tyr Leu Pro Trp His His Lys Val Gln His Arg Phe Val
                 85                  90                  95

Phe Lys Arg Cys Gly Pro Asp Gly Gln Trp Val Arg Gly Pro Arg Gly
             100                 105                 110

Gln Pro Trp Arg Asp Ala Ser Gln Cys Gln Met Asp Gly Glu Glu Ile
         115                 120                 125

Glu Val Gln Lys Glu Val Ala Lys Met Tyr Ser Ser Phe Gln Val Met
130                 135                 140

Tyr Thr Val Gly Tyr Ser Leu Ser Leu Gly Ala Leu Leu Leu Ala Leu
145                 150                 155                 160

Ala Ile Leu Gly Gly Leu Ser Lys Leu His Cys Thr Arg Asn Ala Ile
                 165                 170                 175

His Ala Asn Leu Phe Ala Ser Phe Val Leu Lys Ala Ser Ser Val Leu
             180                 185                 190

Val Ile Asp Gly Leu Leu Arg Thr Arg Tyr Ser Gln Lys Ile Gly Asp
         195                 200                 205

Asp Leu Ser Val Ser Thr Trp Leu Ser Asp Gly Ala Val Ala Gly Cys
         210                 215                 220

Arg Val Ala Ala Val Phe Met Gln Tyr Gly Ile Val Ala Asn Tyr Cys
225                 230                 235                 240

Trp Leu Leu Val Glu Gly Leu Tyr Leu His Asn Leu Leu Gly Leu Ala
                 245                 250                 255

Thr Leu Pro Glu Arg Ser Phe Phe Ser Leu Tyr Leu Gly Ile Gly Trp
             260                 265                 270

Gly Ala Pro Met Leu Phe Val Val Pro Trp Ala Val Val Lys Cys Leu
         275                 280                 285

Phe Glu Asn Val Gln Cys Trp Thr Ser Asn Asp Asn Met Gly Phe Trp
290                 295                 300

Trp Ile Leu Arg Phe Pro Val Phe Leu Ala Ile Leu Ile Asn Phe Phe
305                 310                 315                 320

Ile Phe Val Arg Ile Val Gln Leu Leu Val Ala Lys Leu Arg Ala Arg
                 325                 330                 335

Gln Met His His Thr Asp Tyr Lys Phe Arg Leu Ala Lys Ser Thr Leu
             340                 345                 350

Thr Leu Ile Pro Leu Leu Gly Val His Glu Val Val Phe Ala Phe Val
         355                 360                 365

Thr Asp Glu His Ala Gln Gly Thr Leu Arg Ser Ala Lys Leu Phe Phe
370                 375                 380

Asp Leu Phe Leu Ser Ser Phe Gln Gly Leu Leu Val Ala Val Leu Tyr
385                 390                 395                 400

Cys Phe Leu Asn Lys Glu Val Gln Ser Glu Leu Arg Arg Arg Trp His
             405                 410                 415

Arg Trp Arg Leu Gly Lys Val Leu Trp Glu Arg Asn Thr Ser Asn
         420                 425                 430

His Arg Ala Ser Ser Ser Pro Gly His Gly Pro Pro Ser Lys Glu Leu
             435                 440                 445

Gln Phe Gly Arg Gly Gly Gly Ser Gln Asp Ser Ser Ala Glu Thr Pro
```

```
            450                 455                 460
Leu Ala Gly Gly Leu Pro Arg Leu Ala Glu Ser Pro Phe
465                 470                 475

<210> SEQ ID NO 2
<211> LENGTH: 452
<212> TYPE: PRT
<213> ORGANISM: Homo sapiens

<400> SEQUENCE: 2

Ala Gln Val Met Asp Phe Leu Phe Glu Lys Trp Lys Leu Tyr Gly Asp
1               5                   10                  15

Gln Cys His His Asn Leu Ser Leu Leu Pro Pro Thr Glu Leu Val
            20                  25                  30

Cys Asn Arg Thr Phe Asp Lys Tyr Ser Cys Trp Pro Asp Thr Pro Ala
            35                  40                  45

Asn Thr Thr Ala Asn Ile Ser Cys Pro Trp Tyr Leu Pro Trp His His
        50                  55                  60

Lys Val Gln His Arg Phe Val Phe Lys Arg Cys Gly Pro Asp Gly Gln
65                  70                  75                  80

Trp Val Arg Gly Pro Arg Gly Gln Pro Trp Arg Asp Ala Ser Gln Cys
                85                  90                  95

Gln Met Asp Gly Glu Glu Ile Glu Val Gln Lys Glu Val Ala Lys Met
            100                 105                 110

Tyr Ser Ser Phe Gln Val Met Tyr Thr Val Gly Tyr Ser Leu Ser Leu
        115                 120                 125

Gly Ala Leu Leu Leu Ala Leu Ala Ile Leu Gly Gly Leu Ser Lys Leu
    130                 135                 140

His Cys Thr Arg Asn Ala Ile His Ala Asn Leu Phe Ala Ser Phe Val
145                 150                 155                 160

Leu Lys Ala Ser Ser Val Leu Val Ile Asp Gly Leu Leu Arg Thr Arg
                165                 170                 175

Tyr Ser Gln Lys Ile Gly Asp Asp Leu Ser Val Ser Thr Trp Leu Ser
            180                 185                 190

Asp Gly Ala Val Ala Gly Cys Arg Val Ala Ala Val Phe Met Gln Tyr
        195                 200                 205

Gly Ile Val Ala Asn Tyr Cys Trp Leu Leu Val Glu Gly Leu Tyr Leu
    210                 215                 220

His Asn Leu Leu Gly Leu Ala Thr Leu Pro Glu Arg Ser Phe Phe Ser
225                 230                 235                 240

Leu Tyr Leu Gly Ile Gly Trp Gly Ala Pro Met Leu Phe Val Val Pro
                245                 250                 255

Trp Ala Val Val Lys Cys Leu Phe Glu Asn Val Gln Cys Trp Thr Ser
            260                 265                 270

Asn Asp Asn Met Gly Phe Trp Trp Ile Leu Arg Phe Pro Val Phe Leu
        275                 280                 285

Ala Ile Leu Ile Asn Phe Phe Ile Phe Val Arg Ile Val Gln Leu Leu
    290                 295                 300

Val Ala Lys Leu Arg Ala Arg Gln Met His His Thr Asp Tyr Lys Phe
305                 310                 315                 320

Arg Leu Ala Lys Ser Thr Leu Thr Leu Ile Pro Leu Leu Gly Val His
                325                 330                 335

Glu Val Val Phe Ala Phe Val Thr Asp Glu His Ala Gln Gly Thr Leu
            340                 345                 350
```

```
Arg Ser Ala Lys Leu Phe Phe Asp Leu Phe Leu Ser Ser Phe Gln Gly
            355                 360                 365

Leu Leu Val Ala Val Leu Tyr Cys Phe Leu Asn Lys Glu Val Gln Ser
    370                 375                 380

Glu Leu Arg Arg Arg Trp His Arg Trp Arg Leu Gly Lys Val Leu Trp
385                 390                 395                 400

Glu Glu Arg Asn Thr Ser Asn His Arg Ala Ser Ser Pro Gly His
                405                 410                 415

Gly Pro Pro Ser Lys Glu Leu Gln Phe Gly Arg Gly Gly Ser Gln
            420                 425                 430

Asp Ser Ser Ala Glu Thr Pro Leu Ala Gly Gly Leu Pro Arg Leu Ala
            435                 440                 445

Glu Ser Pro Phe
    450

<210> SEQ ID NO 3
<211> LENGTH: 111
<212> TYPE: PRT
<213> ORGANISM: Homo sapiens

<400> SEQUENCE: 3

Ala Gln Val Met Asp Phe Leu Phe Glu Lys Trp Lys Leu Tyr Gly Asp
1               5                   10                  15

Gln Cys His His Asn Leu Ser Leu Leu Pro Pro Thr Glu Leu Val
            20                  25                  30

Cys Asn Arg Thr Phe Asp Lys Tyr Ser Cys Trp Pro Asp Thr Pro Ala
            35                  40                  45

Asn Thr Thr Ala Asn Ile Ser Cys Pro Trp Tyr Leu Pro Trp His His
    50                  55                  60

Lys Val Gln His Arg Phe Val Phe Lys Arg Cys Gly Pro Asp Gly Gln
65                  70                  75                  80

Trp Val Arg Gly Pro Arg Gly Gln Pro Trp Arg Asp Ala Ser Gln Cys
                85                  90                  95

Gln Met Asp Gly Glu Glu Ile Glu Val Gln Lys Glu Val Ala Lys
            100                 105                 110

<210> SEQ ID NO 4
<211> LENGTH: 96
<212> TYPE: PRT
<213> ORGANISM: Homo sapiens

<400> SEQUENCE: 4

Val Met Asp Phe Leu Phe Glu Lys Trp Lys Leu Tyr Gly Asp Gln Cys
1               5                   10                  15

His His Asn Leu Ser Leu Leu Pro Pro Thr Glu Leu Val Cys Asn
            20                  25                  30

Arg Thr Phe Asp Lys Tyr Ser Cys Trp Pro Asp Thr Pro Ala Asn Thr
            35                  40                  45

Thr Ala Asn Ile Ser Cys Pro Trp Tyr Leu Pro Trp His His Lys Val
    50                  55                  60

Gln His Arg Phe Val Phe Lys Arg Cys Gly Pro Asp Gly Gln Trp Val
65                  70                  75                  80

Arg Gly Pro Arg Gly Gln Pro Trp Arg Asp Ala Ser Gln Cys Gln Met
                85                  90                  95

<210> SEQ ID NO 5
<211> LENGTH: 40
```

```
<212> TYPE: PRT
<213> ORGANISM: Homo sapiens

<400> SEQUENCE: 5

Ser Cys Pro Trp Tyr Leu Pro Trp His His Lys Val Gln His Arg Phe
1               5                   10                  15

Val Phe Lys Arg Cys Gly Pro Asp Gly Gln Trp Val Arg Gly Pro Arg
            20                  25                  30

Gly Gln Pro Trp Arg Asp Ala Ser
        35                  40

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Phe Thr Phe Thr Asn His Trp Leu Gly
1               5                   10

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Ile Tyr Pro Gly Gly Tyr Tyr Ile Asn Tyr Asn Glu Lys Phe Lys
1               5                   10                  15

Gly

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

His Thr Asn Tyr Gly Ser Asp Tyr
1               5

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Ser Ser Gln Ser Ile Val Asp Ser Tyr Gly Asn Thr Phe Leu Glu
1               5                   10                  15

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 10

Lys Val Ser Asn Arg Leu Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Phe Gln Gly Ser His Val Pro Trp Thr
1               5

<210> SEQ ID NO 12
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Gln Gln Ser Gly Thr Glu Leu Val Arg Pro Gly Thr
1               5                   10                  15

Ser Val Lys Ile Ser Cys Lys Ala Ser Gly Phe Thr Phe Thr Asn His
            20                  25                  30

Trp Leu Gly Trp Val Lys Gln Arg Pro Gly His Gly Leu Glu Trp Ile
        35                  40                  45

Gly Asp Ile Tyr Pro Gly Gly Tyr Tyr Ile Asn Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg His Thr Asn Tyr Gly Ser Asp Tyr Trp Gly Gln Gly Thr Thr
            100                 105                 110

Leu Thr Val Ser Ser
        115

<210> SEQ ID NO 13
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Val Leu Met Thr Gln Ile Pro Leu Ser Leu Pro Val Ser Leu Gly
1               5                   10                  15

Asp Gln Ala Ser Ile Ser Cys Arg Ser Ser Gln Ser Ile Val Asp Ser
            20                  25                  30

Tyr Gly Asn Thr Phe Leu Glu Trp Tyr Leu Gln Lys Pro Gly Gln Ser
        35                  40                  45

Pro Lys Leu Leu Ile Tyr Lys Val Ser Asn Arg Leu Ser Gly Val Pro
    50                  55                  60

```
Asp Arg Phe Ser Gly Thr Gly Ala Gly Thr Asp Phe Thr Leu Lys Ile
 65                  70                  75                  80

Ser Arg Val Glu Ala Glu Asp Leu Gly Ile Tyr Tyr Cys Phe Gln Gly
                 85                  90                  95

Ser His Val Pro Trp Thr Phe Gly Gly Gly Thr Lys Leu Glu Ile Lys
            100                 105                 110

<210> SEQ ID NO 14
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Gln Ser Gly Ala Glu Val Lys Lys Pro Gly Ser
  1               5                  10                  15

Ser Val Lys Val Ser Cys Lys Ala Ser Gly Phe Thr Phe Thr Asn His
                 20                  25                  30

Trp Leu Gly Trp Val Arg Gln Ala Pro Gly Gln Gly Leu Glu Trp Ile
             35                  40                  45

Gly Asp Ile Tyr Pro Gly Gly Tyr Tyr Ile Asn Tyr Asn Glu Lys Phe
 50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg His Thr Asn Tyr Gly Ser Asp Tyr Trp Gly Gln Gly Thr Thr
            100                 105                 110

Val Thr Val Ser Ser
            115

<210> SEQ ID NO 15
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Ile Val Asp Ser
                 20                  25                  30

Tyr Gly Asn Thr Phe Leu Glu Trp Tyr Gln Gln Arg Pro Gly Gln Ser
             35                  40                  45

Pro Arg Leu Leu Ile Tyr Lys Val Ser Asn Arg Leu Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Trp Thr Phe Gly Gln Gly Thr Lys Leu Glu Ile Lys
            100                 105                 110

<210> SEQ ID NO 16
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Asn Thr Phe Thr Asn Tyr Trp Met His
1               5                   10

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met Ile His Pro Asn Ser Gly Ser Thr His Tyr Asn Glu Lys Phe Lys
1               5                   10                  15

Asn

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Ala Asp Tyr Val Met Asp Tyr
1               5

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Ser Thr Lys Ser Leu Leu Asn Ser Asp Gly Phe Thr Tyr Leu Asp
1               5                   10                  15

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Val Ser Asn Arg Phe Ser
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21
```

```
Phe Gln Ser Asn Phe Leu Pro Leu Thr
1               5
```

<210> SEQ ID NO 22
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Gln Val Gln Leu Gln Gln Ser Gly Ala Glu Leu Val Lys Pro Gly Ala
1               5                   10                  15

Ser Val Arg Leu Ser Cys Lys Ala Ser Gly Asn Thr Phe Thr Asn Tyr
            20                  25                  30

Trp Met His Trp Val Lys Gln Arg Pro Gly Gln Gly Leu Glu Trp Ile
        35                  40                  45

Gly Met Ile His Pro Asn Ser Gly Ser Thr His Tyr Asn Glu Lys Phe
    50                  55                  60

Lys Asn Lys Ala Thr Leu Thr Val Asp Lys Ser Ser Asn Thr Ala Tyr
65                  70                  75                  80

Met Gln Leu Ser Gly Leu Thr Ser Glu Asp Ser Ala Val Tyr Tyr Cys
                85                  90                  95

Gly Ala Thr Ala Asp Tyr Val Met Asp Tyr Trp Gly Gln Gly Thr Ser
            100                 105                 110

Val Thr Val Ser Ser
        115
```

<210> SEQ ID NO 23
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Asp Ile Val Leu Thr Gln Thr Pro Leu Ser Leu Pro Val Asn Ile Gly
1               5                   10                  15

Asp Gln Ala Ser Ile Ser Cys Lys Ser Thr Lys Ser Leu Leu Asn Ser
            20                  25                  30

Asp Gly Phe Thr Tyr Leu Asp Trp Tyr Leu Gln Lys Pro Gly Gln Ser
        35                  40                  45

Pro Gln Leu Leu Ile Asn Leu Val Ser Asn Arg Phe Ser Gly Val Pro
    50                  55                  60

Asp Arg Phe Ser Gly Ser Gly Ser Gly Thr Glu Phe Ile Leu Lys Ile
65                  70                  75                  80

Ser Arg Val Glu Ala Glu Asp Leu Gly Val Tyr Tyr Cys Phe Gln Ser
                85                  90                  95

Asn Phe Leu Pro Leu Thr Phe Gly Ala Gly Thr Lys Leu Glu Leu Lys
            100                 105                 110
```

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Asn Thr Phe Thr Ser His Trp Met His
1               5                   10

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Met Ser His Pro Asn Ser Gly Ser Ser Asn Tyr Ser Gly Lys Phe Lys
1               5                   10                  15

Ser

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Asp Tyr Asp Tyr Asp Gly Asp Tyr
1               5

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Ser Ser Lys Ser Leu Leu Asn Ser Asp Gly Leu Thr Tyr Leu Asp
1               5                   10                  15

<210> SEQ ID NO 28
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Val Gln Leu Gln Gln Ser Gly Ala Glu Leu Val Lys Pro Gly Ala
1               5                   10                  15

Ser Val Lys Leu Ser Cys Lys Ala Ser Gly Asn Thr Phe Thr Ser His
                20                  25                  30

Trp Met His Trp Val Lys Gln Arg Pro Gly Gln Gly Leu Glu Trp Ile
            35                  40                  45

Gly Met Ser His Pro Asn Ser Gly Ser Ser Asn Tyr Ser Gly Lys Phe
        50                  55                  60

Lys Ser Lys Ala Thr Leu Thr Val Asp Arg Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Thr Asp Tyr Asp Tyr Asp Gly Asp Tyr Trp Gly Gln Gly Thr
            100                 105                 110

Thr Leu Thr Val Ser Ser
        115

<210> SEQ ID NO 29
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Val Val Leu Thr Gln Thr Pro Leu Ser Leu Pro Val Asn Ile Gly
1               5                   10                  15

Asp Gln Ala Ser Ile Ser Cys Lys Ser Ser Lys Ser Leu Leu Asn Ser
            20                  25                  30

Asp Gly Leu Thr Tyr Leu Asp Trp Tyr Leu Gln Lys Pro Gly Gln Ser
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Leu Gly Val Tyr Tyr Cys Phe Gln Ser
                85                  90                  95

Asn Phe Leu Pro Leu Thr Phe Gly Ala Gly Thr Lys Leu Glu Leu Lys
            100                 105                 110

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Tyr Thr Phe Thr Arg Asn Val Ile His
1               5                   10

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Tyr Ile Asn Pro Tyr Asn Asp Gly Ala Lys Tyr Asn Ala Lys Phe Lys
1               5                   10                  15

Gly

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

```
Trp Gly Asn Tyr Glu Asp Phe Ala Met Asp Tyr
1               5                   10
```

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

```
Arg Ala Ser Glu Ser Val Asp Ile Tyr Gly Asn Ser Tyr Met His
1               5                   10                  15
```

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

```
Leu Ala Ser Asn Leu Glu Ser
1               5
```

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

```
Gln Gln Asn Asn Glu Asp Pro Phe Thr
1               5
```

<210> SEQ ID NO 36
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Glu Val Gln Leu Gln Gln Ser Gly Pro Glu Leu Val Lys Pro Gly Ala
1               5                   10                  15

Thr Val Lys Met Ser Cys Lys Ala Ser Gly Tyr Thr Phe Thr Arg Asn
            20                  25                  30

Val Ile His Trp Val Lys Gln Lys Pro Gly Gln Gly Leu Glu Trp Ile
        35                  40                  45

Gly Tyr Ile Asn Pro Tyr Asn Asp Gly Ala Lys Tyr Asn Ala Lys Phe
    50                  55                  60

Lys Gly Lys Ala Thr Val Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Trp Gly Asn Tyr Glu Asp Phe Ala Met Asp Tyr Trp Gly Gln
            100                 105                 110

Gly Thr Ser Val Thr Val Ser Ser
        115                 120
```

<210> SEQ ID NO 37
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asn Ile Val Leu Thr Gln Ser Pro Pro Ser Leu Ala Val Ser Leu Gly
1               5                   10                  15
Gln Arg Ala Thr Ile Ser Cys Arg Ala Ser Glu Ser Val Asp Ile Tyr
            20                  25                  30
Gly Asn Ser Tyr Met His Trp Tyr Gln Gln Lys Pro Gly Gln Pro Pro
        35                  40                  45
Lys Leu Leu Ile Tyr Leu Ala Ser Asn Leu Glu Ser Gly Val Pro Ala
    50                  55                  60
Arg Phe Ser Gly Ser Gly Ser Arg Thr Glu Phe Ser Leu Thr Ile Asp
65                  70                  75                  80
Pro Val Glu Ala Gly Asp Ala Ala Thr Tyr Tyr Cys Gln Gln Asn Asn
                85                  90                  95
Glu Asp Pro Phe Thr Phe Gly Gly Gly Thr Lys Leu Glu Ile Lys
            100                 105                 110

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Tyr Thr Phe Thr Ser Ser Val Met His
1               5                   10

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Tyr Ile Asn Pro Tyr Asn Asp Gly Thr Lys Tyr Asn Glu Asn Phe Lys
1               5                   10                  15
Gly

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Ala Gly Tyr Asp Arg Gly Pro Met Ala Met Asp Tyr
1               5                   10

<210> SEQ ID NO 41

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Ala Ser Glu Ser Val Asp Ser Tyr Gly Asp Ser Phe Val His
1               5                   10                  15

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Phe Ala Ser Asn Leu Glu Ser
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Gln Asn Asn Glu Val Pro Phe Thr
1               5

<210> SEQ ID NO 44
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Ser
                20                  25                  30

Val Met His Trp Val Lys Gln Lys Pro Gly Gln Ala Leu Glu Trp Ile
            35                  40                  45

Gly Tyr Ile Asn Pro Tyr Asn Asp Gly Thr Lys Tyr Asn Glu Asn Phe
        50                  55                  60

Lys Gly Lys Ala Thr Leu Thr Ser Asp Arg Ser Ser Thr Thr Ala Tyr
65                  70                  75                  80

Met Glu Leu Ser Ser Leu Thr Ser Glu Asp Ser Ala Val Tyr Tyr Cys
                85                  90                  95

Val Thr Gly Ala Gly Tyr Asp Arg Gly Pro Met Ala Met Asp Tyr Trp
            100                 105                 110

Gly Gln Gly Thr Ser Val Thr Val Ser Ser
        115                 120

<210> SEQ ID NO 45
<211> LENGTH: 111
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 45

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asp Ser Phe Val His Trp Tyr Gln Gln Lys Pro Gly Gln Pro Pro
        35                  40                  45

Lys Leu Leu Ile Tyr Phe Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Thr Ala Thr Tyr Tyr Cys Gln Gln Asn Asn
                85                  90                  95

Glu Val Pro Phe Thr Phe Gly Ser Gly Thr Lys Leu Glu Leu Lys
            100                 105                 110

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Tyr Thr Phe Thr Ser Tyr Trp Ile Thr
1               5                   10

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Asp Ile His Pro Gly Gly Gly Asp Thr Asn Tyr Asn Lys Lys Phe Lys
1               5                   10                  15

Ser

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asp Asp Asn Tyr Val Gly Phe Thr Tyr
1               5

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 49

Arg Ser Ser Gln Thr Ile Ile His Ser Asp Gly Asn Thr Tyr Leu Glu
1               5                   10                  15

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Lys Val Ser Asn Arg Phe Ser
1               5

<210> SEQ ID NO 51
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Val Gln Leu Gln Gln Pro Gly Ala Glu Leu Val Lys Pro Gly Ala
1               5                   10                  15

Ser Val Lys Met Ser Cys Lys Val Ser Gly Tyr Thr Phe Thr Ser Tyr
            20                  25                  30

Trp Ile Thr Trp Val Lys Gln Arg Pro Gly Gln Gly Leu Glu Trp Ile
        35                  40                  45

Gly Asp Ile His Pro Gly Gly Asp Thr Asn Tyr Asn Lys Lys Phe
    50                  55                  60

Lys Ser Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr His Cys
                85                  90                  95

Thr Ser Asp Asp Asn Tyr Val Gly Phe Thr Tyr Trp Gly Gln Gly Thr
            100                 105                 110

Leu Val Thr Val Ser Ala
        115

<210> SEQ ID NO 52
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Ile His Ser
            20                  25                  30

Asp Gly Asn Thr Tyr Leu Glu Trp Tyr Leu Gln Lys Pro Gly Gln Ser
        35                  40                  45

Pro Ile Leu Leu Ile Tyr Lys Val Ser Asn Arg Phe Ser Gly Val Pro
    50                  55                  60

```
Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Trp Thr Phe Gly Gly Gly Thr Lys Leu Glu Ile Lys
            100                 105                 110

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Tyr Thr Phe Ser Asn Tyr Trp Ile Gly
 1               5                  10

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Ile Tyr Pro Gly Gly Phe Tyr Asp Asn Tyr Asn Asp Lys Phe Lys
 1               5                  10                  15

Gly

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Gly Gly Leu Pro Gly Ala Gly Phe Thr Tyr
 1               5                  10

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Ser Ser Gln His Ile Val Tyr Ser Asp Gly Asn Thr Tyr Leu Glu
 1               5                  10                  15

<210> SEQ ID NO 57
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Gln Gln Ser Gly Ala Glu Leu Val Arg Pro Gly Thr
```

```
                1               5                   10                  15
Ser Val Thr Met Ser Cys Lys Ala Ala Gly Tyr Thr Phe Ser Asn Tyr
                20                  25                  30

Trp Ile Gly Trp Val Lys Gln Arg Pro Gly His Gly Leu Glu Trp Ile
                35                  40                  45

Gly Asp Ile Tyr Pro Gly Gly Phe Tyr Asp Asn Tyr Asn Asp Lys Phe
            50                  55                  60

Lys Gly Lys Ala Thr Leu Thr Thr Asp Thr Ser Ser Thr Ala Tyr
65                  70                  75                  80

Met Gln Leu Ser Ser Leu Thr Ser Glu Asp Ser Ala Ile Tyr Tyr Cys
                85                  90                  95

Thr Arg Ser Gly Gly Leu Pro Gly Ala Gly Phe Thr Tyr Trp Gly Gln
                100                 105                 110

Gly Thr Leu Val Thr Val Ser Ala
                115                 120
```

<210> SEQ ID NO 58
<211> LENGTH: 112
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 58

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln His Ile Val Tyr Ser
                20                  25                  30

Asp Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Glu Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
                100                 105                 110
```

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 59

```
Gly Tyr Thr Phe Thr Asn Tyr Trp Leu Gly
1               5                   10
```

<210> SEQ ID NO 60
<211> LENGTH: 17
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 60

```
Asp Ile Tyr Pro Gly Gly Asp Tyr Asn Asn Tyr Asn Gly Lys Phe Lys
1               5                   10                  15

Gly

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ser Asp Asp Gly Tyr Ser
1               5

<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Arg Ser Ser Gln Ser Ile Val Asp Ser Tyr Gly Asn Thr Tyr Leu Glu
1               5                   10                  15

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Lys Val Ser Asn Arg Phe Ala
1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Phe Gln Gly Ser His Ile Pro Trp Thr
1               5

<210> SEQ ID NO 65
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Gln Gln Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
                20                  25                  30
```

Trp Leu Gly Trp Val Lys Gln Arg Pro Gly His Gly Leu Glu Trp Ile
            35                  40                  45

Gly Asp Ile Tyr Pro Gly Asp Tyr Asn Asn Tyr Asn Gly Lys Phe
 50                  55                  60

Lys Gly Lys Ala Thr Leu Thr Ala Asp Thr Ser Ser Ser Thr Ala Tyr
 65                  70                  75                  80

Ile Gln Leu Ser Ser Leu Thr Ser Glu Asp Ser Ala Val Tyr Phe Cys
                 85                  90                  95

Val Arg Ser Asp Asp Gly Tyr Ser Trp Gly Gln Gly Thr Thr Leu Thr
            100                 105                 110

Val Ser Ser
       115

<210> SEQ ID NO 66
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val Asp Ser
             20                  25                  30

Tyr Gly Asn Thr Tyr Leu Glu Trp Tyr Gln Gln Lys Pro Gly Gln Ser
         35                  40                  45

Pro Thr Leu Leu Ile Tyr Lys Val Ser Asn Arg Phe Ala Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Ile Pro Trp Thr Phe Gly Gly Gly Thr Lys Val Glu Ile Lys
            100                 105                 110

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Tyr Thr Phe Thr Asn Tyr Trp Ile Gly
 1               5                  10

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Ile Phe Pro Gly Gly Phe Tyr Ser Asn Tyr Asn Glu Lys Phe Lys
 1               5                  10                  15

Gly

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

Ile Trp Asp Arg Gly Phe Asp Tyr
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Phe Gln Gly Ser His Val Pro Tyr Thr
1               5

<210> SEQ ID NO 71
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 71

Gln Val Gln Leu Gln Gln Ser Gly Ala Glu Leu Val Arg Pro Gly Thr
1               5                   10                  15

Ser Val Asn Met Ser Cys Lys Ala Thr Gly Tyr Thr Phe Thr Asn Tyr
                20                  25                  30

Trp Ile Gly Trp Val Lys Gln Arg Pro Gly His Gly Leu Glu Trp Ile
            35                  40                  45

Gly Asp Ile Phe Pro Gly Gly Phe Tyr Ser Asn Tyr Asn Glu Lys Phe
        50                  55                  60

Lys Gly Lys Ala Thr Leu Thr Thr Asp Thr Ser Ser Ser Thr Gly Tyr
65                  70                  75                  80

Met Gln Leu Ser Ser Leu Thr Ser Glu Asp Ser Ala Ile Tyr Tyr Cys
                85                  90                  95

Ala Arg Ile Trp Asp Arg Gly Phe Asp Tyr Trp Gly Gln Gly Thr Thr
            100                 105                 110

Leu Thr Val Ser Ser
        115

<210> SEQ ID NO 72
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 72

Asp Val Leu Met Thr Gln Ser Pro Leu Ser Leu Pro Val Ser Leu Gly
1               5                   10                  15

Asp Gln Ala Ser Ile Ser Cys Arg Ser Ser Gln Ser Ile Val Asp Ser

```
                    20                  25                  30

Tyr Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Arg Gly Leu Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 73
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Asp Ile Ser Pro Gly Asn Tyr Tyr Thr Asn Tyr Asn Ala Lys Phe Lys
1               5                   10                  15

Asp

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Tyr Asp Glu Phe Ala Tyr
1               5

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Arg Ser Ser Gln Ser Ile Val His Ser Asp Gly Asn Thr Tyr Leu Glu
1               5                   10                  15

<210> SEQ ID NO 76
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gln Val Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn Tyr
            20                  25                  30

Trp Ile Gly Trp Val Lys Gln Arg Pro Gly His Gly Leu Glu Trp Ile
```

```
                35                  40                  45
Gly Asp Ile Ser Pro Gly Asn Tyr Tyr Thr Asn Tyr Asn Ala Lys Phe
        50                  55                  60

Lys Asp Lys Val Ser Leu Thr Ala Asp Thr Ser Ser Thr Ala Tyr
 65                  70                  75                  80

Met Gln Leu Ser Ser Leu Thr Ser Glu Asp Ser Ala Ile Tyr Tyr Cys
                85                  90                  95

Ala Arg Tyr Asp Glu Phe Ala Tyr Trp Gly Gln Gly Thr Leu Val Thr
                100                 105                 110

Val Ser Ala
        115

<210> SEQ ID NO 77
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Asp Val Leu Met Thr Gln Thr Pro Leu Ser Leu Ser Val Ser Leu Gly
 1               5                  10                  15

Asp Gln Ala Ser Ile Ser Cys Arg Ser Ser Gln Ser Ile Val His Ser
                20                  25                  30

Asp Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
                100                 105                 110

<210> SEQ ID NO 78
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Met Asp Met Arg Val Pro Ala Gln Leu Leu Gly Leu Leu Leu Leu Trp
 1               5                  10                  15

Leu Arg Gly Ala Arg Cys Gln Val Gln Leu Val Gln Ser Gly Ala Glu
                20                  25                  30

Val Lys Lys Pro Gly Ser Ser Val Lys Val Ser Cys Lys Ala Ser Gly
            35                  40                  45

Phe Thr Phe Thr Asn His Trp Leu Gly Trp Val Arg Gln Ala Pro Gly
        50                  55                  60

Gln Gly Leu Glu Trp Ile Gly Asp Ile Tyr Pro Gly Tyr Tyr Ile
 65                  70                  75                  80

Asn Tyr Asn Glu Lys Phe Lys Gly Arg Val Thr Ile Thr Ala Asp Glu
                85                  90                  95

Ser Thr Ser Thr Ala Tyr Met Glu Leu Ser Ser Leu Arg Ser Glu Asp
```

```
              100                 105                 110
Thr Ala Val Tyr Tyr Cys Ala Arg His Thr Asn Tyr Gly Ser Asp Tyr
            115                 120                 125
Trp Gly Gln Gly Thr Thr Val Thr Val Ser Ser Ala Ser Thr Lys Gly
        130                 135                 140
Pro Ser Val Phe Pro Leu Ala Pro Ser Ser Lys Ser Thr Ser Gly Gly
145                 150                 155                 160
Thr Ala Ala Leu Gly Cys Leu Val Lys Asp Tyr Phe Pro Glu Pro Val
                165                 170                 175
Thr Val Ser Trp Asn Ser Gly Ala Leu Thr Ser Gly Val His Thr Phe
            180                 185                 190
Pro Ala Val Leu Gln Ser Ser Gly Leu Tyr Ser Leu Ser Ser Val Val
        195                 200                 205
Thr Val Pro Ser Ser Ser Leu Gly Thr Gln Thr Tyr Ile Cys Asn Val
    210                 215                 220
Asn His Lys Pro Ser Asn Thr Lys Val Asp Lys Lys Val Glu Pro Lys
225                 230                 235                 240
Ser Cys Asp Lys Thr His Thr Cys Pro Pro Cys Pro Ala Pro Ala Leu
                245                 250                 255
Ala Gly Gly Pro Ser Val Phe Leu Phe Pro Pro Lys Pro Lys Asp Thr
            260                 265                 270
Leu Met Ile Ser Arg Thr Pro Glu Val Thr Cys Val Val Val Asp Val
        275                 280                 285
Ser His Glu Asp Pro Glu Val Lys Phe Asn Trp Tyr Val Asp Gly Val
    290                 295                 300
Glu Val His Asn Ala Lys Thr Lys Pro Arg Glu Glu Gln Tyr Asn Ser
305                 310                 315                 320
Thr Tyr Arg Val Val Ser Val Leu Thr Val Leu His Gln Asp Trp Leu
                325                 330                 335
Asn Gly Lys Glu Tyr Lys Cys Lys Val Ser Asn Lys Ala Leu Pro Ala
            340                 345                 350
Pro Ile Glu Lys Thr Ile Ser Lys Ala Lys Gly Gln Pro Arg Glu Pro
        355                 360                 365
Gln Val Tyr Thr Leu Pro Pro Ser Arg Glu Glu Met Thr Lys Asn Gln
    370                 375                 380
Val Ser Leu Thr Cys Leu Val Lys Gly Phe Tyr Pro Ser Asp Ile Ala
385                 390                 395                 400
Val Glu Trp Glu Ser Asn Gly Gln Pro Glu Asn Asn Tyr Lys Thr Thr
                405                 410                 415
Pro Pro Val Leu Asp Ser Asp Gly Ser Phe Phe Leu Tyr Ser Lys Leu
            420                 425                 430
Thr Val Asp Lys Ser Arg Trp Gln Gln Gly Asn Val Phe Ser Cys Ser
        435                 440                 445
Val Met His Glu Ala Leu His Asn His Tyr Thr Gln Lys Ser Leu Ser
    450                 455                 460
Leu Ser Pro Gly Lys
465

<210> SEQ ID NO 79
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 79

```
Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asn His
            20                  25                  30

Trp Leu Gly Trp Val Arg Gln Ala Pro Gly Gln Gly Leu Glu Trp Ile
        35                  40                  45

Gly Asp Ile Tyr Pro Gly Gly Tyr Tyr Ile Asn Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Thr Asn Tyr Gly Ser Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Ala Leu Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
```

```
                   405                 410                 415
Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 80
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Asp Met Arg Val Pro Ala Gln Leu Leu Gly Leu Leu Leu Leu Trp
1               5                   10                  15

Leu Arg Gly Ala Arg Cys Asp Val Val Met Thr Gln Ser Pro Leu Ser
            20                  25                  30

Leu Pro Val Thr Leu Gly Gln Pro Ala Ser Ile Ser Cys Arg Ser Ser
        35                  40                  45

Gln Ser Ile Val Asp Ser Tyr Gly Asn Thr Phe Leu Glu Trp Tyr Gln
    50                  55                  60

Gln Arg Pro Gly Gln Ser Pro Arg Leu Leu Ile Tyr Lys Val Ser Asn
65                  70                  75                  80

Arg Leu Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Phe Gln Gly Ser His Val Pro Trp Thr Phe Gly Gln Gly
        115                 120                 125

Thr Lys Leu Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys

<210> SEQ ID NO 81
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asp Val Val Met Thr Gln Ser Pro Leu Ser Leu Pro Val Thr Leu Gly
1               5                   10                  15
```

-continued

```
Gln Pro Ala Ser Ile Ser Cys Arg Ser Ser Gln Ser Ile Val Asp Ser
             20                  25                  30

Tyr Gly Asn Thr Phe Leu Glu Trp Tyr Gln Gln Arg Pro Gly Gln Ser
         35                  40                  45

Pro Arg Leu Leu Ile Tyr Lys Val Ser Asn Arg Leu Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Trp Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 82
<211> LENGTH: 330
<212> TYPE: PRT
<213> ORGANISM: Homo sapiens

<400> SEQUENCE: 82

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
            165                 170                 175
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 83
<211> LENGTH: 330
<212> TYPE: PRT
<213> ORGANISM: Homo sapiens

<400> SEQUENCE: 83

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Ala Leu Ala Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205
```

```
      Lys Ala Leu Pro Ala Pro Ile Glu Lys Thr Ile Ser Lys Ala Lys Gly
          210                 215                 220

Gln Pro Arg Glu Pro Gln Val Tyr Thr Leu Pro Pro Ser Arg Glu Glu
      225                 230                 235                 240

Met Thr Lys Asn Gln Val Ser Leu Thr Cys Leu Val Lys Gly Phe Tyr
                      245                 250                 255

Pro Ser Asp Ile Ala Val Glu Trp Glu Ser Asn Gly Gln Pro Glu Asn
                  260                 265                 270

Asn Tyr Lys Thr Thr Pro Pro Val Leu Asp Ser Asp Gly Ser Phe Phe
              275                 280                 285

Leu Tyr Ser Lys Leu Thr Val Asp Lys Ser Arg Trp Gln Gln Gly Asn
          290                 295                 300

Val Phe Ser Cys Ser Val Met His Glu Ala Leu His Asn His Tyr Thr
      305                 310                 315                 320

Gln Lys Ser Leu Ser Leu Ser Pro Gly Lys
                      325                 330

<210> SEQ ID NO 84
<211> LENGTH: 330
<212> TYPE: PRT
<213> ORGANISM: Homo sapiens

<400> SEQUENCE: 84

Ala Ser Thr Lys Gly Pro Ser Val Phe Pro Leu Ala Pro Ser Ser Lys
      1               5                   10                  15

Ser Thr Ser Gly Gly Thr Ala Ala Leu Gly Cys Leu Val Lys Asp Tyr
                      20                  25                  30

Phe Pro Glu Pro Val Thr Val Ser Trp Asn Ser Gly Ala Leu Thr Ser
                  35                  40                  45

Gly Val His Thr Phe Pro Ala Val Leu Gln Ser Ser Gly Leu Tyr Ser
              50                  55                  60

Leu Ser Ser Val Val Thr Val Pro Ser Ser Ser Leu Gly Thr Gln Thr
      65                  70                  75                  80

Tyr Ile Cys Asn Val Asn His Lys Pro Ser Asn Thr Lys Val Asp Lys
                      85                  90                  95

Lys Val Glu Pro Lys Ser Cys Asp Lys Thr His Thr Cys Pro Pro Cys
                  100                 105                 110

Pro Ala Pro Glu Ala Ala Gly Gly Pro Ser Val Phe Leu Phe Pro Pro
              115                 120                 125

Lys Pro Lys Asp Thr Leu Met Ile Ser Arg Thr Pro Glu Val Thr Cys
      130                 135                 140

Val Val Val Asp Val Ser His Glu Asp Pro Glu Val Lys Phe Asn Trp
      145                 150                 155                 160

Tyr Val Asp Gly Val Glu Val His Asn Ala Lys Thr Lys Pro Arg Glu
                      165                 170                 175

Glu Gln Tyr Asn Ser Thr Tyr Arg Val Val Ser Val Leu Thr Val Leu
                  180                 185                 190

His Gln Asp Trp Leu Asn Gly Lys Glu Tyr Lys Cys Lys Val Ser Asn
              195                 200                 205

Lys Ala Leu Pro Ala Pro Ile Glu Lys Thr Ile Ser Lys Ala Lys Gly
          210                 215                 220

Gln Pro Arg Glu Pro Gln Val Tyr Thr Leu Pro Pro Ser Arg Glu Glu
      225                 230                 235                 240

Met Thr Lys Asn Gln Val Ser Leu Thr Cys Leu Val Lys Gly Phe Tyr
                      245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 85

His His His His His His
1               5
```